US011566236B2

(12) United States Patent
Chakraborty et al.

(10) Patent No.: US 11,566,236 B2
(45) Date of Patent: Jan. 31, 2023

(54) MATERIALS AND METHODS FOR TREATMENT OF HEMOGLOBINOPATHIES

(71) Applicant: Vertex Pharmaceuticals Incorporated, Boston, MA (US)

(72) Inventors: Tirtha Chakraborty, Cambridge, MA (US); Michelle I-Ching Lin, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/267,693

(22) Filed: Feb. 5, 2019

(65) Prior Publication Data

US 2019/0284542 A1 Sep. 19, 2019

Related U.S. Application Data

(60) Provisional application No. 62/626,423, filed on Feb. 5, 2018.

(51) Int. Cl.

| | |
|---|---|
| *C12N 9/22* | (2006.01) |
| *A61P 7/00* | (2006.01) |
| *A61K 9/00* | (2006.01) |
| *A61K 35/28* | (2015.01) |
| *A61K 48/00* | (2006.01) |
| *C12N 15/11* | (2006.01) |
| *A61P 7/06* | (2006.01) |
| *C12N 15/113* | (2010.01) |
| *A61K 31/395* | (2006.01) |
| *A61K 38/19* | (2006.01) |
| *C12N 5/0789* | (2010.01) |
| *C12N 5/074* | (2010.01) |
| *A61K 31/7125* | (2006.01) |
| *A61K 31/712* | (2006.01) |

(52) U.S. Cl.
CPC .............. *C12N 9/22* (2013.01); *A61K 9/0019* (2013.01); *A61K 31/395* (2013.01); *A61K 35/28* (2013.01); *A61K 38/193* (2013.01); *A61K 48/0066* (2013.01); *A61P 7/00* (2018.01); *A61P 7/06* (2018.01); *C12N 5/0647* (2013.01); *C12N 5/0696* (2013.01); *C12N 15/11* (2013.01); *C12N 15/113* (2013.01); *A61K 31/712* (2013.01); *A61K 31/7125* (2013.01); *C12N 2310/20* (2017.05); *C12N 2310/315* (2013.01); *C12N 2310/346* (2013.01); *C12N 2506/45* (2013.01); *C12N 2800/80* (2013.01)

(58) Field of Classification Search
CPC ...................................................... C12N 9/22
See application file for complete search history.

(56) References Cited

U.S. PATENT DOCUMENTS

| | | | |
|---|---|---|---|
| 9,738,693 B2 | 8/2017 | Telford et al. | |
| 9,840,538 B2 | 12/2017 | Telford et al. | |
| 2015/0044772 A1 | 2/2015 | Zhao | |
| 2015/0166969 A1 | 6/2015 | Takeuchi et al. | |
| 2015/0168547 A1 | 6/2015 | Lee et al. | |
| 2015/0183025 A1 | 7/2015 | Aoki | |
| 2015/0307867 A1 | 10/2015 | Orkin et al. | |
| 2016/0029604 A1 | 2/2016 | Fahrenkrug et al. | |
| 2016/0289675 A1 | 10/2016 | Ryan et al. | |
| 2017/0191123 A1 | 7/2017 | Kim et al. | |
| 2018/0016589 A1* | 1/2018 | Gao | C12N 15/8213 |
| 2018/0094033 A1 | 4/2018 | Telford et al. | |
| 2018/0112213 A1 | 4/2018 | Welstead et al. | |
| 2018/0119140 A1 | 5/2018 | Porteus et al. | |
| 2018/0179521 A1 | 6/2018 | Rahdar et al. | |
| 2021/0180091 A1 | 6/2021 | Chakraborty et al. | |

FOREIGN PATENT DOCUMENTS

| | | | | |
|---|---|---|---|---|
| WO | WO 2013/176772 A1 | 11/2013 | | |
| WO | WO 2014/093712 A1 | 6/2014 | | |
| WO | WO 2014/204723 A1 | 12/2014 | | |
| WO | WO 2015/026885 A1 | 2/2015 | | |
| WO | WO 2015/168547 A2 | 11/2015 | | |
| WO | WO 2015/183025 A1 | 12/2015 | | |
| WO | WO 2016/164356 A1 | 10/2016 | | |
| WO | WO 2016/182917 A1 | 11/2016 | | |
| WO | WO 2016/183298 A2 | 11/2016 | | |
| WO | WO-2016182917 A1 * | 11/2016 | ........... | C12N 15/102 |
| WO | WO 2017/115268 A1 | 7/2017 | | |
| WO | WO-2017115268 A1 * | 7/2017 | ........... | C12N 15/113 |
| WO | WO 2017/182881 A2 | 10/2017 | | |
| WO | WO 2018/081470 A1 | 5/2018 | | |

(Continued)

OTHER PUBLICATIONS

Costa et al. Genome Editing Using Engineered Nucleases and Their Use in Genomic Screening. In: Assay Guidance Manual. Eli Lilly & Company and the National Center for Advancing Translational Sciences, Bethesda (MD); 2017 (Year: 2017).*
Koonin et. al. Diversity, classification and evolution of CRISPR-Cas systems. 2017. Current Opinion in Microbiology, 37:67-78 (Year: 2017).*
Invitation to Pay Additional Fees dated Jul. 25, 2017, in connection with Application No. PCT/IB2017/000577.
International Search Report and Written Opinion dated Oct. 25, 2017, in connection with Application No. PCT/IB2017/000577.
International Preliminary Report on Patentability dated Nov. 1, 2018, in connection with Application No. PCT/IB2017/000577.

(Continued)

*Primary Examiner* — Scarlett Y Goon
*Assistant Examiner* — Tiffany Nicole Grooms
(74) *Attorney, Agent, or Firm* — Wolf, Greenfield & Sacks, P.C.

(57) ABSTRACT

Materials and methods for treating a patient with a hemoglobinopathy, both ex vivo and in vivo, and materials and methods for creating permanent changes to the genome that can result in at least one deletion, insertion, modulation, or inactivation of a transcriptional control sequence of a BCL11A gene in a cell by genome editing.

17 Claims, 19 Drawing Sheets

Specification includes a Sequence Listing.

(56) References Cited

FOREIGN PATENT DOCUMENTS

WO    WO 2018/218135 A1    11/2018

OTHER PUBLICATIONS

International Search Report and Written Opinion dated Mar. 11, 2019, in connection with Application No. PCT/US2018/063973.
Bauer et al., Hemoglobin switching's surprise: the versatile transcription factor BCL11A is a master repressor of fetal hemoglobin. Curr Opin Genet Dev. Aug. 2015;33:62-70. Doi: 10.1016/j.gde.2015.08.001. Epub Sep. 14, 2015.
Bauer et al., An erythroid enhancer of BCL11A subject to genetic variation determines fetal hemoglobin level. Science. Oct. 11, 2013;342(6155):253-7. Doi: 10.1126/science.1242088.
Bauer et al., Fine-mapping and genome editing reveal an essential erythroid enhancer at the HbF-associated BCL11A locus. Blood. Nov. 15, 2013;122(21):437.
Bauer et al., CRISPR-CAS9 saturating mutagenesis reveals an Achilles heel in the BCL11A erythroid enhancer for fetal hemoglobin induction (by genome editing). Blood. Dec. 2015;126(23). 57th Annual Meeting of the American Society of Hematoloy. Orlando, FL. Dec. 5-8, 2015.
Blobel et al., An international effort to cure a global health problem: A report on the 19th Hemoglobin Switching Conference. Exp Hematol. Oct. 2015;43(10):821-37. Doi: 10.1016/j.exphem.2015.06.008. Epub Jul. 2, 2015.
Brinkman et al., Easy quantification of template-directed CRISPR/Cas9 editing. Nucleic Acids Res. Jun. 1, 2018;46(10):e58. Doi: 10.1093/nar/gky164.
Brinkman et al., Easy quantitative assessment of genome editing by sequence trace decomposition. Nucleic Acids Res. Dec. 16, 2014;42(22):e168. Doi: 10.1093/nar/gku936. Epub Oct. 9, 2014.
Canver et al., Customizing the genome as therapy for the β-hemoglobinopathies. Blood. May 26, 2016;127(21):2536-45. Doi: 10.1182/blood-2016-01-678128. Epub Apr. 6, 2016.
Canver et al., BCL11A enhancer dissection by Cas9-mediated in situ saturating mutagenesis. Nature. Nov. 12, 2015;527(7577):192-7. Doi: 10.1038/nature15521. Epub Sep. 16, 2015.
Deltcheva et al., CRISPR RNA maturation by trans-encoded small RNA and host factor RnaseIII. Nature. Mar. 31, 2011;471(7340):602-7. Doi: 10.1038/nature09886.
Ferrari et al., Gene Therapy Approaches to Hemoglobinopathies. Hematol Oncol Clin North Am. Oct. 2017;31(5):835-852. doi: 10.1016/j.hoc.2017.06.010.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. Doi: 10.1093/nar/gkt1074. Epub Nov. 22, 2013.
Jinek et al., A programmable dual-RNA-guided DNA endonuclease in adaptive bacterial immunity. Science. Aug. 17, 2012;337(6096):816-21. Doi: 10.1126/science.1225829. Epub Jun. 28, 2012.
Li et al., Efficient CRISPR-Cas9 mediated gene disruption in primary erythroid progenitor cells. Haematologica. Jun. 2016;101(6):e216-9. Doi: 10.3324/haematol.2015.135723. Epub Mar. 11, 2016.
Li et al., Genome editing in erythroid progenitor cells mediated by Crisp/CAS9. Blood. Dec. 2014;124(12). 56th Annual Meeting of the American Society of Hematology. San Francisco, CA. Dec. 6-9, 2014.
Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.
Orkin, Recent advances in globin research using genome-wide association studies and gene editing. Ann N Y Acad Sci. Mar. 2016;1368(1):5-10. Doi: 10.1111/nyas.13001. Epub Feb. 11, 2016.
[No Author Listed], Gene therapy cures patient with sickle cell disease. Article Image. Accessed Jun. 2020. 1 page.
[No Author Listed], CRISPR Therapeutics and Vertex Announce New Clinical Data for Investigational Gene-Editing Therapy CTX001™ in Severe Hemoglobinopathies at the 25th Annual European Hematology Association (EHA) Congress. Vertex. Retrieved from: <https://news.vrtx.com/press-release/crispr-therapeutics-and-vertex-announce-new-clinical-data-investigational-gene>. Accessed on Jun. 25, 2020. 11 pages.
Haridy, More early data revealed from landmark CRISPR gene editing human trial. New Atlas.Jun. 16, 2020. Retrieved from: <https://newatlas.com/medical/early-data-ctx001-crispr-gene-editing-human-trial/>. 6 pages.
Kuchler, Crispr puts first human in-body gene editing to test. Financial Times. Jan. 7, 2020. 6 pages.
Le Page, Three people with inherited diseases successfully treated with CRISPR. NewScientist. Jun. 12, 2020. Retrieved from: <https://www.newscientist.com/article/2246020-three-people-with-inherited-diseases-successfully-treated-with-crispr/>. 6 pages.
Mullin, CRISPR eliminated symptoms of genetic disease in 2 patients. One Zero. Nov. 20, 2019. 5 pages.
Parsons, Vertex reveals promising data from first CRISPR-treated patients. PMLive. Nov. 20, 2020. Retrieved from: <http://www.pmlive.com/pharma_news/vertex_reveals_promising_data_from_first_crispr-treated_patients_1317564>. 2 pages.
Stein et al., Compilation of Press Releases. Vertex, CRISPR Therapeutics. Nov. 19, 2019. 40 pages.
Stein, A Year in, 1st Patient to Get Gene Editing for Sickle Cell Disease Is Thriving. NPR. Jun. 23, 2020. Retrieved from: <https://www.npr.org/sections/health-shots/2020/06/23/877543610/a-year-in-1st-patient-to-get-gene-editing-for-sickle-cell-disease-is-thriving>. 26 pages.
Zipkin, CRISPR's "magnificent moment" in the clinic. Nat Biotechnol. Dec. 6, 2019. 4 pages.
U.S. Appl. No. 16/094,408, filed Oct. 17, 2018, Cowan et al.
U.S. Appl. No. 16/356,373, filed Mar. 18, 2019, Cowan et al.
PCT/IB2017/000577, Jul. 25, 2017, Invitation to Pay Additional Fees.
PCT/IB2017/000577, Oct. 25, 2017, International Search Report and Written Opinion.
PCT/IB2017/000577, Nov. 1, 2018, International Preliminary Report on Patentability.
PCT/US2018/063973, Mar. 11, 2019, International Search Report and Written Opinion.
International Preliminary Report on Patentability dated Aug. 20, 2020 for International Application No. PCT/IB2019/000114.
Hendel et al., Chemically modified guide RNAs enhance CRISPR-Cas genome editing in human primary cells. Nat Biotechnol. Sep. 1, 2015;33(9):985-9. Epub Jun. 29, 2015. Author manuscript provided, available in PMC Sep. 1, 2016:14 pages, doi: 10.1038/nbt.3290.
Young, Gene therapy cures patient with sickle cell disease. Article Image. The Sunday Times. Dec. 1, 2019. Accessed Jun. 2020. 1 page.
PCT/IB2019/000114, Aug. 20, 2020, International Preliminary Report on Patentability.
Zhang et al., Optimization of genome editing through CRISPR-Cas9 engineering. Bioengineered. Apr. 2016;7(3):166-74. doi: 10.1080/21655979.2016.1189039.

\* cited by examiner

* 1 donor contaminated

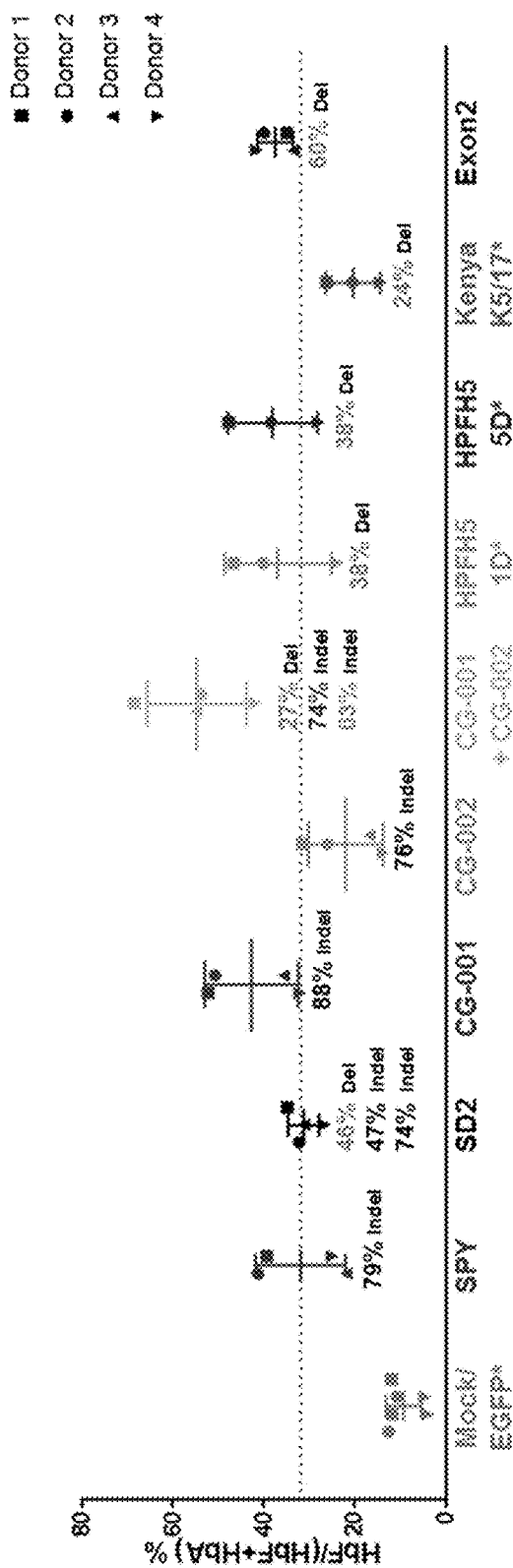

Cell growth and viability assessed during differentiation

* 1 donor contaminated

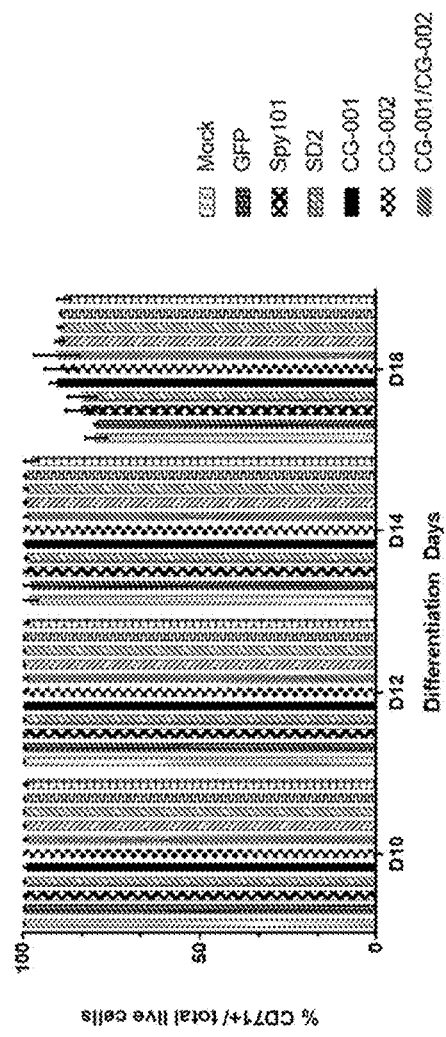
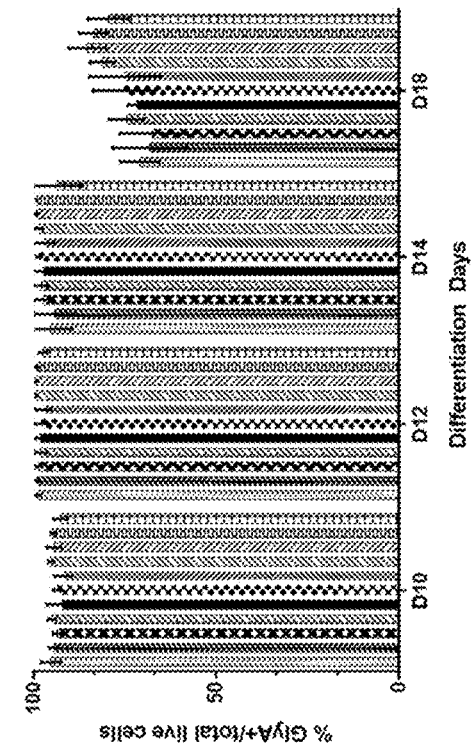
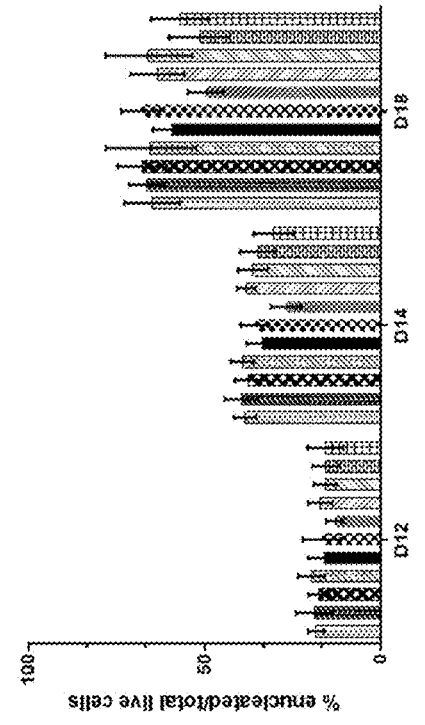
FIG. 8A
FIG. 8B
FIG. 8D
Erythroid markers and enucleation during differentiation

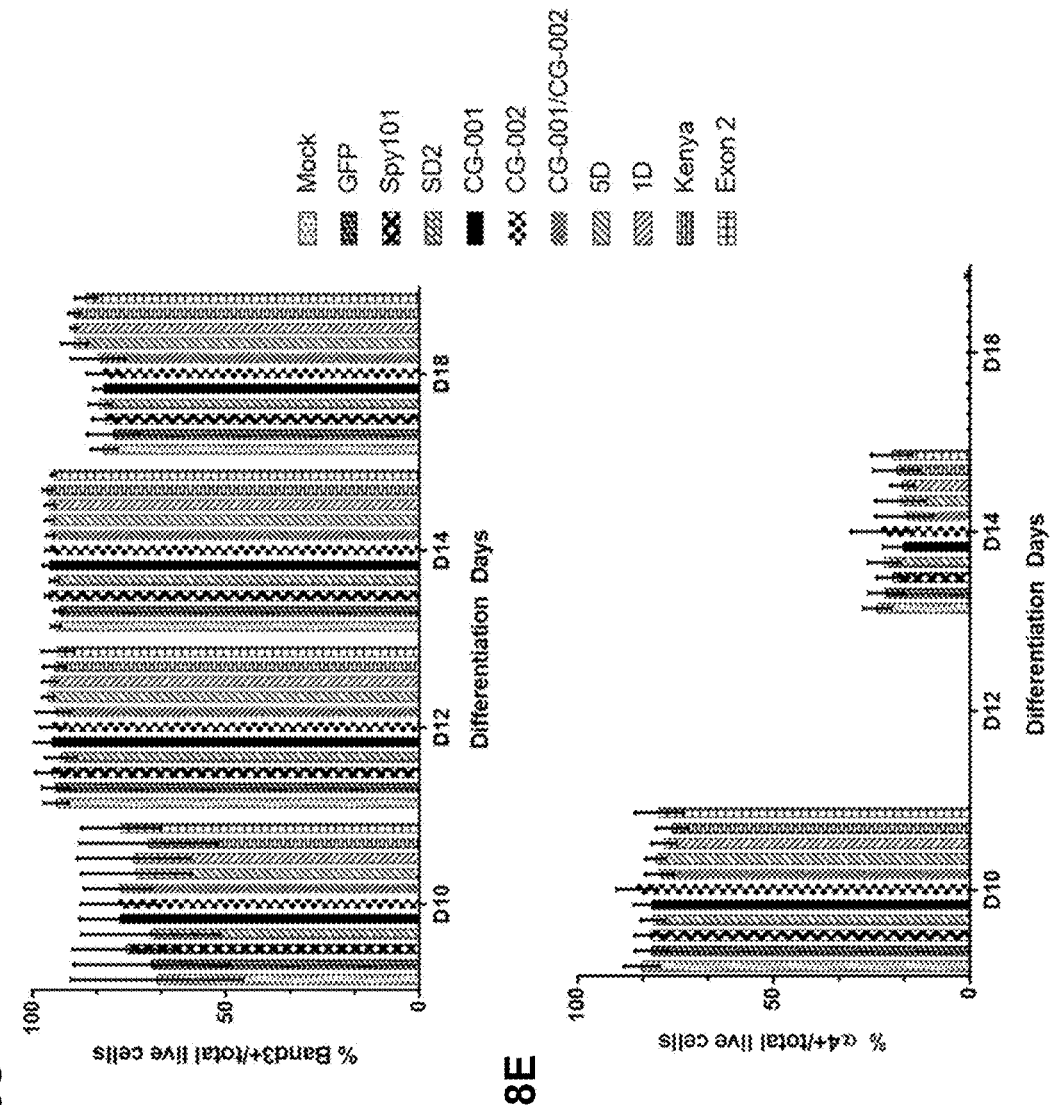

FIG. 14

| Sample Type | NSG<sup>cKit</sup> (100 cGy) | Input | BM (16wk) |
|---|---|---|---|
| % Total Indel Edits (Allele Frequency) | | 97% (n=1) | 95 ± 8% (n=8) |

MATERIALS AND METHODS FOR TREATMENT OF HEMOGLOBINOPATHIES

CROSS-REFERENCE TO RELATED APPLICATIONS

The present application claims priority to U.S. Provisional Application No. 62/626,423, filed Feb. 5, 2018, the contents of which are incorporated by reference herein in their entirety.

FIELD

The present application provides materials and methods for treating patients with hemoglobinopathies, both ex vivo and in vivo. In addition, the present application provides materials and methods for creating permanent changes to the genome that can result in at least one deletion, insertion, modulation, or inactivation of a transcriptional control sequence of a B-cell lymphoma 11A (BCL11A) gene in a cell by genome editing.

INCORPORATION BY REFERENCE OF SEQUENCE LISTING

This application contains a Sequence Listing in computer readable form (filename: C1542.70033WO00-SEQ; 5.6 kb in size; created Feb. 4, 2019), which is incorporated herein by reference in its entirety and forms part of the disclosure.

BACKGROUND

Hemoglobinopathies include anemias of genetic origin, which result in decreased production and/or increased destruction of red blood cells. These disorders also include genetic defects, which result in the production of abnormal hemoglobins with an associated inability to maintain oxygen concentration. Many of these disorders are referred to as 0-hemoglobinopathies because of their failure to produce normal β-globin protein in sufficient amounts or failure to produce normal β-globin protein entirely. For example, 0-thalassemias result from a partial or complete defect in the expression of the β-globin gene, leading to deficient or absent adult hemogloblin (HbA). Sickle cell anemia results from a point mutation in the β-globin structural gene, leading to the production of an abnormal hemoglobin (HbS). Hemoglobinopathies result in a reduction in the oxygen carrying capacity of the blood, which can lead to symptoms such as weariness, dizziness, and shortness of breath, particularly when exercising.

For patients diagnosed with a hemoglobinopathy, currently only a few symptomatic treatments are available, such as a blood transfusion, to increase blood oxygen levels.

Despite efforts from researchers and medical professionals worldwide who have been trying to address hemoglobinopathies, there still remains a critical need for developing safe and effective treatments for hemoglobinopathies.

SUMMARY

The present disclosure presents an approach to address the genetic basis of hemoglobinopathies. By using genome engineering tools to create permanent changes to the genome that can result in at least one deletion, insertion, modulation, or inactivation of a transcriptional control sequence of the BCL11A gene with a single treatment, the resulting therapy may ameliorate the effects of hemoglobinopathies.

In some aspects, provided herein are methods for editing a B-cell lymphoma 11A (BCL11A) gene in a human cell. In some embodiments, the method comprises introducing into the human cell one or more deoxyribonucleic acid (DNA) endonucleases and one or more single-molecule guide RNA (sgRNAs) to effect one or more single-strand breaks (SSBs) or double-strand breaks (DSBs), within or near the BCL11A gene or other DNA sequence that encodes a regulatory element of the BCL11A gene, that results in at least one of a permanent insertion, deletion, modulation, and an inactivation of a transcriptional control sequence of the BCL11A gene. In some embodiments, the one or more sgRNAs comprises the nucleic acid sequence of SEQ ID NO: 11 or SEQ ID NO: 12. In some embodiments, the one or more sgRNAs comprises the nucleic acid sequence of SEQ ID NO: 11. In some embodiments, the one or more sgRNAs comprises the nucleic acid sequence of SEQ ID NO: 12. In some embodiments, the one or more sgRNAs comprises the nucleic acid sequence of SEQ ID NO: 11 and SEQ ID NO: 12.

In some embodiments, the one or more DNA endonucleases for use in the methods described herein may comprise a Cas9 endonuclease. In some embodiments, one or more polynucleotides encoding the one or more DNA endonucleases (e.g., a Cas9 endonuclease) are introduced into the human cell. In some embodiments, one or more ribonucleic acids (RNAs) encoding the one or more DNA endonucleases (e.g., a Cas9 endonuclease) are introduced into the human cell. In some embodiments, the one or more polynucleotides encoding the one or more DNA endonucleases or the one or more RNAs encoding the one or more DNA endonucleases are one or more modified polynucleotides or one or more modified RNAs. In some embodiments, the one or more DNA endonucleases may each comprise, at the N-terminus, the C-terminus, or both the N-terminus and C-terminus, one or more nuclear localization signals (NLSs), optionally wherein the one or more NLS is a SV40 NLS. In some embodiments, the one or more DNA endonucleases each comprise two NLSs, one NLS located at the N-terminus and the second NLS located at the C-terminus.

In some embodiments, the one or more sgRNAs for use in the methods described herein may be one or more modified sgRNAs. In some embodiments, the one or more modified sgRNAs comprises three 2'-O-methyl-phosphorothioate residues at or near each of its 5' and 3' ends.

In some embodiments, the one or more DNA endonucleases and the one or more sgRNAs may both be introduced into the human cell. In some embodiments, the one or more DNA endonucleases is pre-complexed with the one or more sgRNAs to form one or more ribonucleoproteins (RNPs), optionally wherein the weight ratio of sgRNA to DNA endonuclease in the RNP is 1:1. In some embodiments, the sgRNA comprises the nucleic acid sequence of SEQ ID NO: 11, the DNA endonuclease is a *S. pyogenes* Cas9 comprising a N-terminus SV40 NLS and a C-terminus SV40 NLS, wherein the weight ratio of sgRNA to DNA endonuclease is 1:1. In some embodiments, the sgRNA comprises the nucleic acid sequence of SEQ ID NO: 12, the DNA endonuclease is a *S. pyogenes* Cas9 comprising a N-terminus SV40 NLS and a C-terminus SV40 NLS, wherein the weight ratio of sgRNA to DNA endonuclease is 1:1.

In some embodiments, the one or more sgRNAs comprises a first sgRNA and a second sgRNA that is different from the first sgRNA, wherein the first or second sgRNA comprises the nucleic acid sequence of SEQ ID NO: 11 or 12. In some embodiments, the first sgRNA comprises the nucleic acid sequence of SEQ ID NO: 11 or 12 and the second sgRNA comprises the nucleic acid sequence of SEQ ID NO: 13. In some embodiments, the first sgRNA comprises the nucleic acid sequence of SEQ ID NO: 11 and the second sgRNA comprises the nucleic acid sequence of SEQ ID NO: 13. In some embodiments, the first sgRNA comprises the nucleic acid sequence of SEQ ID NO: 11 and the second sgRNA comprises the nucleic acid sequence of SEQ ID NO: 12.

In some embodiments, the first sgRNA comprises the nucleic acid sequence of SEQ ID NO: 11, the Cas9 endonuclease is a *S. pyogenes* Cas9 comprising a N-terminus SV40 NLS and a C-terminus SV40 NLS, wherein the weight ratio of sgRNA to Cas9 endonuclease is 1:1.

In some embodiments, the first sgRNA comprises the nucleic acid sequence of SEQ ID NO: 12, the Cas9 endonuclease is a *S. pyogenes* Cas9 comprising a N-terminus SV40 NLS and a C-terminus SV40 NLS, wherein the weight ratio of sgRNA to Cas9 endonuclease is 1:1.

In some embodiments of any of the methods described herein, a Cas9 mRNA and one or more sgRNA may be each formulated into separate lipid nanoparticles or may be co-formulated into a lipid nanoparticle. In some embodiments of any of the methods described herein, a Cas9 mRNA may be formulated into a lipid nanoparticle, and one or more sgRNA may be delivered to the cell by an adeno-associated virus (AAV) vector. In some embodiments of any of the methods described herein, a Cas9 mRNA may be formulated into a lipid nanoparticle, and one or more sgRNA may be delivered to the cell by electroporation.

In some embodiments of any of the methods described herein, the one or more RNP is delivered to the cell by electroporation.

Other aspects of the disclosure include an ex vivo method for treating a patient with a hemoglobinopathy, the method comprising (a) editing within or near a B-cell lymphoma 11A (BCL11A) gene or other DNA sequence that encodes a regulatory element of the BCL11A gene of an induced pluripotent stem cell (iPSC) or a mesenchymal stem cell; (b) differentiating the genome-edited iPSC or mesenchymal stem cell into a hematopoietic progenitor cell; and (c) implanting the hematopoietic progenitor cell into the patient, wherein step (a) is performed by a method described herein for purposes of editing a B-cell lymphoma 11A (BCL11A) gene in a human cell, including any one or more of the above-mentioned embodiments.

In some embodiments, an iPSC may be created by a process comprising isolating a somatic cell from the patient; and introducing a set of pluripotency-associated genes into the somatic cell to induce the somatic cell to become the iPSC. In some embodiments, the somatic cell is a fibroblast. In some embodiments, the set of pluripotency-associated genes is one or more of the genes selected from the group consisting of: OCT4, SOX2, KLF4, Lin28, NANOG and cMYC. In some embodiments, differentiation of an iPSC comprises one or more of the following to differentiate the genome-edited iPSC into a hematopoietic progenitor cell: treatment with a combination of small molecules, delivery of master transcription factors, delivery of mRNA encoding master transcription factors, or delivery of mRNA encoding transcription factors.

In some embodiments, the mesenchymal stem cell may be isolated from a patient's bone marrow or peripheral blood, optionally wherein the isolating step comprises aspiration of bone marrow and isolation of mesenchymal cells using density gradient centrifugation media. In some embodiments, differentiation of the mesenchymal stem cell comprises one or more of the following to differentiate the genome-edited mesenchymal stem cell into a hematopoietic progenitor cell: treatment with a combination of small molecules, delivery of master transcription factors, delivery of mRNA encoding master transcription factors, or delivery of mRNA encoding transcription factors.

In some embodiments, implanting the hematopoietic progenitor cell into a patient may comprise implanting the hematopoietic progenitor cell into the patient by transplantation, local injection, systemic infusion, or combinations thereof.

Other aspects of the disclosure relate to an ex vivo method for treating a patient with a hemoglobinopathy, the method comprising (a) editing within or near a B-cell lymphoma 11A (BCL11A) gene or other DNA sequence that encodes a regulatory element of the BCL11A gene of a hematopoietic progenitor cell; and (b) implanting the genome-edited hematopoietic progenitor cell into the patient, wherein step (a) is performed by a method described herein for purposes of editing a B-cell lymphoma 11A (BCL11A) gene in a human cell, including any one or more of the above-mentioned embodiments.

In some embodiments, the ex vivo method further comprises isolating the hematopoietic progenitor cell from the patient, optionally wherein the method further comprises treating the patient with granulocyte colony stimulating factor (GCSF) prior to the isolating step. In some embodiments, GCSF is used in combination with Plerixaflor (1,1'-(1,4-phenylenebismethylene)bis(1,4,8,11-tetraazacyclotetradecane)). In some embodiments, an isolating step comprises isolating CD34+ cells.

In some embodiments, an ex vivo method involves an implanting step that comprises implanting the genome-edited hematopoietic progenitor cell into the patient by transplantation, local injection, systemic infusion, or combinations thereof.

In some embodiments, the human cell for use in ex vivo methods is a bone marrow cell, a hematopoietic progenitor cell, or a CD34+ cell.

Other aspects of the disclosure provide an in vivo method for treating a patient with a hemoglobinopathy, the method comprising (a) editing a B-cell lymphoma 11A (BCL11A) gene in a cell of the patient, wherein step (a) is performed by a method described herein for purposes of editing a B-cell lymphoma 11A (BCL11A) gene in a human cell, including any one or more of the above-mentioned embodiments.

In some embodiments of any of the methods provided herein, the hemoglobinopathy is selected from a group consisting of sickle cell anemia and thalassemia ($\alpha$, $\beta$, $\delta$, $\gamma$, and combinations thereof).

In some embodiments of any of the methods provided herein, the editing of the BCL11A gene (e.g., at least one of a permanent insertion, deletion, modulation, and an inactivation of a transcriptional control sequence of the BCL11A gene) reduces B-cell lymphoma 11A (BCL11A) gene expression.

Further aspects of the disclosure relate to a single-molecule guide RNA (sgRNA) comprising the nucleic acid sequence of SEQ ID NO: 11 or SEQ ID NO:12. In some embodiments, a sgRNA comprises the nucleic acid sequence of SEQ ID NO: 11. In some embodiments, a sgRNA comprises the nucleic acid sequence of SEQ ID NO: 12. In some embodiments, the sgRNA is modified and comprises or consists of the modified nucleic acid sequence of SEQ ID NO: 11. In some embodiments, the sgRNA is modified and comprises or consists of the modified nucleic acid sequence of SEQ ID NO: 12.

Additional aspects of the disclosure relate to kits comprising at least two of the following guide RNAs (gRNAs):

(i) a first gRNA comprising a spacer sequence of SEQ ID NO: 6; optionally wherein any or all T's in the sequence is/are replaced with U's (ii) a second gRNA comprising a spacer sequence of SEQ ID NO: 7, optionally wherein any or all T's in the sequence is/are replaced with U's; and (iii) a third gRNA comprising a spacer sequence of SEQ ID NO: 14.

In some embodiments, the kit may at least one modified gRNA. In some embodiments of the kit, (i), (ii), and/or (iii) is a modified gRNA. In some embodiments, the kit comprises at least one sgRNA. In some embodiments of the kit, (i), (ii), and/or (iii) is/are a sgRNA.

In some embodiments, the kit comprises a first gRNA which is a sgRNA comprising the nucleotide sequence of SEQ ID NO:11, a second gRNA which is a sgRNA comprising the nucleotide sequence of SEQ ID NO:12, and/or a third gRNA which is a sgRNA comprising the nucleotide sequence of SEQ ID NO:13.

In some embodiments, the kit comprises at least (i) and (ii), or at least (i) and (iii). In some embodiments, a kit comprises at least (i) and (iii).

In some embodiments, the gRNAs in the kit are formulated in one composition.

Further aspects of the disclosure provide a genetically engineered cell. In some embodiments, the genetically engineered cells is produced or obtainable by a method described herein for purposes of editing a B-cell lymphoma 11A (BCL11A) gene in a human cell, including any one or more of the above-mentioned embodiments.

In some embodiments, the genetically engineered cell comprises a genetic mutation which is one of a permanent insertion, deletion, modulation, and an inactivation of a transcriptional control sequence of a BCL11A gene, wherein the genetic mutation occurs at one or more sites targeted by one or more sgRNAs, at least one of which comprises the nucleic acid sequence of SEQ ID NO: 11 or SEQ ID NO: 12.

In some embodiments, the genetically engineered cell comprises a genetic mutation which is one of a permanent insertion, deletion, modulation, and an inactivation of a transcriptional control sequence of a BCL11A gene, wherein the genetic mutation occurs at one or more sites targeted by a first sgRNA and a second sgRNA that is different than the first sgRNA, wherein the first sgRNA comprises the nucleic acid sequence of SEQ ID NO: 11, SEQ ID NO: 12 or SEQ ID NO: 13, and wherein the second sgRNA comprises the nucleic acid sequence of SEQ ID NO: 11, SEQ ID NO: 12 or SEQ ID NO: 13. In some embodiments, the first sgRNA comprises the nucleic acid sequence of SEQ ID NO: 11 and the second sgRNA comprises the nucleic acid sequence of SEQ ID NO: 13. In some embodiments, the first sgRNA comprises the nucleic acid sequence of SEQ ID NO: 11 and the second sgRNA comprises the nucleic acid sequence of SEQ ID NO: 12.

In some embodiments, genetically engineered cell described herein may be a CD34+ human cell, optionally, a CD34+ human hematopoietic stem and progenitor cell.

In some embodiments, a genetically engineered cell described herein exhibits a HbF mean percentage of HbF/(HbF+HbA) protein levels of at least 10%, optionally at least 15%, further optionally at least 20%, further optionally at least 25%, further optionally at least 30%, further optionally at least 40%, further optionally at least 50%.

Further aspects of the disclosure relate to a population of genetically engineered cells, such as a population of genetically engineered cells of any one or more of the above-mentioned embodiments. In some embodiments, at least 70% of the population of genetically engineered cells maintain multi-lineage potential for at least sixteen weeks after administration of the population to a subject. In some embodiments, the population of genetically engineered cells exhibits a mean allele editing frequency of 70% to 90%. In some embodiments, the population of genetically engineered cells exhibits a HbF mean percentage of HbF/(HbF+HbA) protein levels of at least 10%, optionally at least 15%, further optionally at least 20%, further optionally at least 25%, further optionally at least 30%, further optionally at least 40%, further optionally at least 50%.

In some embodiments, the population of genetically engineered cells exhibits an off-target indel rate of less than 1%. In some embodiments, the population of genetically engineered cells comprises cells having at least two (e.g., two, three, four, five, ten, fifteen, twenty or more) different genetic mutations (e.g., at least two, such as two, three, four, five, ten, fifteen, twenty or more, cells having different genetic mutations from one another).

Additional aspects of the disclosure provide methods for treating a patient with a hemoglobinopathy (e.g., sickle cell anemia and thalassemia ($\alpha$, $\beta$, $\delta$, $\gamma$, and combinations thereof)), comprising administering to a subject in need thereof an effective amount of a population of genetically engineered cells, such as any one or more of the above-mentioned embodiments.

Some aspects of the disclosure relate to compositions comprising a genetically engineered cell, such as any one or more of the above-mentioned embodiments, or a population of genetically engineered cells, such as any one or more of the above-mentioned embodiments, for use in the treatment of hemoglobinopathy (e.g., sickle cell anemia and thalassemia ($\alpha$, $\beta$, $\delta$, $\gamma$, and combinations thereof)).

Also provided herein is a method for editing a B-cell lymphoma 11A (BCL11A) gene in a human cell by genome editing. The method can comprise: introducing into the human cell one or more deoxyribonucleic acid (DNA) endonucleases to effect one or more single-strand breaks (SSBs) or double-strand breaks (DSBs), within or near the BCL11A gene or other DNA sequence that encodes a regulatory element of the BCL11A gene. The one or more SSBs or DSBs can result in at least one of a permanent insertion, deletion, modulation, and an inactivation of a transcriptional control sequence of the BCL11A gene.

The transcriptional control sequence can be located within a second intron of the BCL11A gene. The transcriptional control sequence can be located within one or more of: a +55 DNase I hypersensitive site (DHS) of the BCL11A gene, a +58 DHS of the BCL11A gene, and a +62 DHS of the BCL11A gene.

Also provided herein is an ex vivo method for treating a patient with a hemoglobinopathy. The method can comprise: editing within or near a BCL11A gene or other DNA sequence that encodes a regulatory element of the BCL11A gene of an induced pluripotent stem cell (iPSC); differentiating the genome-edited iPSC into a hematopoietic progenitor cell; and implanting the hematopoietic progenitor cell into the patient.

The ex vivo method can further comprise: creating the iPSC. The creating step can comprise: isolating a somatic cell from the patient; and introducing a set of pluripotency-associated genes into the somatic cell to induce the somatic cell to become the iPSC. The somatic cell can be a fibroblast. The set of pluripotency-associated genes can be one or more of the genes selected from the group consisting of: OCT4, SOX2, KLF4, Lin28, NANOG and cMYC.

The editing step can comprise: introducing into the iPSC one or more DNA endonucleases to effect one or more SSBs or DSBs within or near the BCL11A gene or other DNA sequence that encodes a regulatory element of the BCL11A gene that results in at least one of a permanent insertion, deletion, modulation, and an inactivation of a transcriptional control sequence of the BCL11A gene. The transcriptional control sequence can be located within a second intron of the BCL11A gene. The transcriptional control sequence can be located within one or more of: a +55 DHS of the BCL11A gene, a +58 DHS of the BCL11A gene, and a +62 DHS of the BCL11A gene.

The differentiating step can comprise one or more of the following to differentiate the genome-edited iPSC into a hematopoietic progenitor cell: treatment with a combination of small molecules, delivery of master transcription factors, delivery of mRNA encoding master transcription factors, or delivery of mRNA encoding transcription factors.

The implanting step can comprise implanting the hematopoietic progenitor cell into the patient by transplantation, local injection, systemic infusion, or combinations thereof.

Also provided herein is an ex vivo method for treating a patient with a hemoglobinopathy. The method can comprise: editing within or near a BCL11A gene or other DNA sequence that encodes a regulatory element of the BCL11A gene of a mesenchymal stem cell; differentiating the genome-edited mesenchymal stem cell into a hematopoietic progenitor cell; and implanting the hematopoietic progenitor cell into the patient.

The ex vivo method can further comprise: isolating the mesenchymal stem cell from the patient. The mesenchymal stem cell can be isolated from the patient's bone marrow or peripheral blood. The isolating step can comprise: aspiration of bone marrow and isolation of mesenchymal cells using density gradient centrifugation media.

The editing step can comprise: introducing into the mesenchymal stem cell one or more DNA endonucleases to effect one or more SSBs or DSBs within or near the BCL11A gene or other DNA sequence that encodes a regulatory element of the BCL11A gene that can result in at least one of a permanent insertion, deletion, modulation, and an inactivation of a transcriptional control sequence of the BCL11A gene. The transcriptional control sequence can be located within a second intron of the BCL11A gene. The transcriptional control sequence can be located within one or more of: a +55 DHS of the BCL11A gene, a +58 DHS of the BCL11A gene, and a +62 DHS of the BCL11A gene.

The differentiating step can comprise one or more of the following to differentiate the genome-edited mesenchymal stem cell into a hematopoietic progenitor cell: treatment with a combination of small molecules, delivery of master transcription factors, delivery of mRNA encoding master transcription factors, or delivery of mRNA encoding transcription factors.

The implanting step can comprise implanting the hematopoietic progenitor cell into the patient by transplantation, local injection, systemic infusion, or combinations thereof.

Also provided herein is an ex vivo method for treating a patient with a hemoglobinopathy. The method can comprise: editing within or near a BCL11A gene or other DNA sequence that encodes a regulatory element of the BCL11A gene of a hematopoietic progenitor cell; and implanting the genome-edited hematopoietic progenitor cell into the patient.

The ex vivo method can further comprise: isolating the hematopoietic progenitor cell from the patient. The ex vivo method can further comprise: treating the patient with granulocyte colony stimulating factor (GCSF) prior to the isolating step. The treating step can be performed in combination with 1,1'-(1,4-phenylenebismethylene)bis(1,4,8,11-tetraazacyclotetradecane). The isolating step can comprise isolating CD34+ cells.

The editing step can comprise: introducing into the hematopoietic progenitor cell one or more DNA endonucleases to effect one or more SSBs or DSBs within or near the BCL11A gene or other DNA sequence that encodes a regulatory element of the BCL11A gene that can result in at least one of a permanent insertion, deletion, modulation, and an inactivation of a transcriptional control sequence of the BCL11A gene. The transcriptional control sequence can be located within a second intron of the BCL11A gene. The transcriptional control sequence can be located within one or more of: a +55 DHS of the BCL11A gene, a +58 DHS of the BCL11A gene, and a +62 DHS of the BCL11A gene.

The implanting step can comprise implanting the genome-edited hematopoietic progenitor cell into the patient by transplantation, local injection, systemic infusion, or combinations thereof.

Also provided herein is an in vivo method for treating a patient with a hemoglobinopathy. The method can comprise: editing a BCL11A gene in a cell of the patient.

The editing step can comprise introducing into the cell one or more DNA endonucleases to effect one or more SSBs or DSBs within or near the BCL11A gene or other DNA sequence that encodes a regulatory element of the BCL11A gene that can result in at least one of a permanent insertion, deletion, modulation, and an inactivation of a transcriptional control sequence of the BCL11A gene. The transcriptional control sequence can be located within a second intron of the BCL11A gene. The transcriptional control sequence can be located within one or more of: a +55 DHS of the BCL11A gene, a +58 DHS of the BCL11A gene, and a +62 DHS of the BCL11A gene. The cell can be a bone marrow cell, a hematopoietic progenitor cell, or a CD34+ cell.

The one or more DNA endonucleases can be a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized versions thereof, or modified versions thereof, and combinations thereof. The method can comprise introducing into the cell one or more polynucleotides encoding the one or more DNA endonucleases. The method can comprise introducing into the cell one or more RNAs encoding the one or more DNA endonucleases. The one or more polynucleotides or one or more RNAs can be one or more modified polynucleotides or one or more modified RNAs. The one or more DNA endonuclease can be one or more proteins or polypeptides. The one or more proteins or polypeptides can be flanked at the N-terminus, the C-terminus, or both the N-terminus and C-terminus by one or more NLSs. The one or more proteins or polypeptides can be flanked by two NLSs, one NLS located at the N-terminus and the second NLS located at the C-terminus. The one or more NLSs can be a SV40 NLS.

The methods can further comprise introducing into the cell one or more guide ribonucleic acids (gRNAs). The one or more gRNAs can be single-molecule guide RNA (sgRNAs). The one or more gRNAs or one or more sgRNAs can be one or more modified gRNAs or one or more modified sgRNAs. The one or more modified sgRNAs can comprise three 2'-O-methyl-phosphorothioate residues at or near each of its 5' and 3' ends. The modified sgRNA can be the nucleic acid sequence of SEQ ID NO: 11. The modified sgRNA can be the nucleic acid sequence of SEQ ID NO: 12. The one or more gRNAs or one or more sgRNAs can target a GATA1 site. The one or more gRNAs or one or more sgRNAs can target an ELF1 site.

The one or more DNA endonucleases can be pre-complexed with one or more gRNAs or one or more sgRNAs to form one or more ribonucleoproteins (RNPs). The weight ratio of sgRNA to DNA endonuclease in the RNP can be 1:1. The sgRNA can comprise the nucleic acid sequence of SEQ ID NO: 11, the DNA endonuclease can be a *S. pyogenes* Cas9 comprising a N-terminus SV40 NLS and a C-terminus SV40 NLS, and the weight ratio of sgRNA to DNA endonuclease can be 1:1. The sgRNA can comprise the nucleic acid sequence of SEQ ID NO: 12, the DNA endonuclease can be a *S. pyogenes* Cas9 comprising a N-terminus SV40 NLS and a C-terminus SV40 NLS, and the weight ratio of sgRNA to DNA endonuclease can be 1:1.

The methods can further comprise: introducing into the cell one gRNA; wherein the one or more DNA endonucleases can be one or more Cas9 or Cpf1 endonucleases that effect one SSB or DSB at a locus within or near the BCL11A gene or other DNA sequence that encodes a regulatory element of the BCL11A gene, and wherein the gRNA can comprise a spacer sequence that is complementary to a segment of the locus.

The methods can further comprise: introducing into the cell one or more gRNAs; wherein the one or more DNA endonucleases can be one or more Cas9 or Cpf1 endonucleases that can effect or create a pair of SSBs or DSBs, the first at a 5' locus and the second at a 3' locus, within or near the BCL11A gene or other DNA sequence that encodes a regulatory element of the BCL11A gene, and wherein the first guide RNA can comprise a spacer sequence that can be complementary to a segment of the 5' locus and the second guide RNA can comprise a spacer sequence that is complementary to a segment of the 3' locus.

The one or more gRNAs can be one or more sgRNAs. The one or more gRNAs or one or more sgRNAs can be one or more modified gRNAs or one or more modified sgRNAs. The one or more modified sgRNA can comprise three 2'-O-methyl-phosphorothioate residues at or near each of its 5' and 3' ends. The one or more modified sgRNA can be the nucleic acid sequence of SEQ ID NO: 11. The one or more modified sgRNA can be the nucleic acid sequence of SEQ ID NO: 12. The one or more gRNAs or one or more sgRNAs can target a GATA1 site. The one or more gRNAs or one or more sgRNAs can target an ELF1 site.

The one or more Cas9 endonucleases can be pre-complexed with one or more gRNAs or one or more sgRNAs to form one or more ribonucleoproteins (RNPs). The one or more Cas9 endonucleases can be flanked at the N-terminus, the C-terminus, or both the N-terminus and C-terminus by one or more nuclear localization signals (NLSs). The one or more Cas9 endonucleases can be flanked by two NLSs, one NLS located at the N-terminus and the second NLS located at the C-terminus. The one or more NLSs can be a SV40 NLS.

The weight ratio of sgRNA to Cas9 endonuclease in the RNP can be 1:1. The one or more sgRNA can comprise the nucleic acid sequence of SEQ ID NO: 11, the Cas9 endonuclease can be a *S. pyogenes* Cas9 comprising a N-terminus SV40 NLS and a C-terminus SV40 NLS, and the weight ratio of sgRNA to Cas9 endonuclease can be 1:1. The one or more sgRNA can comprise the nucleic acid sequence of SEQ ID NO: 12, the Cas9 endonuclease can be a *S. pyogenes* Cas9 comprising a N-terminus SV40 NLS and a C-terminus SV40 NLS, and the weight ratio of sgRNA to Cas9 endonuclease can be 1:1.

The methods can further comprise: introducing into the cell two guide ribonucleic acid (gRNAs); wherein the one or more DNA endonucleases can be one or more Cas9 or Cpf1 endonucleases that can effect a pair of DSBs, the first at a 5' DSB locus and the second at a 3' DSB locus, within or near the BCL11A gene or other DNA sequence that encodes a regulatory element of the BCL11A gene that causes a deletion of the chromosomal DNA between the 5' DSB locus and the 3' DSB locus that can result in a permanent deletion of the chromosomal DNA between the 5'DSB locus and the 3' DSB locus; and the first guide RNA can comprise a spacer sequence that is complementary to a segment of the 5' DSB locus, and the second guide RNA can comprise a spacer sequence that is complementary to a segment of the 3' DSB locus.

The two gRNAs can be two single-molecule guide RNA (sgRNAs). The two gRNAs or two sgRNAs can be two modified gRNAs or two modified sgRNAs. The two modified sgRNAs can comprise three 2'-O-methyl-phosphorothioate residues at or near each of its 5' and 3' ends. One modified sgRNA can be the nucleic acid sequence of SEQ ID NO: 11. One modified sgRNA can be the nucleic acid sequence of SEQ ID NO: 12. The two gRNAs or two sgRNAs can target a GATA1 site. The two gRNAs or two sgRNAs can target an ELF1 site.

The one or more Cas9 endonucleases can be pre-complexed with one or two gRNAs or one or two sgRNAs to form one or more RNPs. The one or more Cas9 endonuclease can be flanked at the N-terminus, the C-terminus, or both the N-terminus and C-terminus by one or more NLSs. The one or more Cas9 endonucleases can be flanked by two NLSs, one NLS located at the N-terminus and the second NLS located at the C-terminus. The one or more NLSs can be a SV40 NLS. The weight ratio of sgRNA to Cas9 endonuclease in the RNP can be 1:1. One sgRNA can comprise the nucleic acid sequence of SEQ ID NO: 11, the Cas9 endonuclease can be a *S. pyogenes* Cas9 comprising a N-terminus SV40 NLS and a C-terminus SV40 NLS, and the weight ratio of sgRNA to Cas9 endonuclease can be 1:1. One sgRNA can comprise the nucleic acid sequence of SEQ ID NO: 12, the Cas9 endonuclease can be a *S. pyogenes* Cas9 comprising a N-terminus SV40 NLS and a C-terminus SV40 NLS, and the weight ratio of sgRNA to Cas9 endonuclease can be 1:1.

The one or more SSB, DSB, or locus can be located within a second intron of the BCL11A gene. The one or more SSB, DSB, or locus can be located within a +55 DHS of the BCL11A gene. The one or more SSB, DSB, or locus can be located within a +58 DHS of the BCL11A gene. The one or more SSB, DSB, or locus can be located within a +62 DHS of the BCL11A gene.

The gRNA can comprise a spacer sequence that is complementary to one or more of: a +55 DHS of the BCL11A gene, a +58 DHS of the BCL11A gene, and a +62 DHS of the BCL11A gene.

The two gRNAs can comprise a spacer sequence that is complementary to one or more of: a +55 DHS of the BCL11A gene, a +58 DHS of the BCL11A gene, and a +62 DHS of the BCL11A gene.

The deletion can comprise a +55 DHS of the BCL11A gene, or a fragment thereof. The deletion can comprise a +58 DHS of the BCL11A gene, or a fragment thereof. The deletion can comprise a +62 DHS of the BCL11A gene, or a fragment thereof. The deletion can comprise a +55 DHS of the BCL11A gene and a +58 DHS of the BCL11A gene, or fragments thereof. The deletion can comprise a +55 DHS of the BCL11A gene and a +62 DHS of the BCL11A gene, or fragments thereof. The deletion can comprise a +58 DHS of the BCL11A gene and a +62 DHS of the BCL11A gene, or fragments thereof. The deletion can be 10 kb or less. The deletion can be 3.1 kb.

The Cas9 or Cpf1 mRNA, and gRNA can be either each formulated into separate lipid nanoparticles or all co-formulated into a lipid nanoparticle. The Cas9 or Cpf1 mRNA can be formulated into a lipid nanoparticle, and the gRNA can be delivered to the cell by an adeno-associated virus (AAV) vector. The Cas9 or Cpf1 mRNA can be formulated into a lipid nanoparticle, and the gRNA can be delivered to the cell by electroporation. The one or more RNP can be delivered to the cell by electroporation.

The BCL11A gene can be located on Chromosome 2: 60,451,167-60,553,567 (Genome Reference Consortium—GRCh38). The hemoglobinopathy can be selected from a group consisting of sickle cell anemia and thalassemia ($\alpha$, $\beta$, $\delta$, $\gamma$, and combinations thereof). Editing the BCL11A gene can reduce BCL11A gene expression.

Also provided herein is one or more gRNAs for editing a BCL11A gene in a cell from a patient with a hemoglobinopathy. The one or more gRNAs can comprise a spacer sequence selected from the group consisting of nucleic acid sequences in any one of SEQ ID NOs: 6-7 of the Sequence Listing.

The one or more gRNAs can be one or more sgRNAs. The one or more gRNAs or one or more sgRNAs can be one or more modified gRNAs or one or more modified sgRNAs. The one or more modified sgRNAs can comprise three 2'-O-methyl-phosphorothioate residues at or near each of its 5' and 3' ends. The one or more modified sgRNAs can comprise the nucleic acid sequence of SEQ ID NO: 11. The one or more modified sgRNAs can comprise the nucleic acid sequence of SEQ ID NO: 12. The one or more gRNAs or sgRNAs can target a GATA1 site. The one or more gRNAs or sgRNAs can target an ELF1 site.

Also provided herein is a sgRNA comprising the nucleic acid sequence of SEQ ID NO: 11.

Also provided herein is a sgRNA comprising the nucleic acid sequence of SEQ ID NO: 12.

Also provided herein is a therapeutic comprising at least one or more gRNAs for editing a BCL11A gene in a cell from a patient with a hemoglobinopathy. The one or more gRNAs can comprise a spacer sequence selected from the group consisting of nucleic acid sequences in any one of SEQ ID NOs: 6-7 of the Sequence Listing. The one or more gRNAs can be one or more sgRNAs. The one or more gRNAs or one or more sgRNAs can be one or more modified gRNAs or one or more modified sgRNAs. The one or more gRNAs can comprise a nucleic acid sequence selected from the group consisting of SEQ ID NOs: 11-12 in the Sequence Listing.

Also provided herein is a therapeutic for treating a patient with a hemoglobinopathy formed by the method comprising: introducing one or more DNA endonucleases; introducing one or more gRNA or one or more sgRNA for editing a BCL11A gene; wherein the one or more gRNAs or sgRNAs comprise a spacer sequence selected from the group consisting of nucleic acid sequences in SEQ ID NOs: 6-7 of the Sequence Listing. The one or more gRNAs can comprise a nucleic acid sequence selected from the group consisting of SEQ ID NOs: 11-12 in the Sequence Listing.

It is understood that the inventions described in this specification are not limited to the examples summarized in this Summary. Various other aspects are described and exemplified herein.

BRIEF DESCRIPTION OF THE DRAWINGS

Various aspects of materials and methods for treatment of hemoglobinopathies disclosed and described in this specification can be better understood by reference to the accompanying figures, in which:

FIG. 2A depicts an example deletion within the three Erythroid-specific DHS using dual gRNAs, CG-001 and CG-002. FIG. 2B depicts an example inversion within the three Erythroid-specific DHS using dual gRNAs, CG-001 and CG-002. FIG. 2C depicts an example Indel within the +55 Erythroid-specific DHS using single gRNA, CG-001, or using dual gRNAs, CG-001 and CG-002, during events when only CG-001 cuts. FIG. 2D depicts an example Indel within the +58 Erythroid-specific DHS using single gRNA, CG-002, or using dual gRNAs, CG-001 and CG-002, during events when only CG-002 cuts. FIG. 2E depicts an example Indel within the +55 Erythroid-specific DHS and a possible Indel within the +58 Erythroid-specific DHS using dual gRNAs, CG-001 and CG-002.

FIG. 4A shows the ratios of $\gamma$-globin to $\alpha$-globin mRNA ($\gamma/\alpha$) measured in erythrocytes differentiated in vitro from human mPB CD34+HSPCs isolated from Donors 1-4 and edited with different gRNAs and Cas9 protein. FIG. 4B shows the ratios of $\gamma$-globin to $\beta$-like globin mRNA ($\gamma/(\gamma+\beta)$) measured in erythrocytes differentiated in vitro from human mPB CD34+HSPCs isolated from Donors 1-4 and edited with different gRNAs and Cas9 protein.

FIG. 5A shows the percentage of HbF measured in erythrocytes differentiated in vitro for 14 days from human mPB CD34+HSPCs isolated from Donors 1-4 and edited with different gRNAs and Cas9 protein. FIG. 5B shows the percentage of HbF measured in erythrocytes differentiated in vitro for 18 days from human mPB CD34+ HSPCs isolated from Donors 1-4 and edited with different gRNAs and Cas9 protein.

FIG. 6 is a summary graph showing the percentage of fetal hemoglobin (HbF) measured in erythrocytes differentiated in vitro for 18 days from human mPB CD34+HSPCs isolated from Donors 1-4 and edited with different gRNAs and Cas9 protein. The percentages below each of the data points indicate editing efficiencies and the type of edit (Indel or Del).

FIG. 7A shows the cell viability at various time-points throughout erythroid differentiation for human mPB CD34+HSPCs electroporated with Cas9 protein and different gRNAs. FIG. 7B shows the cell proliferation at various time-points throughout erythroid differentiation for human mPB CD34+HSPCs electroporated with Cas9 protein and different gRNAs.

FIGS. 8A-8E show percentage of enucleation and erythroid differentiation markers at various time-points throughout erythroid differentiation for human mPB CD34+HSPCs electroporated with Cas9 protein and different gRNAs. FIG. 8A shows the percentage of enucleation at various time-points throughout erythroid differentiation for human mPB CD34+HSPCs electroporated with Cas9 protein and different gRNAs. FIG. 8B shows the erythroid differentiation of human mPB CD34+HSPCs electroporated with different gRNAs and Cas9 protein. Differentiation was determined by measuring the percentage of CD71.

FIG. 8C shows the erythroid differentiation of human mPB CD34+HSPCs electroporated with different gRNAs and Cas9 protein. Differentiation was determined by measuring the percentage of Band3. FIG. 8D shows the erythroid differentiation of human mPB CD34+HSPCs electroporated with different gRNAs and Cas9 protein. Differentiation was determined by measuring the percentage of GlyA. FIG. 8E shows the erythroid differentiation of human mPB CD34+HSPCs electroporated with different gRNAs and Cas9 protein. Differentiation was determined by measuring the percentage of Alpha4.

FIG. 14 shows the total percentage of Indel frequency from input human mPB CD34+HSPCs edited with CG-001 and the Indel frequency from bone marrow of engrafted NSG$^{cKit}$ mice at 16 weeks post-engraftment from FIG. 12. Indel frequency was determined using on-target editing analysis by amplicon next generation sequencing (NGS).

BRIEF DESCRIPTION OF THE SEQUENCE LISTING

Figure 1:
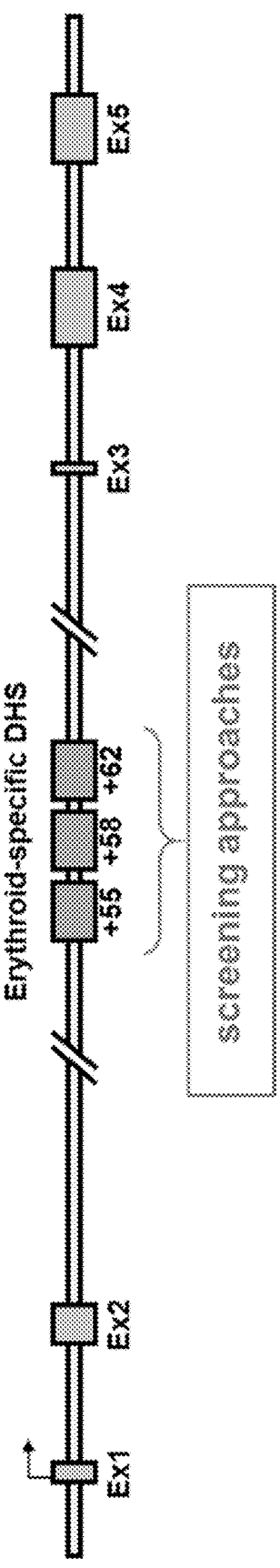
FIG. 1 depicts three Erythroid-specific DNase I hypersensitive sites (DHS) located in the second intron of the BCL11A gene in Chromosome 2.

SEQ ID NO: 1 is a sample spacer sequence, including the PAM, for a guide RNA (gRNA) for a S. pyogenes Cas9 endonuclease.

SEQ ID NO: 2 shows a known family of homing endonuclease, as classified by its structure.

SEQ ID NOs: 3-5 show sample sgRNA sequences.

SEQ ID NO: 6 is a 20 bp spacer sequence for targeting within a +55 DHS of the BCL11A gene with a S. pyogenes Cas9 endonuclease.

SEQ ID NO: 7 is a 20 bp spacer sequence for targeting within a +58 DHS of the BCL11A gene with a S. pyogenes Cas9 endonuclease.

SEQ ID NO: 8 is a 20 bp spacer sequence for targeting within a +55 DHS of the BCL11A gene with a S. pyogenes Cas9 endonuclease and a Protospacer Adjacent Motif (PAM) sequence.

SEQ ID NO: 9 is a 20 bp spacer sequence for targeting within a +58 DHS of the BCL11A gene with a S. pyogenes Cas9 endonuclease and a PAM sequence.

SEQ ID NO: 10 shows a sgRNA backbone sequence.

SEQ ID NO: 11 shows a full-length CG-001 sgRNA sequence.

SEQ ID NO: 12 shows a full-length CG-002 sgRNA sequence.

SEQ ID NO: 13 shows a full-length SPY101 sgRNA sequence.

SEQ ID NO: 14 is a spacer sequence included in SPY101.

SEQ ID NO: 15 shows a full-length 1619 sgRNA sequence.

SEQ ID NO: 16 shows a full-length 1621 sgRNA sequence.

As used herein, a gRNA or sgRNA comprising the nucleic acid sequence or the nucleotide sequence of a sequence herein or in the Sequence Listing includes both the modified and unmodified version of the sequence.

DETAILED DESCRIPTION

Fetal Hemoglobin

Fetal hemoglobin (HbF, $\alpha_2\gamma_2$) is the main oxygen transport protein in a human fetus and includes alpha ($\alpha$) and gamma ($\gamma$) subunits. HbF expression ceases about 6 months after birth. Adult hemoglobin (HbA, $\alpha_2\beta_2$) is the main oxygen transport protein in a human after ~34 weeks from birth, and includes alpha ($\alpha$) and beta ($\beta$) subunits. After 34 weeks, a developmental switch results in decreased transcription of the $\gamma$-globin genes and increased transcription of $\beta$-globin genes. Since many of the forms of hemoglobin-opathies are a result of the failure to produce normal $\beta$-globin protein in sufficient amounts or failure to produce normal $\beta$-globin protein entirely, increased expression of $\gamma$-globin (i.e., HbF) will ameliorate $\beta$-globin disease severity.

B-Cell Lymphoma 11A (BCL11A)

B-cell lymphoma 11A (BCL11A) is a gene located on Chromosome 2 and ranges from 60,451,167-60,553,567 bp (GRCh38). BCL11A is a zinc finger transcription factor that represses fetal hemoglobin (HbF) and downregulates HbF expression starting at about 6 weeks after birth. The BCL11A gene contains 5 exons, spanning 102.4 kb of genomic DNA. BCL11A also is under transcription regulation, including a binding domain in intron 2 for the master transcription factor GATA-1. GATA-1 binding enhances BCL11A expression which, in turn, represses HbF expression. Intron 2 contains multiple DNase I hypersensitive sites (DHS), including sites referred to as +55, +58, and +62 based on the distance in kilobases from the transcriptional start site. Various editing strategies are discussed below to create permanent changes to the genome that can result in at least one deletion, insertion, modulation, or inactivation of a transcriptional control sequence of the BCL11A gene. Naturally occurring SNPs within this region have been associated with decreased BCL11A expression and increased fetal Hb levels. These SNPs are organized around 3 DNA Hypersensitivity sites, +55DHS, +58DHS and +62DHS.

Editing Strategy

The methods provided herein, regardless of whether a cellular, or ex vivo or in vivo method can involve one or a combination of the following: 1) using one or more gRNAs for modulating or inactivating the transcriptional control sequence of the BCL11A gene, by deletions that arise due to the NHEJ pathway; 2) using one or more gRNAs for modulating or inactivating the transcriptional control sequence of the BCL11A gene, by insertions that arise due to the NHEJ pathway; or 3) using two or more gRNAs for creating a deletion or inversion in the transcriptional control sequence of the BCL11A gene.

Such methods use endonucleases, such as CRISPR-associated nucleases (Cas9, Cpf1 and the like), to create permanent changes to the genome that can result in at least one deletion, insertion, modulation, or inactivation of a transcriptional control sequence within or near the genomic locus of the BCL11A gene or other DNA sequence that encodes a regulatory element of the BCL11A gene. In this way, examples set forth in the present disclosure can create permanent changes to the genome that can result in at least one deletion, insertion, modulation, or inactivation of the transcriptional control sequence of the BCL11A gene with as few as a single treatment or a limited number of treatments (rather than deliver potential therapies for the lifetime of the patient). Some non-limiting examples are provided below.

Figure 2:
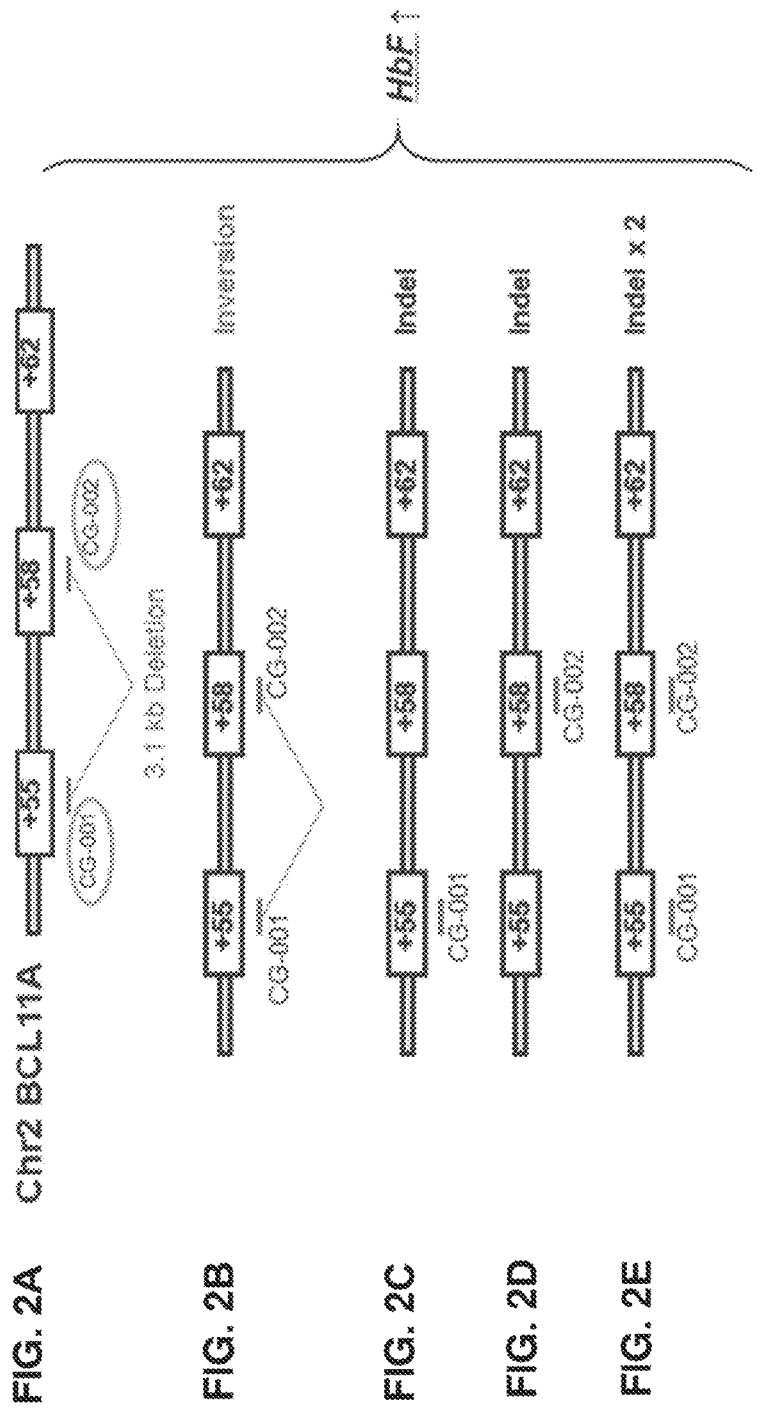
FIGS. 2A-2E depict an example deletion, inversion, or Indel (small insertion or deletion via non-homologous end joining) within the three Erythroid-specific DHS using one or both of gRNAs, CG-001 and CG-002.

In the first editing strategy, as depicted in FIG. 2A, a guide RNA (CG-001, SEQ ID NO: 11) targets within or near a +55 DHS of the BCL11A gene and a second guide RNA (CG-002, SEQ ID NO: 12) targets within or near a +58 DHS of the BCL11A gene. The two SSBs or DSBs generated by the two guide RNAs create a 3.1 kb deletion.

In the second editing strategy, as depicted in FIG. 2B, a guide RNA (CG-001, SEQ ID NO: 11) targets within or near a +55 DHS of the BCL11A gene and a second guide RNA (CG-002, SEQ ID NO: 12) targets within or near a +58 DHS of the BCL11A gene. The two SSBs or DSBs generated by the two guide RNAs create an inversion.

In the third editing strategy, as depicted in FIG. 2C, a guide RNA (CG-001, SEQ ID NO: 11) targets within or near a +55 DHS of the BCL11A gene. The SSB or DSB generated by the guide RNA creates an insertion or deletion via NHEJ. This third editing strategy can also be achieved when two gRNAs are present (CG-001 and CG-002), but only CG-001 generates a SSB or DSB resulting in an insertion or deletion, whereas CG-002 does not generate a SSB or DSB.

In the fourth editing strategy, as depicted in FIG. 2D, a guide RNA (CG-002, SEQ ID NO: 12) targets within or near a +58 DHS of the BCL11A gene. The SSB or DSB generated by the guide RNA creates an insertion or deletion via NHEJ. This fourth editing strategy can also be achieved when two gRNAs are present (CG-001 and CG-002), but only CG-002 generates a SSB or DSB resulting in an insertion or deletion, whereas CG-001 does not generate a SSB or DSB.

In the fifth editing strategy, as depicted in FIG. 2E, a guide RNA (CG-001, SEQ ID NO: 11) targets within or near a +55 DHS of the BCL11A gene and a second guide RNA (CG-002, SEQ ID NO: 12) targets within or near a +58 DHS of the BCL11A gene. The SSBs or DSBs generated by the two guide RNAs create separate insertions or deletions via NHEJ.

In the sixth editing strategy, a guide RNA (CG-001, SEQ ID NO: 11) targets within or near a +55 DHS of the BCL11A gene and a second guide RNA (SPY101, SEQ ID NO: 13) targets within or near a +58 DHS of the BCL11A gene. The two SSBs or DSBs generated by the two guide RNAs create a 3.1 kb deletion.

In the seventh editing strategy, a guide RNA (CG-001, SEQ ID NO: 11) targets within or near a +55 DHS of the BCL11A gene and a second guide RNA (SPY101, SEQ ID NO: 13) targets within or near a +58 DHS of the BCL11A gene. The two SSBs or DSBs generated by the two guide RNAs create an inversion.

In the eighth editing strategy, a guide RNA (CG-001, SEQ ID NO: 11) targets within or near a +55 DHS of the BCL11A gene and a second guide RNA (SPY101, SEQ ID NO: 13) targets within or near a +58 DHS of the BCL11A gene. The SSBs or DSBs generated by the two guide RNAs create separate insertions or deletions via NHEJ.

In the ninth editing strategy, a guide RNA (CG-002, SEQ ID NO: 12) targets within or near a +58 DHS of the BCL11A gene and a second guide RNA (SPY101, SEQ ID NO: 13) targets within or near a +58 DHS of the BCL11A gene. The two SSBs or DSBs generated by the two guide RNAs create a small deletion.

In the tenth editing strategy, a guide RNA (CG-002, SEQ ID NO: 12) targets within or near a +58 DHS of the BCL11A gene and a second guide RNA (SPY101, SEQ ID NO: 13) targets within or near a +58 DHS of the BCL11A gene. The two SSBs or DSBs generated by the two guide RNAs create a small inversion.

In the eleventh strategy, a guide RNA (CG-002, SEQ ID NO: 12) targets within or near a +58 DHS of the BCL11A gene and a second guide RNA (SPY101, SEQ ID NO: 13) targets within or near a +58 DHS of the BCL11A gene. The SSBs or DSBs generated by the two guide RNAs create separate insertions or deletions via NHEJ.

The advantages for the above strategies are similar, including in principle both short and long term beneficial clinical and laboratory effects.

Figures 5A, 5B:
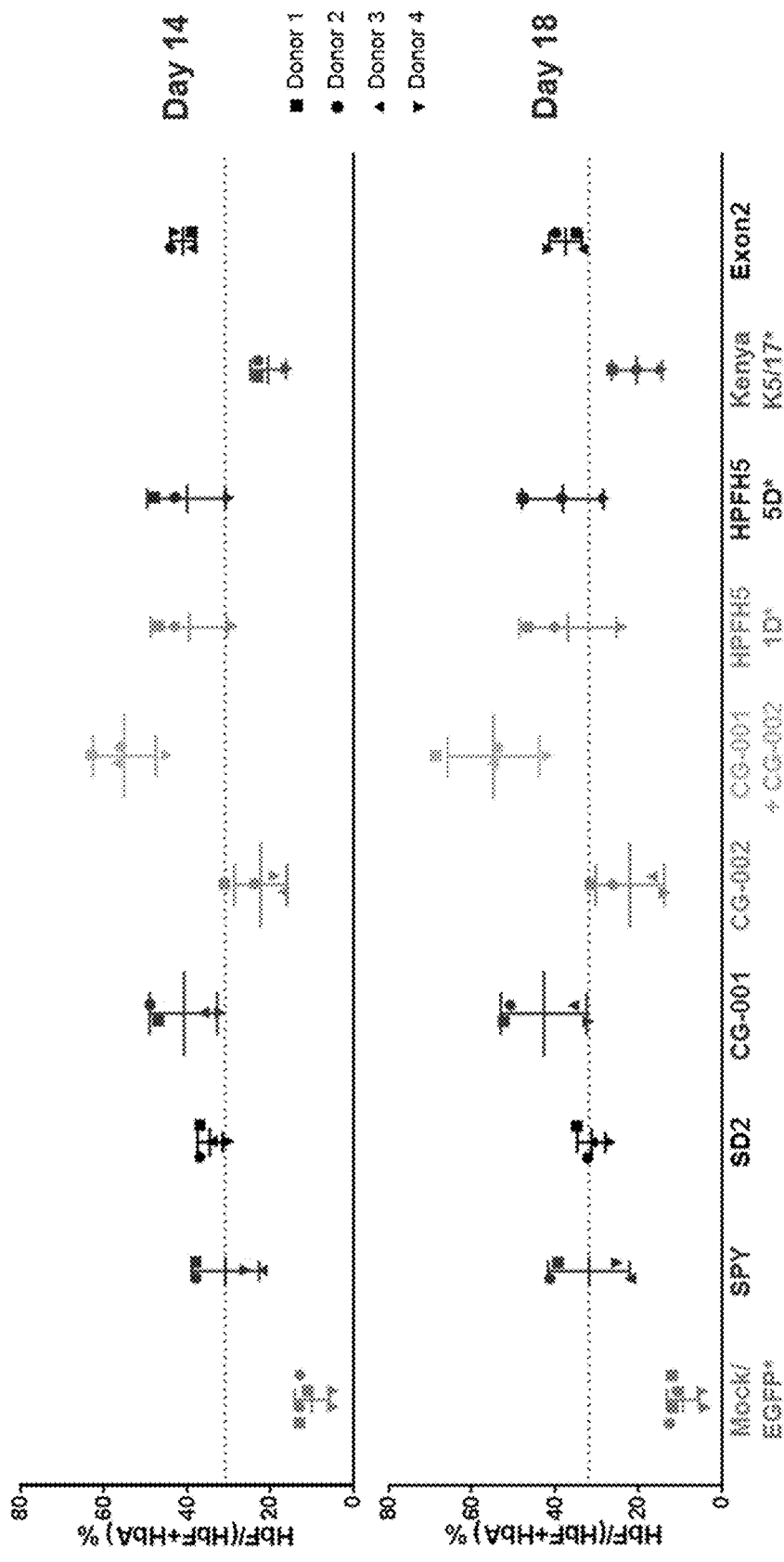
FIGS. 5A-5B show percentage of HbF in total hemoglobins (HbF/(HbF+HbA)) measured in erythrocytes differentiated in vitro for 14 or 18 days from human mPB CD34+ HSPCs isolated from Donors 1-4 and edited with different gRNAs and Cas9 protein.

Editing strategies involving a combination of guides CG-001 and CG-002 together resulted in the highest overall level of HbF protein upregulation in edited erythrocytes. As shown in FIGS. 5-6, the HbF protein upregulation in erythrocytes edited using CG-001+CG-002 gRNAs in combination showed significantly higher HbF protein upregulation compared to erythrocytes edited using guide RNA, SPY101. Guide RNA SPY101 was previously disclosed in WO 2017/182881. Guide RNA SD2 was previously disclosed in WO 2017/191503.

Editing strategies using a single guide, CG-001 or CG-002, alone resulted in a higher level of HbF protein upregulation in edited erythrocytes compared to unedited erythrocytes. As shown in FIGS. 5-6, the HbF protein upregulation in erythrocytes edited using single guide editing strategy (CG-001 alone) showed a higher HbF protein upregulation compared to erythrocytes edited using guide RNA, SPY101.

Other Editing Strategies

In another editing strategy (1), a guide RNA can target within or near a +58 DHS of the BCL11A gene upstream of the GATA1 binding site. The SSB or DSB generated by the guide RNA can create an insertion or deletion via NHEJ.

In another editing strategy (2), a guide RNA can target within or near a +58 DHS of the BCL11A gene downstream of the GATA1 binding site. The SSB or DSB generated by the guide RNA can create an insertion or deletion via NHEJ.

In another editing strategy (3), a first guide RNA targets within or near a +58 DHS of the BCL11A gene upstream of the GATA1 binding site and a second guide RNA targets within or near a +58 DHS of the BCL11A gene downstream of the GATA1 binding site. The two SSBs or DSBs generated by the two guide RNAs create a deletion. The deletion comprises the GATA1 binding site.

In another editing strategy (4), a first guide RNA targets upstream of a +55 DHS of the BCL11A gene and a second guide RNA targets downstream of a +55 DHS of the BCL11A gene. The two SSBs or DSBs generated by the two guide RNAs create a deletion. The deletion comprises the +55 DHS of the BCL11A gene or a fragment thereof.

In another editing strategy (5), a first guide RNA targets upstream of a +58 DHS of the BCL11A gene and a second guide RNA targets downstream of a +58 DHS of the BCL11A gene. The two SSBs or DSBs generated by the two guide RNAs create a deletion. The deletion comprises the +58 DHS of the BCL11A gene or a fragment thereof.

In another editing strategy (6), a first guide RNA targets upstream of a +62 DHS of the BCL11A gene and a second guide RNA targets downstream of a +62 DHS of the BCL11A gene. The two SSBs or DSBs generated by the two guide RNAs create a deletion. The deletion comprises the +62 DHS of the BCL11A gene or a fragment thereof.

In another editing strategy (7), a first guide RNA targets upstream of a +55 DHS of the BCL11A gene and a second guide RNA targets downstream of a +58 DHS of the BCL11A gene. The two SSBs or DSBs generated by the two guide RNAs create a deletion. The deletion comprises the +55 DHS and +58 DHS of the BCL11A gene or fragments thereof.

In another editing strategy (8), a first guide RNA targets upstream of a +58 DHS of the BCL11A gene and a second guide RNA targets downstream of a +62 DHS of the BCL11A gene. The two SSBs or DSBs generated by the two guide RNAs create a deletion. The deletion comprises the +58 DHS and +62 DHS of the BCL11A gene or fragments thereof.

In another editing strategy (9), a first guide RNA targets upstream of a +55 DHS of the BCL11A gene and a second guide RNA targets downstream of a +62 DHS of the BCL11A gene. The two SSBs or DSBs generated by the two guide RNAs create a deletion. The deletion comprises the +55 DHS, +58 DHS, and +62 DHS of the BCL11A gene or fragments thereof.

In another editing strategy (10), a guide RNA can target within or near a +62 DHS of the BCL11A gene upstream of the GATA1 binding site where an HbF associated SNP is located (rs1427407). The SSB or DSB generated by the guide RNA can create an insertion or deletion via NHEJ.

In another editing strategy (11), a guide RNA can target within or near a +62 DHS of the BCL11A gene downstream of the GATA1 binding site where an HbF associated SNP is located (rs1427407). The SSB or DSB generated by the guide RNA can create an insertion or deletion via NHEJ.

In another editing strategy (12), a guide RNA can target within or near a +55 DHS of the BCL11A gene. The SSB or DSB generated by the guide RNA can create an insertion or deletion via NHEJ.

In another editing strategy (13), a guide RNA can target within or near a +58 DHS of the BCL11A gene. The SSB or DSB generated by the guide RNA can create an insertion or deletion via NHEJ.

In another editing strategy (14), a guide RNA can target within or near a +62 DHS of the BCL11A gene. The SSB or DSB generated by the guide RNA can create an insertion or deletion via NHEJ.

Ex Vivo Based Therapy

Provided herein are methods for treating a patient with a hemoglobinopathy. An aspect of such method is an ex vivo cell-based therapy. For example, a patient specific induced pluripotent stem cell (iPSC) can be created. Then, the chromosomal DNA of these iPS cells can be edited using the materials and methods described herein. Next, the genome-edited iPSCs can be differentiated into hematopoietic progenitor cells. Finally, the hematopoietic progenitor cells can be implanted into the patient.

Yet another aspect of such method is an ex vivo cell-based therapy. For example, a mesenchymal stem cell can be isolated from the patient, which can be isolated from the patient's bone marrow or peripheral blood. Next, the chromosomal DNA of these mesenchymal stem cells can be edited using the materials and methods described herein. Next, the genome-edited mesenchymal stem cells can be differentiated into hematopoietic progenitor cells. Finally, these hematopoietic progenitor cells can be implanted into the patient.

A further aspect of such method is an ex vivo cell-based therapy. For example, a hematopoietic progenitor cell can be isolated from the patient. Next, the chromosomal DNA of these cells can be edited using the materials and methods described herein. Finally, the genome-edited hematopoietic progenitor cells can be implanted into the patient.

One advantage of an ex vivo cell therapy approach is the ability to conduct a comprehensive analysis of the therapeutic prior to administration. Nuclease-based therapeutics can have some level of off-target effects. Performing gene correction ex vivo allows one to characterize the corrected cell population prior to implantation. The present disclosure includes sequencing the entire genome of the corrected cells to ensure that the off-target effects, if any, can be in genomic locations associated with minimal risk to the patient. Furthermore, populations of specific cells, including clonal populations, can be isolated prior to implantation.

Another advantage of ex vivo cell therapy relates to genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability. In contrast, other primary cells are viable for only a few passages and difficult to clonally expand. Thus, manipulation of iPSCs for the treatment of a hemoglobinopathy can be much easier, and can shorten the amount of time needed to make the desired genetic correction.

For ex vivo therapy, transplantation requires clearance of bone-marrow niches or the donor HSCs to engraft. Current methods rely on radiation and/or chemotherapy. Due to the limitations these impose, safer conditioning regiments have been and are being developed, such as immunodepletion of bone marrow cells by antibodies or antibody toxin conjugates directed against hematopoietic cell surface markers, for example CD117, c-kit and others. Success of HSC transplantation depends upon efficient homing to bone marrow, subsequent engraftment, and bone marrow repopulation. The level of gene-edited cells engrafted is important, as is the ability of the cells' multilineage engraftment.

Hematopoietic stem cells (HSCs) are an important target for ex vivo gene therapy as they provide a prolonged source of the corrected cells. Treated CD34+ cells would be returned to the patient.

In Vivo Based Therapy

Methods can also include an in vivo based therapy. Chromosomal DNA of the cells in the patient is edited using the materials and methods described herein. The cells can be bone marrow cells, hematopoietic progenitor cells, or CD34+ cells.

Although blood cells present an attractive target for ex vivo treatment and therapy, increased efficacy in delivery may permit direct in vivo delivery to the hematopoietic stem cells (HSCs) and/or other B and T cell progenitors, such as CD34+ cells. Ideally the targeting and editing would be directed to the relevant cells. Cleavage in other cells can also be prevented by the use of promoters only active in certain cells and or developmental stages. Additional promoters are inducible, and therefore can be temporally controlled if the nuclease is delivered as a plasmid. The amount of time that delivered RNA and protein remain in the cell can also be adjusted using treatments or domains added to change the half-life. In vivo treatment would eliminate a number of treatment steps, but a lower rate of delivery can require higher rates of editing. In vivo treatment can eliminate problems and losses from ex vivo treatment and engraftment.

An advantage of in vivo gene therapy can be the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Also provided herein is a cellular method for editing the BCL11A gene in a cell by genome editing. For example, a cell can be isolated from a patient or animal. Then, the chromosomal DNA of the cell can be edited using the materials and methods described herein.

In addition to the editing options listed above, Cas9 or similar proteins can be used to target effector domains to the same target sites that can be identified for editing, or additional target sites within range of the effector domain. A range of chromatin modifying enzymes, methylases or demethlyases can be used to alter expression of the target gene. These types of epigenetic regulation have some advantages, particularly as they are limited in possible off-target effects.

The regulation of transcription and translation implicates a number of different classes of sites that interact with cellular proteins or nucleotides. Often the DNA binding sites of transcription factors or other proteins can be targeted for mutation or deletion to study the role of the site, though they can also be targeted to change gene expression. Sites can be added through non-homologous end joining NHEJ or direct genome editing by homology directed repair (HDR). Increased use of genome sequencing, RNA expression and genome-wide studies of transcription factor binding have increased our ability to identify how the sites lead to developmental or temporal gene regulation. These control systems can be direct or can involve extensive cooperative regulation that can require the integration of activities from multiple enhancers. Transcription factors typically bind 6-12 bp-long degenerate DNA sequences. The low level of specificity provided by individual sites suggests that complex interactions and rules are involved in binding and the functional outcome. Binding sites with less degeneracy can provide simpler means of regulation. Artificial transcription factors can be designed to specify longer sequences that have less similar sequences in the genome and have lower potential for off-target cleavage. Any of these types of binding sites can be mutated, deleted or even created to enable changes in gene regulation or expression. GATA transcription factors are a family of transcription factors characterized by their ability to bind to the GATA DNA binding sequence. A GATA binding sequence is located in the +58 DNA DHS of the BCL11A gene and +62 DNA DHS of the BCL11A gene.

Genome Editing

Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and NHEJ, as recently reviewed in Cox et al., Nature Medicine 21(2), 121-31 (2015). These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ", in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi:10.1038/nsmb.2961(2015); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair or non-homologous end joining or alternative non-homologous end joining (A-NHEJ) or microhomology-mediated end joining). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that can be homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide, double-stranded oligonucleotide, or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few base pairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence or polynucleotide donor template) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science*, 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Exemplary CRISPR/Cas polypeptides include the Cas9 polypeptides in FIG. 1 of Fonfara et al., *Nucleic Acids Research*, 42: 2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA. The site-directed nuclease or polypeptide can be administered to a cell or a patient as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In the CRISPR/Cas or CRISPR/Cpf1 systems disclosed herein, the site-directed polypeptide can be an endonuclease, such as a DNA endonuclease.

A site-directed polypeptide can comprises a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally-occurring and recombinant Cas9s. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RnaseH-like fold.

RuvC/RnaseH domains are involved in a diverse set of nucleic acid-based functions including acting on both RNA and DNA. The RnaseH domain comprises 5 β-strands surrounded by a plurality of α-helices. RuvC/RnaseH or RuvC/RnaseH-like domains comprise a metal binding site (e.g., a divalent cation binding site). RuvC/RnaseH or RuvC/RnaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways (e.g., homology-dependent repair (HDR) or NHEJ or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few base pairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from S. pyogenes, US2014/0068797 Sequence ID No. 8 or Sapranauskas et al., Nucleic Acids Res, 39(21): 9275-9282 (2011)], and various other site-directed polypeptides. The site-directed polypeptide can comprise at least 70, 75, 80, 85, 90, 95, 97, 99, or 100% identity to a wild-type site-directed polypeptide (e.g., Cas9 from S. pyogenes, supra) over 10 contiguous amino acids. The site-directed polypeptide can comprise at most: 70, 75, 80, 85, 90, 95, 97, 99, or 100% identity to a wild-type site-directed polypeptide (e.g., Cas9 from S. pyogenes, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from S. pyogenes, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from S. pyogenes, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from S. pyogenes, supra) over 10 contiguous amino acids in a RuvC nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from S. pyogenes, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from S. pyogenes, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

The modified form of the site-directed polypeptide can comprise a mutation such that it can induce a single-strand break (SSB) on a target nucleic acid (e.g., by cutting only one of the sugar-phosphate backbones of a double-strand target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from S. pyogenes, supra). The mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary S. pyogenes Cas9 polypeptide, such as Asp10, His840, Asn854 and Asn856, are mutated to inactivate one or more of the plurality of nucleic acid-cleaving domains (e.g., nuclease domains). The residues to be mutated can correspond to residues Asp10, His840, Asn854 and Asn856 in the wild-type exemplary S. pyogenes Cas9 polypeptide (e.g., as determined by sequence and/or structural alignment). Non-limiting examples of mutations include D10A, H840A, N854A or N856A. One skilled in the art will recognize that mutations other than alanine substitutions can be suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to as "nickases".

Nickase variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target DNA. The site-directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., S. pyogenes), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., S. pyogenes), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., S. pyogenes), and two nucleic acid cleaving domains, wherein one or both of the nucleic acid cleaving domains comprise at least 50% amino acid identity to a nuclease domain from Cas9 from a bacterium (e.g., S. pyogenes).

The site-directed polypeptide can comprise an amino acid sequence comprising at least 15% amino acid identity to a Cas9 from a bacterium (e.g., S. pyogenes), two nucleic acid cleaving domains (i.e., a HNH domain and a RuvC domain), and non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., S. pyogenes), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., S. pyogenes), and two nucleic acid cleaving domains (i.e., a HNH domain and a RuvC domain), wherein one of the nuclease domains comprises mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA can comprise at least a spacer sequence that hybridizes to a target nucleic acid sequence of interest, and a CRISPR repeat sequence. In Type II systems, the gRNA also comprises a second RNA called the tracrRNA sequence.

In the Type II guide RNA (gRNA), the CRISPR repeat sequence and tracrRNA sequence hybridize to each other to form a duplex. In the Type V guide RNA (gRNA), the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Exemplary guide RNAs include the spacer sequences in SEQ ID NOs: 6-7 and 14 and the sgRNA sequences in SEQ ID NOs: 11-13 of the Sequence Listing. Each guide RNA can be designed to include a spacer sequence complementary to its genomic target sequence. For example, each of the spacer sequences in SEQ ID NOs: 6-7 and 14 of the Sequence Listing can be put into a single RNA chimera or a crRNA (along with a corresponding tracrRNA). See Jinek et al., Science, 337, 816-821 (2012) and Deltcheva et al., Nature, 471, 602-607 (2011) or Table 1.

The genome-targeting nucleic acid can be a double-molecule guide RNA. The genome-targeting nucleic acid can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

A single-molecule guide RNA (sgRNA) in a Type V system can comprise, in the 5' to 3' direction, a minimum CRISPR repeat sequence and a spacer sequence.

The sgRNA can comprise a 20 nucleotide spacer sequence at the 5' end of the sgRNA sequence. The sgRNA can comprise a less than a 20 nucleotide spacer sequence at the 5' end of the sgRNA sequence. The sgRNA can comprise a more than 20 nucleotide spacer sequence at the 5' end of the sgRNA sequence. The sgRNA can comprise a 17 nucleotide spacer sequence at the 5' end of the sgRNA sequence. The sgRNA can comprise a 18 nucleotide spacer sequence at the 5' end of the sgRNA sequence. The sgRNA can comprise a 19 nucleotide spacer sequence at the 5' end of the sgRNA sequence. The sgRNA can comprise a 21 nucleotide spacer sequence at the 5' end of the sgRNA sequence. The sgRNA can comprise a 22 nucleotide spacer sequence at the 5' end of the sgRNA sequence. The sgRNA can comprise a 23 nucleotide spacer sequence at the 5' end of the sgRNA sequence. The sgRNA can comprise a 24 nucleotide spacer sequence at the 5' end of the sgRNA sequence. The sgRNA can comprise a variable length spacer sequence with 17-30 nucleotides at the 5' end of the sgRNA sequence (see Table 1).

The sgRNA can comprise no uracil at the 3'end of the sgRNA sequence, such as in SEQ ID NO: 4 of Table 1. The sgRNA can comprise one or more uracil at the 3'end of the sgRNA sequence, such as in SEQ ID NO: 5 in Table 1. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

TABLE 1

| SEQ ID NO. | sgRNA sequence |
|---|---|
| 3 | nnnnnnnnnnnnnnnnnnnnguuuuagagcuagaaauagc aaguuaaaauaaggcuaguccguuaucaacuugaaaaagu ggcaccgagucggugcuuuu |
| 4 | nnnnnnnnnnnnnnnnnnnnguuuuagagcuagaaauagc aaguuaaaauaaggcuaguccguuaucaacuugaaaaagu ggcaccgagucggugc |
| 5 | n$_{(17-30)}$guuuuagagcuagaaauagcaaguuaaaauaa ggcuaguccguuaucaacuugaaaaaguggcaccgagucg gugcu$_{(1-8)}$ |

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some examples of genome-targeting nucleic acids, a spacer extension sequence can modify activity, provide stability and/or provide a location for modifications of a genome-targeting nucleic acid. A spacer extension sequence can modify on- or off-target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. The spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can be less than 10 nucleotides in length. The spacer extension sequence can be between 10-30 nucleotides in length. The spacer extension sequence can be between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional controls, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. The target nucleic acid can comprise at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-NNNNNNNNNNNNNNNNNNNNNRG-3' (SEQ ID NO: 1), the target nucleic acid can comprise the sequence that corresponds to the Ns, wherein N is any nucleotide, and the underlined NRG sequence is the *S. pyogenes* PAM.

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer can comprise 24 nucleotides. In some examples, the spacer can comprise 23 nucleotides. In some examples, the spacer can comprise 22 nucleotides. In some examples, the spacer can comprise 21 nucleotides. In some examples, the spacer can comprise 20 nucleotides. In some examples, the spacer can comprise 19 nucleotides. In some examples, the spacer can comprise 18 nucleotides. In some examples, the spacer can comprise 17 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence can be a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some examples, the minimum CRISPR repeat sequence can be approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from S. pyogenes) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from S. pyogenes).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a site-directed polypeptide. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from S. pyogenes) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, 5 or mismatches. The duplex can comprise at most about 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least 1, 2, 3, 4, or 5 or more unpaired nucleotides. A bulge on the minimum CRISPR repeat side of the duplex can comprise at most 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least 1, 2, 3, 4, 5, 6, 7, 8, 9, or 10 or more unpaired nucleotides. A bulge on the minimum tracrRNA sequence side of the duplex can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. In some examples, a bulge can comprise at most one wobble pairing. A bulge can comprise at least one purine nucleotide. A bulge can comprise at least 3 purine nucleotides. A bulge sequence can comprises at least 5 purine nucleotides. A bulge sequence can comprise at least one guanine nucleotide. In some examples, a bulge sequence can comprise at least one adenine nucleotide.

Hairpins

In various examples, one or more hairpins can be located 3' to the minimum tracrRNA in the 3' tracrRNA sequence.

The hairpin can start at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about 1, 2, 3, 4, 5, 6, 7, 8, 9, 10, 15, or 20 or more consecutive nucleotides. The hairpin can comprise at most about 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. pyogenes).

The 3' tracrRNA sequence can have a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from S. pyogenes) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from S. pyogenes) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence may be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional controls, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

A step of the ex vivo methods of the present disclosure can comprise genetic editing the patient specific iPSC cells using genome engineering. Alternatively, a step of the ex vivo methods of the present disclosure can comprise editing mesenchymal stem cell, or hematopoietic progenitor cell.

Likewise, a step of the in vivo methods of the present disclosure can comprise editing the cells in a patient having hemoglobinopathy using genome engineering. Similarly, a step in the cellular methods of the present disclosure can comprise editing within or near a BCL11A gene or other DNA sequence that encodes a regulatory element of the BCL11A gene in a human cell by genome engineering.

Different patients with hemoglobinopathy will generally require different editing strategies. Any CRISPR endonuclease may be used in the methods of the present disclosure, each CRISPR endonuclease having its own associated PAM, which may or may not be disease specific. For example, gRNA spacer sequences for targeting within or near a BCL11A gene or other DNA sequence that encodes a regulatory element of the BCL11A gene with a CRISPR/Cas9 endonuclease from *S. pyogenes* have been identified in SEQ ID NOs: 6-7 and 14 of the Sequence Listing.

For example, the transcriptional control sequence of the BCL11A gene can be modulated or inactivated by deletions that arise due to the NHEJ pathway. NHEJ can be used to delete segments of the transcriptional control sequence of the BCL11A gene, either directly or by altering splice donor or acceptor sites through cleavage by one gRNA targeting several locations, or several gRNAs.

Some genome engineering strategies involve modulating or inactivating a transcriptional control sequence of the BCL11A gene by deleting at least a portion of the transcriptional control sequence of the BCL11A gene. This strategy can modulate or inactivate the transcriptional control sequence of the BCL11A gene and reverse, treat, and/or mitigate the diseased state.

NHEJ was used to insert a 15-kb inducible gene expression cassette into a defined locus in human cell lines after nuclease cleavage. Maresca, M., Lin, V. G., Guo, N. & Yang, Y., Genome Res 23, 539-546 (2013).

In addition to genome editing by NHEJ, site-specific gene insertions have been conducted that use the NHEJ pathway. A combination approach may be applicable in certain settings, possibly including intron/exon borders. NHEJ may prove effective for ligation in the intron.

The terms "near" or "proximal" refer to the distance between the SSB or DSB locus and a reference locus or gene. For example, the SSB or DSB locus can be less than 10 kb from the reference locus or gene. The SSB or DSB locus can be less than 9 kb from the reference locus or gene. The SSB or DSB locus can be less than 8 kb from the reference locus gene. The SSB or DSB locus can be less than 7 kb from the reference locus or gene. The SSB or DSB locus can be less than 6 kb from the reference locus or gene. The SSB or DSB can be less than 5 kb from the reference locus or gene. The SSB or DSB locus can be less than 4 kb from the reference locus or gene. The SSB or DSB can be less than about 3 kb from a reference locus or gene. The SSB or DSB locus can be within 2 kb, within 1 kb, within 0.5 kb, within 0.1 kb, within 50 bp, within 25 bp, or within less than 10 bp from the reference locus or gene.

Exon or Intron Deletion

Another genome engineering strategy involves exon or intron deletion. Targeted deletion of specific exons or introns can be an attractive strategy for treating a large subset of patients with a single therapeutic cocktail. Deletions can either be single exon or intron deletions or multi-exon or intron deletions. While multi-exon deletions can reach a larger number of patients, for larger deletions the efficiency of deletion greatly decreases with increased size. Therefore, deletions range can be from 40 to 10,000 base pairs (bp) in size. For example, deletions can range from 40-100; 100-

300; 300-500; 500-1,000; 1,000-2,000; 2,000-3,000; 3,000-5,000; or 5,000-10,000 base pairs in size. It may be desirable to delete an intron if the intron contains a regulatory element, such as a transcriptional control element (e.g., a transcription factor binding site).

In order to ensure that the pre-mRNA is properly processed following deletion, the surrounding splicing signals can be deleted. Splicing donor and acceptors are generally within 100 base pairs of the neighboring intron. Therefore, in some examples, methods can provide all gRNAs that cut approximately +/−100-3100 bp with respect to each exon/intron junction of interest.

For any of the genome editing strategies, gene editing can be confirmed by sequencing or PCR analysis.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

RNPs

The site-directed polypeptide and genome-targeting nucleic acid can each be administered separately to a cell or a patient. On the other hand, the site-directed polypeptide can be pre-complexed with one or more genome-targeting nucleic acids (guide RNA, sgRNA, or crRNA together with a tracrRNA). The pre-complexed material can then be administered to a cell or a patient. Such pre-complexed material is known as a ribonucleoprotein particle (RNP). The site-directed polypeptide in the RNP can be, for example, a Cas9 endonuclease or a Cpf1 endonuclease. The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to site-directed polypeptide in the RNP can be 1:1. For example, the weight ratio of sgRNA to Cas9 endonuclease in the RNP can be 1:1. For example, the sgRNA can comprise the nucleic acid sequence of SEQ ID NO: 11 or 12, the Cas9 endonuclease can be a S. pyogenes Cas9 comprising a N-terminus SV40 NLS and a C-terminus SV40 NLS, and the weight ratio of sgRNA to Cas9 endonuclease can be 1:1.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first non-limiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another non-limiting example of target sequence selection or optimization, the frequency of off-target activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some cases, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs can be regularly induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten base pairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce replacements that result in the modulation or inactivation of transcriptional control protein activity, as well as the selection of specific target sequences within such regions that are designed to minimize off-target events relative to on-target events.

Nucleic Acid Modifications (Chemical and Structural Modifications)

In some cases, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of non-limiting illustrations of such uses, modifications of guide RNAs can be used to enhance the formation or stability of the CRISPR/Cas9/Cpf1 genome editing complex comprising guide RNAs, which can be single-molecule guides or double-molecule, and a Cas or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach that can be used for generating chemically-modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications can comprise 2'-fluoro, 2'-amino or 2' O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)—O—$CH_2$ (known as a methylene(methylimino) or MMI backbone), $CH_2$—O—N($CH_3$)—$CH_2$, $CH_2$—N($CH_3$)—N ($CH_3$)—$CH_2$ and O—N($CH_3$)— $CH_2$—$CH_2$ backbones, wherein the native phosphodiester backbone is represented as O— P—O— CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185, 444; 5,214,134; 5,216,141; 5,235,033; 5,264,562; 5,264, 564; 5,405,938; 5,434,257; 5,466,677; 5,470,967; 5,489, 677; 5,541,307; 5,561,225; 5,596,086; 5,602,240; 5,610, 289; 5,602,240; 5,608,046; 5,610,289; 5,618,704; 5,623, 070; 5,663,312; 5,633,360; 5,677,437; and 5,677,439.

One or more substituted sugar moieties can also be included, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$, or $O(CH_2)n$ $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-0-$CH_2CH_2OCH_3$, also known as 2'-O-(2-methoxyethyl)) (Martin et al, Helv. Chim. Acta, 1995, 78, 486). Other modifications include 2'-methoxy (2'-0-$CH_3$), 2'-propoxy (2'-$OCH_2$ $CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719, 262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and US Patent Application Publication 2003/0158403.

Thus, the term "modified" refers to a non-natural sugar, phosphate, or base that is incorporated into a guide RNA, an endonuclease, or transcriptional control sequence of BCL11A or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmitoyl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present disclosure. Representative conjugate groups are disclosed in International Patent Application No. PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941;

4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16:Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, ei61 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

microRNAs (miRNAs)

Another class of gene regulatory regions having these features is microRNA (miRNA) binding sites. miRNAs are non-coding RNAs that play key roles in post-transcriptional gene regulation. miRNAs can regulate the expression of 30% of all mammalian protein-encoding genes. Specific and potent gene silencing by double stranded RNA (RNAi) was discovered, plus additional small noncoding RNA. The largest class of noncoding RNAs important for gene silencing is miRNAs. In mammals, miRNAs are first transcribed as long RNA transcripts, which can be separate transcriptional units, part of protein introns, or other transcripts. The long transcripts are called primary miRNA (pri-miRNA) that include imperfectly base-paired hairpin structures. These pri-miRNA can be cleaved into one or more shorter precursor miRNAs (pre-miRNAs) by Microprocessor, a protein complex in the nucleus, involving Drosha.

Pre-miRNAs are short stem loops ~70 nucleotides in length with a 2-nucleotide 3'-overhang that are exported, into the mature 19-25 nucleotide miRNA:miRNA*duplexes. The miRNA strand with lower base pairing stability (the guide strand) can be loaded onto the RNA-induced silencing complex (RISC). The passenger guide strand (marked with *), can be functional, but is usually degraded. The mature miRNA tethers RISC to partly complementary sequence motifs in target mRNAs predominantly found within the 3' untranslated regions (UTRs) and induces posttranscriptional gene silencing (Bartel, D. P. Cell 136, 215-233 (2009); Saj, A. & Lai, E. C. Curr Opin Genet Dev 21, 504-510 (2011)).

miRNAs can be important in development, differentiation, cell cycle and growth control, and in virtually all biological pathways in mammals and other multicellular organisms. miRNAs can also be involved in cell cycle control, apoptosis and stem cell differentiation, hematopoiesis, hypoxia, muscle development, neurogenesis, insulin secretion, cholesterol metabolism, aging, viral replication and immune responses.

A single miRNA can target hundreds of different mRNA transcripts, while an individual transcript can be targeted by many different miRNAs. More than 28645 microRNAs have been annotated in the latest release of miRBase (v.21). Some miRNAs can be encoded by multiple loci, some of which can be expressed from tandemly co-transcribed clusters. The features allow for complex regulatory networks with multiple pathways and feedback controls. miRNAs can be integral parts of these feedback and regulatory circuits and can help regulate gene expression by keeping protein production within limits (Herranz, H. & Cohen, S. M. Genes Dev 24, 1339-1344 (2010); Posadas, D. M. & Carthew, R. W. Curr Opin Genet Dev 27, 1-6 (2014)).

miRNA can also be important in a large number of human diseases that are associated with abnormal miRNA expression. This association underscores the importance of the miRNA regulatory pathway. Recent miRNA deletion studies have linked miRNA with regulation of the immune responses (Stern-Ginossar, N. et al., Science 317, 376-381 (2007)).

miRNA also have a strong link to cancer and can play a role in different types of cancer. miRNAs have been found to be downregulated in a number of tumors. miRNA can be important in the regulation of key cancer-related pathways, such as cell cycle control and the DNA damage response, and can therefore be used in diagnosis and can be targeted clinically. MicroRNAs can delicately regulate the balance of angiogenesis, such that experiments depleting all microRNAs suppress tumor angiogenesis (Chen, S. et al., Genes Dev 28, 1054-1067 (2014)).

As has been shown for protein coding genes, miRNA genes can also be subject to epigenetic changes occurring with cancer. Many miRNA loci can be associated with CpG islands increasing their opportunity for regulation by DNA methylation (Weber, B., Stresemann, C., Brueckner, B. & Lyko, F. Cell Cycle 6, 1001-1005 (2007)). The majority of studies have used treatment with chromatin remodeling drugs to reveal epigenetically silenced miRNAs.

In addition to their role in RNA silencing, miRNA can also activate translation (Posadas, D. M. & Carthew, R. W. Curr Opin Genet Dev 27, 1-6 (2014)). Knocking out these sites may lead to decreased expression of the targeted gene, while introducing these sites may increase expression.

Individual miRNA can be knocked out most effectively by mutating the seed sequence (bases 2-8 of the microRNA), which can be important for binding specificity. Cleavage in this region, followed by mis-repair by NHEJ can effectively abolish miRNA function by blocking binding to target sites. miRNA could also be inhibited by specific targeting of the special loop region adjacent to the palindromic sequence. Catalytically inactive Cas9 can also be used to inhibit shRNA expression (Zhao, Y. et al., Sci Rep 4, 3943 (2014)). In addition to targeting the miRNA, the binding sites can also be targeted and mutated to prevent the silencing by miRNA.

Human Cells

For ameliorating hemoglobinopathies, as described and illustrated herein, the principal targets for gene editing are human cells. For example, in the ex vivo methods, the human cells can be somatic cells, which after being modified using the techniques as described, can give rise to progenitor cells. For example, in the in vivo methods, the human cells can be a bone marrow cell, a hematopoietic progenitor cell, or a CD34+ cell.

By performing gene editing in autologous cells that are derived from and therefore already completely matched with the patient in need, it is possible to generate cells that can be safely re-introduced into the patient, and effectively give rise to a population of cells that can be effective in ameliorating one or more clinical conditions associated with the patient's disease.

Progenitor cells (also referred to as stem cells herein) are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a hematopoietic progenitor cell), which in turn can differentiate into other types of precursor cells further down the pathway (such as a hematopoietic precursor), and then to an end-stage differentiated cell, such as a erythrocyte, which plays a characteristic role in a certain tissue type, and may or may not retain the capacity to proliferate further.

The term "hematopoietic progenitor cell" refers to cells of a stem cell lineage that give rise to all the blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells).

A "cell of the erythroid lineage" indicates that the cell being contacted is a cell that undergoes erythropoiesis, such that upon final differentiation it forms an erythrocyte or red blood cell. Such cells originate from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage" comprise hematopoietic progenitor cells, rubriblasts, prorubricytes, erythroblasts, metarubricytes, reticulocytes, and erythrocytes.

The hematopoietic progenitor cell can express at least one of the following cell surface markers characteristic of hematopoietic progenitor cells: CD34+, CD59+, Thyl/CD90+, CD38lo/−, and C-kit/CDl 17+. In some examples provided herein, the hematopoietic progenitors can be CD34+.

The hematopoietic progenitor cell can be a peripheral blood stem cell obtained from the patient after the patient has been treated with one or more factors such as granulocyte colony stimulating factor (optionally in combination with Plerixaflor). CD34+ cells can be enriched using Clini-MACS® Cell Selection System (Miltenyi Biotec). CD34+ cells can be stimulated in serum-free medium (e.g., Cell-Grow SCGM media, CellGenix) with cytokines (e.g., SCF, rhTPO, rhFLT3) before genome editing. Addition of SRi and dmPGE2 and/or other factors is contemplated to improve long-term engraftment.

The hematopoietic progenitor cells of the erythroid lineage can have a cell surface marker characteristic of the erythroid lineage: such as CD71 and Terl 19.

Hematopoietic stem cells (HSCs) can be an important target for gene therapy as they provide a prolonged source of the corrected cells. HSCs give rise to both the myeloid and lymphoid lineages of blood cells. Mature blood cells have a finite life-span and must be continuously replaced throughout life. Blood cells are continually produced by the proliferation and differentiation of a population of pluripotent HSCs that can be replenished by self-renewal. Bone marrow (BM) is the major site of hematopoiesis in humans and a good source for hematopoietic stem and progenitor cells (HSPCs). HSPCs can be found in small numbers in the peripheral blood (PB). In some indications or treatments their numbers increase. The progeny of HSCs mature through stages, generating multi-potential and lineage-committed progenitor cells including the lymphoid progenitor cells giving rise to the cells expressing BCL11A. B and T cell progenitors are the two cell populations requiring the activity of BCL11A, so they could be edited at the stages prior to re-arrangement, though correcting progenitors has the advantage of continuing to be a source of corrected cells. Treated cells, such as CD34+ cells, would be returned to the patient. The level of engraftment can be important, as is the ability of the cells' multilineage engraftment of gene-edited cells following CD34+ infusion in vivo.

Induced Pluripotent Stem Cells

The genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a progenitor cell to be administered to the subject (e.g., autologous cells). Because the progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming can encompass complete reversion of the differentiation state of a differentiated cell (e.g., a somatic cell) to a pluripotent state or a multipotent state. Reprogramming can encompass complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm.2014-0121 (2014); Focosi et al., Blood Cancer Journal 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes, including, for example, Oct-3/4 (also known as Oct-3/4 or Pouf51), Sox1, Sox2, Sox3, Sox 15, Sox 18, NANOG, Klf1, Klf2, Klf4, Klf5, NR5A2, c-Myc, l-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not effected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., Cell-Stem Cell 2:525-528 (2008); Huangfu et al., Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9, 10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbxl5, Ecat1, Esg1, Eras, Gdf3, Fgf4, Cripto, Dax1, Zpf296, Slc2a3, Rex1, Utf1, and Nat1. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but can also include detection of protein markers. Intracellular markers may be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Creating Patient Specific iPSCs

One step of the ex vivo methods of the present disclosure can involve creating a patient specific iPS cell, patient specific iPS cells, or a patient specific iPS cell line. There are many established methods in the art for creating patient specific iPS cells, as described in Takahashi and Yamanaka 2006; Takahashi, Tanabe et al. 2007. For example, the creating step can comprise: a) isolating a somatic cell, such as a skin cell or fibroblast, from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX2, KLF4, Lin28, NANOG, and cMYC.

Performing a Biopsy or Aspirate of the Patient's Bone Marrow

A biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate can be performed according to any of the known methods in the art. For example, in a bone marrow aspirate, a large needle is used to enter the pelvis bone to collect bone marrow.

Isolating a Mesenchymal Stem Cell

Mesenchymal stem cells can be isolated according to any method known in the art, such as from a patient's bone marrow or peripheral blood. For example, marrow aspirate can be collected into a syringe with heparin. Cells can be washed and centrifuged on a Percoll™ density gradient. Cells, such as blood cells, liver cells, interstitial cells, macrophages, mast cells, and thymocytes, can be separated using density gradient centrifugation media, Percoll™. The cells can be cultured in Dulbecco's modified Eagle's medium (DMEM) (low glucose) containing 10% fetal bovine serum (FBS) (Pittinger M F, Mackay A M, Beck S C et al., Science 1999; 284:143-147).

Treating a Patient with GCSF

A patient may optionally be treated with granulocyte colony stimulating factor (GCSF) in accordance with any method known in the art. The GCSF can be administered in combination with Plerixaflor.

Isolating a Hematopoietic Progenitor Cell from a Patient

A hematopoietic progenitor cell can be isolated from a patient by any method known in the art. CD34+ cells can be enriched using CliniMACS® Cell Selection System (Miltenyi Biotec). CD34+ cells can be weakly stimulated in serum-free medium (e.g., CellGrow SCGM media, CellGenix) with cytokines (e.g., SCF, rhTPO, rhFLT3) before genome editing.

Human Hematopoietic Stem and Progenitor Cells

In some embodiments, the genetically modified cells of the present disclosure are human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines (in particular granulocyte colony-stimulating factor; G-CSF), some myelosuppressive drugs used in cancer treatment, and compounds that disrupt the interaction between hematopoietic and BM stromal cells can rapidly mobilize large numbers of stem and progenitors into the circulation.

In some embodiments of the present disclosure, G-CSF is used in a subject to improve stem cell mobilization, while in other embodiments, plerixafor (Mozobil®) is used. In some embodiments, plerixafor is used in combination with G-CSF. Plerixafor is discussed in more detail below.

The best known marker of human HSPCs is the cell surface glycoprotein CD34. CD34 is routinely used to identify and isolate hHSPCs for use clinically in bone marrow transplantation. Thus, herein, the hHSPCs of the drug product are referred to as modified CD34+ hHSPCs.

Delivery

Guide RNA polynucleotides (RNA or DNA) and/or endonuclease polynucleotide(s) (RNA or DNA) can be delivered by viral or non-viral delivery vehicles known in the art, such as electroporation, mechanical force, cell deformation (SQZ Biotech), and cell penetrating peptides. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Electroporation is a delivery technique in which an electrical field is applied to one or more cells in order to increase the permeability of the cell membrane, which allows substances such as drugs, nucleic acids (genome-targeting nucleic acids), proteins (site-directed polypeptides), or RNPs, to be introduced into the cell. In general, electroporation works by passing thousands of volts across a distance of one to two millimeters of suspended cells in an electroporation cuvette (1.0-1.5 kV, 250-750V/cm).

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

Polynucleotides, such as guide RNA, sgRNA, and mRNA encoding an endonuclease, can be delivered to a cell or a patient by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

As stated previously, the site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA and tracrRNA can be generally combined in a 1:1:1 molar ratio. However, a wide range of molar ratios can be used to produce a RNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 2.

TABLE 2

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. See Table 3.

TABLE 3

| Tissue/Cell Type | Serotype |
| --- | --- |
| Liver | AAV3, AAV5, AAV8, AAV9 |
| Skeletal muscle | AAV1, AAV7, AAV6, AAV8, AAV9 |
| Central nervous system | AAV1, AAV4, AAV5, AAV8, AAV9 |
| RPE | AAV5, AAV4, AAV2, AAV8, AAV9, AAVrh8R |
| Photoreceptor cells | AAV5, AAV8, AAV9, AAVrh8R |
| Lung | AAV9, AAV5 |
| Heart | AAV8 |
| Pancreas | AAV8 |
| Kidney | AAV2, AA8 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirusr, poxvirus, vaccinia virus, and herpes simplex virus.

In some cases, Cas9 mRNA, sgRNA targeting one or two loci within or near the BCL11A gene or other DNA sequence that encodes a regulatory element of the BCL11A gene can each be separately formulated into lipid nanoparticles, or are all co-formulated into one lipid nanoparticle.

In some cases, Cas9 mRNA can be formulated in a lipid nanoparticle, while sgRNA can be delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV. A range of non-viral delivery methods also exist that can deliver each of these components, or non-viral and viral methods can be employed in tandem. For example, nano-particles can be used to deliver the protein and guide RNA.

Successive Gene Editing

In some embodiments, the present disclosure utilizes multiple, successive gene editing steps. In some embodiments, successive gene editing steps involve the use of multiple, successive or sequential electroporations to introduce gene editing compositions, e.g., gRNA(s) and CRISPR endonucleases (e.g., Cas9 or Cpf1).

In some embodiments, each successive gene editing step (e.g., each electroporation step) involves use the same compositions, e.g., use the same gRNA(s) and same CRISPR endonuclease(s). In other embodiments, successive gene editing steps (e.g., successive electroporation steps) involve different compositions, e.g., use of different gRNA(s) and/or different CRISPR endonuclease(s). In some embodiments, each successive gene editing step (e.g., each electroporation step) targets the same chromosomal locus. In other embodiments, successive gene editing steps (e.g., successive electroporation steps) target different chromosomal loci. In some embodiments, successive gene editing steps (e.g., successive electroporation steps) involve targeting of one or more BCL11A-related loci on chromosome 2.

In some embodiments, successive gene editing (e.g., successive electroporation) may involve 2, 3, 4, 5, 6, or more gene editing steps. In some embodiments, successive gene editing may involve 2 gene editing steps. In some embodiments, successive gene editing may involve 3 gene editing steps.

In some embodiments, successive gene editing steps (e.g., successive electroporation steps) provide improved persistence of gene editing, higher levels of gene editing, improved biological outcomes, e.g., increased levels of HbF, fewer off-target effects, and/or fewer translocations, compared to single gene editing events. In some embodiments, successive gene editing steps (e.g., successive electroporation steps) provide fewer translocations compared to single gene editing events (e.g., a single electroporation step).

In some embodiments, successive gene editing steps (e.g., successive electroporation steps) may occur 12, 18, 24, 36, 48, 72, or more hours apart from one another, e.g., a second electroporation may occur 48 hours after a first electroporation. In some embodiments, successive gene editing steps (e.g., successive electroporation steps) occur 12-72, 12-48, or 36-72 hours apart from one another. In some embodiments, successive gene editing steps (e.g., successive electroporation steps) occur 36 hours apart. In some embodiments, successive gene editing steps (e.g., successive electroporation steps) occur 48 hours apart.

In some embodiments, a first gene editing step (e.g., a first successive electroporation step) may occur within 12, 36, 48, or 72 of thawing a population of cells or obtaining a population of cells from a biological source, e.g., a human subject or human patient.

In some embodiments, a population of edited cells may be purified, e.g., using FACS, between two successive gene editing steps, e.g., between a first and second electroporation, or after completing a series of successive gene editing steps (e.g., a series of successive electroporation steps). In some embodiments, a population of cells may be allowed to differentiate and/or enucleate between two successive gene editing steps (e.g., successive electroporation steps) or after completing a series of successive gene editing steps (e.g., successive electroporation steps).

In some embodiments, successive gene editing steps (e.g., successive electroporation steps) may be performed on any cell type described herein, e.g., HSPC, mPB CD34+. In some embodiments, successive gene editing steps (e.g., successive electroporation steps) may be performed on myeloid progenitor cells.

Genetically Modified Cells

The term "genetically modified cell" or "genetically engineered cell" refers to a cell that comprises at least one genetic modification introduced by genome editing (e.g., using the CRISPR/Cas9/Cpf1 system). In some ex vivo examples herein, the genetically modified cell can be genetically modified progenitor cell. In some in vivo examples herein, the genetically modified cell can be a genetically modified hematopoietic progenitor cell. A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure the modulation or inactivation of the transcriptional control sequence of the BCL11A gene or protein expression or activity, for example Western Blot analysis of the of the transcriptional control sequence of the BCL11A gene protein or quantifying of the transcriptional control sequence of the BCL11A gene mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating hemoglobinopathy.

The term "substantially enriched" with respect to a particular cell population, refers to a population of cells that is at least about 10%, about 20%, about 30%, about 40%, about 50%, about 60%, about 70% or more with respect to the cells making up a total cell population.

The term "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

In some embodiments, a genetically engineered cell or population thereof comprises a genetic mutation, which is a permanent insertion, deletion, modulation, or an inactivation of a transcriptional control sequence of a BCL11A gene. In some embodiments, a genetically engineered cell comprises a genetic mutation at one or more sites targeted by one or more sgRNAs. In some embodiments, a genetically engineered cell comprises a genetic modification wherein the genetic mutation occurs at one or more sites targeted by a sgRNA comprising the nucleic acid sequence of SEQ ID NO: 11. In some embodiments, a genetically engineered cell comprises a genetic modification wherein the genetic modification occurs at one or more sites targeted by a sgRNA comprising the nucleic acid sequence of SEQ ID NO: 12. In some embodiments, a genetically engineered cell comprises one, two or more genetic modifications wherein the genetic modification(s) occur at one or more sites targeted by a first sgRNA comprising the nucleic acid sequence of SEQ ID NO: 11 and a second sgRNA comprising the nucleic acid sequence of SEQ ID NO: 12. In some embodiments, a genetically engineered cell comprises one, two or more genetic modifications wherein the genetic modification(s) occur at one or more sites targeted by a first sgRNA comprising the nucleic acid sequence of SEQ ID NO: 11 and a second sgRNA comprising the nucleic acid sequence of SEQ ID NO: 13. In some embodiments, a genetically engineered cell comprises one, two or more genetic modifications wherein the genetic modification(s) occur at one or more sites targeted by a first sgRNA comprising the nucleic acid sequence of SEQ ID NO: 12 and a second sgRNA comprising the nucleic acid sequence of SEQ ID NO: 13.

In some embodiments, a genetically engineered cell is a CD34+ human cell. In some embodiments, a genetically engineered cell is a CD34+ human hematopoietic stem and progenitor cell. In some embodiments, a population of genetically engineered cells are CD34+ human cells. In some embodiments, a population of genetically engineered cells are CD34+ human hematopoietic stem and progenitor cells.

In some embodiments, a genetically engineered cell or population thereof exhibit a HbF mean percentage of HbF/(HbF+HbA) protein levels of at least 10%, at least 11%, at least 12%, at least 13%, at least 14%, at least 15%, at least 20%, at least 25%, at least 30%, at least 35%, at least 40%, at least 45%, or at least 50%. In some embodiments, a genetically engineered cell or population thereof exhibit a HbF mean percentage of HbF/(HbF+HbA) protein levels of between 10% and 70%, between 20% and 60%, or between 30% and 55%.

In some embodiments, a genetically engineered cell or population thereof exhibit a mean allele editing frequency of 30% to 99%. In some embodiments, a genetically engineered cell or population thereof exhibit a mean allele editing frequency of 70% to 99%. In some embodiments, a genetically engineered cell or population thereof exhibit a mean allele editing frequency of 70% to 90%. In some embodiments, a genetically engineered cell or population thereof exhibit a mean allele editing frequency of at least 30%, at least 35%, at least 40%, at least 45%, at least 50%, at least 55%, at least 60%, at least 65%, at least 70%, at least 75%, at least 80%, at least 85%, at least 90%, or at least 95%.

In some embodiments, at least 50% of a population of genetically engineered cells maintains multi-lineage potential for at least sixteen weeks after administration of the population to a subject. In some embodiments, at least 30%, at least 35%, at least 40%, at least 45%, at least 50%, at least 55%, at least 60%, at least 65%, at least 70%, at least 75%, at least 80%, at least 85%, at least 85%, at least 90%, or at least 95% of the population maintain multi-lineage potential for at least sixteen (e.g., 16, 17, 18, 19, 20) weeks after administration of the population of genetically engineered cells to a subject.

In some embodiments, a genetically engineered cell or population thereof exhibit an on-target indel rate of at least 80%. In some embodiments, a genetically engineered cell or population thereof exhibit an on-target indel rate of at least 40%, at least 45%, at least 50%, at least 55%, at least 60%, at least 65%, at least 70%, at least 75%, at least 80%, at least 85%, at least 90%, or at least 95%.

In some embodiments, a genetically engineered cell or population thereof exhibit an off-target indel rate of less than 5%, or less than 1%. In some embodiments, a genetically engineered cell or population thereof exhibit an off-target indel rate of less than 0.9%, less than 0.8%, 0.7%, 0.6%, 0.5%, 0.4%, 0.3%, 0.2%, or 0.1%.

In some embodiments, a population of genetically engineered cells comprises cells having at least two (e.g., 2, 3, 4, 5, 6 or more) different genetic mutations.

Differentiation of Genome-Edited iPSCs into Hematopoietic Progenitor Cells

Another step of the ex vivo methods of the present disclosure can comprise differentiating the genome-edited iPSCs into hematopoietic progenitor cells. The differentiating step can be performed according to any method known in the art.

Differentiation of Genome-Edited Mesenchymal Stem Cells into Hematopoietic Progenitor Cells Another step of the ex vivo methods of the present disclosure can comprise differentiating the genome-edited mesenchymal stem cells into hematopoietic progenitor cells. The differentiating step can be performed according to any method known in the art.

Implanting Cells into Patients

Another step of the ex vivo methods of the present disclosure can comprise implanting the cells into patients. This implanting step can be accomplished using any method of implantation known in the art. For example, the genetically modified cells can be injected directly in the patient's blood or otherwise administered to the patient. The genetically modified cells may be purified ex vivo using a selected marker.

Pharmaceutically Acceptable Carriers

The ex vivo methods of administering progenitor cells to a subject contemplated herein can involve the use of therapeutic compositions comprising progenitor cells.

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein can be administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerine, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Administration & Efficacy

The terms "administering," "introducing" and "transplanting" are used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of myogenic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein can be administered to a subject in advance of any symptom of a hemoglobinopathy, e.g., prior to the development of fatigue, shortness of breath, jaundice, slow growth late puberty, joint, bone and chest pain, enlarged spleen and liver. Accordingly, the prophylactic administration of a hematopoietic progenitor cell population serves to prevent a hemoglobinopathy, such as B-thalassemia or Sickle Cell Disease.

When provided therapeutically, hematopoietic progenitor cells are provided at (or after) the onset of a symptom or indication of hemoglobinopathy, e.g., upon the onset of disease.

The hematopoietic progenitor cell population being administered according to the methods described herein can comprise allogeneic hematopoietic progenitor cells obtained from one or more donors. "Allogeneic" refers to a hematopoietic progenitor cell or biological samples comprising hematopoietic progenitor cells obtained from one or more different donors of the same species, where the genes at one or more loci are not identical. For example, a hematopoietic progenitor cell population being administered to a subject can be derived from one more unrelated donor subjects, or from one or more non-identical siblings. In some cases, syngeneic hematopoietic progenitor cell populations can be used, such as those obtained from genetically identical animals, or from identical twins. The hematopoietic progenitor cells can be autologous cells; that is, the hematopoietic progenitor cells are obtained or isolated from a subject and administered to the same subject, i.e., the donor and recipient are the same.

The term "effective amount" refers to the amount of a population of progenitor cells or their progeny needed to prevent or alleviate at least one or more signs or symptoms of hemoglobinopathy, and relates to a sufficient amount of a composition to provide the desired effect, e.g., to treat a subject having hemoglobinopathy. The term "therapeutically effective amount" therefore refers to an amount of progenitor cells or a composition comprising progenitor cells that is sufficient to promote a particular effect when administered to a typical subject, such as one who has or is at risk for hemoglobinopathy. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells comprises at least $10^2$ progenitor cells, at least $5\times10^2$ progenitor cells, at least $10^3$ progenitor cells, at least $5\times10^3$ progenitor cells, at least $10^4$ progenitor cells, at least $5\times10^4$ progenitor cells, at least $10^5$ progenitor cells, at least $2\times10^5$ progenitor cells, at least $3\times10^5$ progenitor cells, at least $4\times10^5$ progenitor cells, at least $5\times10^5$ progenitor cells, at least $6\times10^5$ progenitor cells, at least $7\times10^5$ progenitor cells, at least $8\times10^5$ progenitor cells, at least $9\times10^5$ progenitor cells, at least $1\times10^6$ progenitor cells, at least $2\times10^6$ progenitor cells, at least $3\times10^6$ progenitor cells, at least $4\times10^6$ progenitor cells, at least $5\times10^6$ progenitor cells, at least $6\times10^6$ progenitor cells, at least $7\times10^6$ progenitor cells, at least $8\times10^6$ progenitor cells, at least $9\times10^6$ progenitor cells, or multiples thereof. The progenitor cells can be derived from one or more donors, or can be obtained from an autologous source. In some examples described herein, the progenitor cells can be expanded in culture prior to administration to a subject in need thereof.

"Administered" refers to the delivery of a progenitor cell composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1\times10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells can be administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a treatment comprising a composition for the treatment of hemoglobinopathies can be determined by the skilled clinician. However, a treatment is considered "effective treatment," if any one or all of the signs or symptoms of, as but one example, levels of functional BCL11A and functional HbF are altered in a beneficial manner (e.g., decreased by at least 10% for BCL11A and/or increased by at least 10% for HbF), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with hemoglobinopathies by decreasing the amount of functional BCL11A and/or increasing the amount of functional HbF in the individual. Early signs typically associated with hemoglobinopathies include for example, fatigue, shortness of breath, jaundice, slow growth late puberty, joint, bone and chest pain, enlarged spleen and liver.

Kits

The present disclosure provides kits for carrying out the methods described herein. A kit can include one or more of a genome-targeting nucleic acid, a polynucleotide encoding a genome-targeting nucleic acid, a site-directed polypeptide, a polynucleotide encoding a site-directed polypeptide, and/ or any nucleic acid or proteinaceous molecule necessary to carry out the aspects of the methods described herein, or any combination thereof.

A kit can comprise: (1) a vector comprising a nucleotide sequence encoding a genome-targeting nucleic acid, (2) the site-directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleotide sequence encoding a genome-targeting nucleic acid, and (ii) a nucleotide sequence encoding the site-directed polypeptide; and (2) a reagent for reconstitution and/or dilution of the vector.

In any of the above kits, the kit can comprise a single-molecule guide genome-targeting nucleic acid. In any of the above kits, the kit can comprise a double-molecule genome-targeting nucleic acid. In any of the above kits, the kit can comprise two or more double-molecule guides or single-molecule guides. The kits can comprise a vector that encodes the nucleic acid targeting nucleic acid.

In any of the above kits, the kit can further comprise a polynucleotide to be inserted to effect the desired genetic modification.

Components of a kit can be in separate containers, or combined in a single container.

Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

In some embodiments, a kit may comprise at least two guide RNAs (gRNAs). In some embodiments, a kit may comprise three gRNAs. In some embodiments, a kit may comprise a gRNA comprising a spacer sequence of SEQ ID NO: 6, optionally wherein any or all T's in the sequence is/are replaced with U's. In some embodiments, a kit may comprise a gRNA comprising a spacer sequence of SEQ ID NO: 7, optionally wherein any or all T's in the sequence is/are replaced with U's. In some embodiments, a kit may comprise a gRNA comprising a spacer sequence of SEQ ID NO: 14. In some embodiments, a kit may comprise a first gRNA comprising a spacer sequence of SEQ ID NO: 6, optionally wherein any or all T's in the sequence is/are replaced with U's, and a second gRNA comprising a spacer sequence of SEQ ID NO: 7, optionally wherein any or all T's in the sequence is/are replaced with U's. In some embodiments, a kit may comprise a first gRNA comprising a spacer sequence of SEQ ID NO: 6, optionally wherein any or all T's in the sequence is/are replaced with U's, and a second gRNA comprising a spacer sequence of SEQ ID NO: 14. In some embodiments, a kit may comprise a first gRNA comprising a spacer sequence of SEQ ID NO: 7, optionally wherein any or all T's in the sequence is/are replaced with U's, and a second gRNA comprising a spacer sequence of SEQ ID NO: 14. In some embodiments, a kit may comprise a first gRNA comprising a spacer sequence of SEQ ID NO: 6; optionally wherein any or all T's in the sequence is/are replaced with U's; a second gRNA comprising a spacer sequence of SEQ ID NO: 7, optionally wherein any or all T's in the sequence is/are replaced with U's; and a third gRNA comprising a spacer sequence of SEQ ID NO: 14. In some embodiments, a kit may comprise a gRNA comprising the nucleotide sequence of SEQ ID NO: 11. In some embodiments, a kit may comprise a gRNA comprising the nucleotide sequence of SEQ ID NO: 12. In some embodiments, a kit may comprise a gRNA comprising the nucleotide sequence of SEQ ID NO: 13. In some embodiments, a kit may comprise a first gRNA comprising the nucleotide sequence of SEQ ID NO: 11 and a second gRNA comprising the nucleotide sequence of SEQ ID NO: 12. In some embodiments, a kit may comprise a first gRNA comprising the nucleotide sequence of SEQ ID NO: 11 and a second gRNA comprising the nucleotide sequence of SEQ ID NO: 13. In some embodiments, a kit may comprise a first gRNA comprising the nucleotide sequence of SEQ ID NO: 12 and a second gRNA comprising the nucleotide sequence of SEQ ID NO: 13. In some embodiments, a kit may comprise a first gRNA comprising the nucleotide sequence of SEQ ID NO: 11, a second gRNA comprising the nucleotide sequence of SEQ ID NO: 12, and a third gRNA comprising the nucleotide sequence of SEQ ID NO: 13. In some embodiments, a kit may comprise at least one modified gRNA. In some embodiments, a kit may comprise at least two modified gRNAs. In some embodiments, a kit may comprise at least three modified gRNAs.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Other Possible Therapeutic Approaches

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR-Cas9 nuclease systems. The nuclease platforms vary in difficulty of design, targeting density and mode of action, particularly as the specificity of ZFNs and TALENs is through protein-DNA interactions, while RNA-DNA interactions primarily guide Cas9. Cas9 cleavage also requires an adjacent motif, the PAM, which differs between different CRISPR systems. Cas9 from *Streptococcus pyogenes* cleaves using a NGG PAM, CRISPR from *Neisseria meningitidis* can cleave at sites with PAMs including NNNNGATT, NNNNNGTTT and NNNNGCTT. A number of other Cas9 orthologs target protospacer adjacent to alternative PAMs.

CRISPR endonucleases, such as Cas9, can be used in the methods of the present disclosure. However, the teachings described herein, such as therapeutic target sites, could be applied to other forms of endonucleases, such as ZFNs, TALENs, HEs, or MegaTALs, or using combinations of nulceases. However, in order to apply the teachings of the present disclosure to such endonucleases, one would need to, among other things, engineer proteins directed to the specific target sites.

Additional binding domains can be fused to the Cas9 protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Natl Acad Sci USA* 96(6):2758-63 (1999); Dreier B et al., *J Mol Biol.* 303(4):489-502 (2000); Liu Q et al., *J Biol Chem.* 277(6):3850-6 (2002); Dreier et al., *J Biol Chem* 280(42): 35588-97 (2005); and Dreier et al., *J Biol Chem.* 276(31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp.

TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, *Science* 326(5959):1509-12 (2009); Mak et al., *Science* 335(6069):716-9 (2012); and Moscou et al., *Science* 326(5959):1501 (2009). The use of TALENs based on the "Golden Gate" platform, or cloning scheme, has been described by multiple groups; see, e.g., Cermak et al., *Nucleic Acids Res.* 39(12):e82 (2011); Li et al., *Nucleic Acids Res.* 39(14):6315-25(2011); Weber et al., *PLoS One.* 6(2):e16765 (2011); Wang et al., *J Genet Genomics* 41(6): 339-47, Epub 2014 May 17 (2014); and Cermak T et al., *Methods Mol Biol.* 1239:133-59 (2015).

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including LAGLI-DADG (SEQ ID NO. 2), GIY-YIG, His-Cis box, H—N—H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., *Glycobiology* 24(8):663-80 (2014); Belfort and Bonocora, *Methods Mol Biol.* 1123: 1-26 (2014); Hafez and Hausner, *Genome* 55(8):553-69 (2012); and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., *NAR* 42: 2591-2601 (2014); Kleinstiver et al., G3 4:1155-65 (2014); and Boissel and Scharenberg, *Methods Mol. Biol.* 1239: 171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., *NAR* 42, 8816-29 (2014). It is anticipated that other combinations of existing nuclease-based approaches will evolve and be useful in achieving the targeted genome modifications described herein.

dCas9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., *Nature Biotech* 32: 569-76 (2014); and Guilinger et al., *Nature Biotech.* 32: 577-82 (2014). Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

On- and Off-Target Mutation Detection by Sequencing

To sequence on-target sites and putative off-target sites, the appropriate amplification primers were identified and reactions were set up with these primers using the genomic DNA harvested using QuickExtract DNA extraction solution (Epicentre) from treated cells three days post-transfection. The amplification primers contain the gene specific portion flanked by adapters. The forward primer's 5' end includes a modified forward (read1) primer-binding site. The reverse primer's 5' end contains a combined modified reverse (read2) and barcode primer-binding site, in opposite orientation. The individual PCR reactions were validated by separating on agarose gels, then purified and re-amplified. The second round forward primers contain the Illumina P5 sequence, followed by a proportion of the modified forward (read1) primer binding site. The second round reverse primers contain the Illumina P7 sequence (at the 5' end), followed by the 6-base barcode and the combined modified reverse (read2) and barcode primer binding site. The second round amplifications were also checked on agarose gels, then purified, and quantitated using a NanoDrop spectrophotometer. The amplification products were pooled to match concentration and then submitted to the Emory Integrated Genomic core for library prepping and sequencing on an Illumina Miseq machine.

The sequencing reads were sorted by barcode and then aligned to the reference sequences supplied by bioinformatics for each product. Insertion and deletion rates in the aligned sequencing reads were detected in the region of the putative cut sites using software previously described; see, e.g., Lin et al., *Nucleic Acids Res.*, 42: 7473-7485 (2014). The levels of insertions and deletions detected in this window were then compared to the level seen in the same location in genomic DNA isolated from in mock transfected cells to minimize the effects of sequencing artifacts.

Mutation Detection Assays

The on- and off-target cleavage activities of Cas9 and guide RNA combinations were measured using the mutation rates resulting from the imperfect repair of double-strand breaks by NHEJ.

On-target loci were amplified using AccuPrime Taq DNA Polymerase High Fidelity (Life Technologies, Carlsbad, Calif.) following manufacturer's instructions for 40 cycles (94° C., 30 s; 52-60° C., 30 s; 68° C., 60 s) in 50 µl reactions containing 1 µl of the cell lysate, and 1 µl of each 10 µM amplification primer. T7EI mutation detection assays were performed, as per manufacturers protocol [Reyon et al., *Nat. Biotechnol.*, 30: 460-465 (2012)], with the digestions separated on 2% agarose gels and quantified using ImageJ [Guschin et al., *Methods Mol. Biol.*, 649: 247-256 (2010)]. The assays determine the percentage of insertions/deletions ("indels") in the bulk population of cells.

Methods, Compositions, and Therapeutics of the Invention

Accordingly, the present disclosure relates in particular to the following non-limiting embodiments:

In a first method, Method 1, the present disclosure provides a method for editing a B-cell lymphoma 11A (BCL11A) gene in a human cell by genome editing, the method comprising: introducing into the human cell one or more deoxyribonucleic acid (DNA) endonucleases to effect one or more single-strand breaks (SSBs) or double-strand breaks (DSBs), within or near the BCL11A gene or other DNA sequence that encodes a regulatory element of the BCL11A gene, that results in at least one of a permanent insertion, deletion, modulation, and an inactivation of a transcriptional control sequence of the BCL11A gene.

In another method, Method 2, the present disclosure provides a method for editing a BCL11A gene in a human cell by genome editing, as provided in Method 1, wherein the transcriptional control sequence is located within a second intron of the BCL11A gene.

In another method, Method 3, the present disclosure provides a method for editing a BCL11A gene in a human cell by genome editing, as provided in any one of Methods 1 or 2, wherein the transcriptional control sequence is located within one or more of: a +55 DNase I hypersensitive site (DHS) of the BCL11A gene, a +58 DHS of the BCL11A gene, and a +62 DHS of the BCL11A gene.

In another method, Method 4, the present disclosure provides an ex vivo method for treating a patient with a hemoglobinopathy, the method comprising: editing within or near a B-cell lymphoma 11A (BCL11A) gene or other DNA sequence that encodes a regulatory element of the BCL11A gene of an induced pluripotent stem cell (iPSC); differentiating the genome-edited iPSC into a hematopoietic progenitor cell; and implanting the hematopoietic progenitor cell into the patient.

In another method, Method 5, the present disclosure provides an ex vivo method for treating a patient with a hemoglobinopathy, as provided in Method 4, further comprising: creating the iPSC, wherein the creating step comprises: isolating a somatic cell from the patient; and introducing a set of pluripotency-associated genes into the somatic cell to induce the somatic cell to become the iPSC.

In another method, Method 6, the present disclosure provides an ex vivo method for treating a patient with a hemoglobinopathy, as provided in Method 5, wherein the somatic cell is a fibroblast.

In another method, Method 7, the present disclosure provides an ex vivo method for treating a patient with a hemoglobinopathy, as provided in Method 5, wherein the set of pluripotency-associated genes is one or more of the genes selected from the group consisting of: OCT4, SOX2, KLF4, Lin28, NANOG and cMYC.

In another method, Method 8, the present disclosure provides an ex vivo method for treating a patient with a hemoglobinopathy, as provided in any one of Methods 4-7, wherein the editing step comprises: introducing into the iPSC one or more DNA endonucleases to effect one or more SSBs or DSBs within or near the BCL11A gene or other DNA sequence that encodes a regulatory element of the BCL11A gene that results in at least one of a permanent insertion, deletion, modulation, and an inactivation of a transcriptional control sequence of the BCL11A gene.

In another method, Method 9, the present disclosure provides an ex vivo method for treating a patient with a hemoglobinopathy, as provided in Method 8, wherein the transcriptional control sequence is located within a second intron of the BCL11A gene.

In another method, Method 10, the present disclosure provides an ex vivo method for treating a patient with a hemoglobinopathy, as provided in any one of Methods 8 or 9, wherein the transcriptional control sequence is located within one or more of: a +55 DHS of the BCL11A gene, a +58 DHS of the BCL11A gene, and a +62 DHS of the BCL11A gene.

In another method, Method 11, the present disclosure provides an ex vivo method for treating a patient with a hemoglobinopathy, as provided in any one of Methods 4-10, wherein the differentiating step comprises one or more of the following to differentiate the genome-edited iPSC into a hematopoietic progenitor cell: treatment with a combination of small molecules, delivery of master transcription factors, delivery of mRNA encoding master transcription factors, or delivery of mRNA encoding transcription factors.

In another method, Method 12, the present disclosure provides an ex vivo method for treating a patient with a hemoglobinopathy, as provided in any one of Methods 4-11, wherein the implanting step comprises implanting the hematopoietic progenitor cell into the patient by transplantation, local injection, systemic infusion, or combinations thereof.

In another method, Method 13, the present disclosure provides an ex vivo method for treating a patient with a hemoglobinopathy, the method comprising: editing within or near a B-cell lymphoma 11A (BCL11A) gene or other DNA sequence that encodes a regulatory element of the BCL11A gene of a mesenchymal stem cell; differentiating the genome-edited mesenchymal stem cell into a hematopoietic progenitor cell; and implanting the hematopoietic progenitor cell into the patient.

In another method, Method 14, the present disclosure provides an ex vivo method for treating a patient with a hemoglobinopathy, as provided in Method 13, further comprising: isolating the mesenchymal stem cell from the patient, wherein the mesenchymal stem cell is isolated from the patient's bone marrow or peripheral blood.

In another method, Method 15, the present disclosure provides an ex vivo method for treating a patient with a hemoglobinopathy, as provided in Method 14, wherein the isolating step comprises: aspiration of bone marrow and isolation of mesenchymal cells using density gradient centrifugation media.

In another method, Method 16, the present disclosure provides an ex vivo method for treating a patient with a hemoglobinopathy, as provided in any one of Methods 13-15, wherein the editing step comprises: introducing into the mesenchymal stem cell one or more DNA endonucleases to effect one or more SSBs or DSBs within or near the BCL11A gene or other DNA sequence that encodes a regulatory element of the BCL11A gene that results in at least one of a permanent insertion, deletion, modulation, and an inactivation of a transcriptional control sequence of the BCL11A gene.

In another method, Method 17, the present disclosure provides an ex vivo method for treating a patient with a hemoglobinopathy, as provided in Method 16, wherein the transcriptional control sequence is located within a second intron of the BCL11A gene.

In another method, Method 18, the present disclosure provides an ex vivo method for treating a patient with a hemoglobinopathy, as provided in any one of Methods 16 or 17, wherein the transcriptional control sequence is located within one or more of: a +55 DHS of the BCL11A gene, a +58 DHS of the BCL11A gene, and a +62 DHS of the BCL11A gene.

In another method, Method 19, the present disclosure provides an ex vivo method for treating a patient with a hemoglobinopathy, as provided in any one of Methods 13-18, wherein the differentiating step comprises one or more of the following to differentiate the genome-edited mesenchymal stem cell into a hematopoietic progenitor cell: treatment with a combination of small molecules, delivery of master transcription factors, delivery of mRNA encoding master transcription factors, or delivery of mRNA encoding transcription factors.

In another method, Method 20, the present disclosure provides an ex vivo method for treating a patient with a hemoglobinopathy, as provided in any one of Methods 13-19, wherein the implanting step comprises implanting the hematopoietic progenitor cell into the patient by transplantation, local injection, systemic infusion, or combinations thereof.

In another method, Method 21, the present disclosure provides an ex vivo method for treating a patient with a hemoglobinopathy, the method comprising: editing within or near a B-cell lymphoma 11A (BCL11A) gene or other DNA sequence that encodes a regulatory element of the BCL11A gene of a hematopoietic progenitor cell; and implanting the genome-edited hematopoietic progenitor cell into the patient.

In another method, Method 22, the present disclosure provides an ex vivo method for treating a patient with a hemoglobinopathy, as provided in Method 21, further comprising: isolating the hematopoietic progenitor cell from the patient.

In another method, Method 23, the present disclosure provides an ex vivo method for treating a patient with a hemoglobinopathy, as provided in Method 22, wherein the method further comprises treating the patient with granulocyte colony stimulating factor (GCSF) prior to the isolating step.

In another method, Method 24, the present disclosure provides an ex vivo method for treating a patient with a hemoglobinopathy, as provided in Method 23, wherein the treating step is performed in combination with 1,1'-(1,4-phenylenebismethylene)bis(1,4,8,11-tetraazacyclotetradecane).

In another method, Method 25, the present disclosure provides an ex vivo method for treating a patient with a hemoglobinopathy, as provided in any one of Methods 22-24, wherein the isolating step comprises isolating CD34+ cells.

In another method, Method 26, the present disclosure provides an ex vivo method for treating a patient with a hemoglobinopathy, as provided in any one of Methods 21-25, wherein the editing step comprises: introducing into the hematopoietic progenitor cell one or more DNA endonucleases to effect one or more SSBs or DSBs within or near the BCL11A gene or other DNA sequence that encodes a regulatory element of the BCL11A gene that results in at least one of a permanent insertion, deletion, modulation, and an inactivation of a transcriptional control sequence of the BCL11A gene.

In another method, Method 27, the present disclosure provides an ex vivo method for treating a patient with a hemoglobinopathy, as provided in Method 26, wherein the transcriptional control sequence is located within a second intron of the BCL11A gene.

In another method, Method 28, the present disclosure provides an ex vivo method for treating a patient with a hemoglobinopathy, as provided in any one of Methods 26 or 27, wherein the transcriptional control sequence is located within one or more of: a +55 DHS of the BCL11A gene, a +58 DHS of the BCL11A gene, and a +62 DHS of the BCL11A gene.

In another method, Method 29, the present disclosure provides an ex vivo method for treating a patient with a hemoglobinopathy, as provided in any one of Methods 21-28, wherein the implanting step comprises implanting the genome-edited hematopoietic progenitor cell into the patient by transplantation, local injection, systemic infusion, or combinations thereof.

In another method, Method 30, the present disclosure provides an in vivo method for treating a patient with a hemoglobinopathy, the method comprising: editing a BCL11A gene in a cell of the patient.

In another method, Method 31, the present disclosure provides an in vivo method for treating a patient with a hemoglobinopathy, as provided in Method 30, wherein the editing step comprises introducing into the cell one or more DNA endonucleases to effect one or more SSBs or DSBs within or near the BCL11A gene or other DNA sequence that encodes a regulatory element of the BCL11A gene that results in at least one of a permanent insertion, deletion, modulation, and an inactivation of a transcriptional control sequence of the BCL11A gene.

In another method, Method 32, the present disclosure provides an in vivo method for treating a patient with a hemoglobinopathy, as provided in Method 31, wherein the transcriptional control sequence is located within a second intron of the BCL11A gene.

In another method, Method 33, the present disclosure provides an in vivo method for treating a patient with a hemoglobinopathy, as provided in any one of Methods 31 or 32, wherein the transcriptional control sequence is located within one or more of: a +55 DHS of the BCL11A gene, a +58 DHS of the BCL11A gene, and a +62 DHS of the BCL11A gene.

In another method, Method 34, the present disclosure provides an in vivo method for treating a patient with a hemoglobinopathy, as provided in any one of Methods 30-33, wherein the cell is a bone marrow cell, a hematopoietic progenitor cell, or a CD34+ cell.

In another method, Method 35, the present disclosure provides a method for treating a patient with a hemoglobinopathy, as provided in any one of Methods 1, 8, 16, 26, or 31, wherein the one or more DNA endonucleases is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized versions thereof, or modified versions thereof, and combinations thereof.

In another method, Method 36, the present disclosure provides a method for treating a patient with a hemoglobinopathy, as provided in Method 35, wherein the method comprises introducing into the cell one or more polynucleotides encoding the one or more DNA endonucleases.

In another method, Method 37, the present disclosure provides a method for treating a patient with a hemoglobinopathy, as provided in Method 35, wherein the method comprises introducing into the cell one or more RNAs encoding the one or more DNA endonucleases.

In another method, Method 38, the present disclosure provides a method for treating a patient with a hemoglobinopathy, as provided in any one of Methods 36 or 37, wherein the one or more polynucleotides or one or more RNAs is one or more modified polynucleotides or one or more modified RNAs.

In another method, Method 39, the present disclosure provides a method for treating a patient with a hemoglobinopathy, as provided in Method 35, wherein the one or more DNA endonuclease is one or more proteins or polypeptides.

In another method, Method 40, the present disclosure provides a method for treating a patient with a hemoglobinopathy, as provided in Method 39, wherein the one or more proteins or polypeptides is flanked at the N-terminus, the C-terminus, or both the N-terminus and C-terminus by one or more NLSs.

In another method, Method 41, the present disclosure provides a method for treating a patient with a hemoglobinopathy, as provided in Method 39, wherein the one or more proteins or polypeptides is flanked by two NLSs, one NLS located at the N-terminus and the second NLS located at the C-terminus.

In another method, Method 42, the present disclosure provides a method for treating a patient with a hemoglobinopathy, as provided in any one of Methods 40-41, wherein the one or more NLSs is a SV40 NLS.

In another method, Method 43, the present disclosure provides a method for treating a patient with a hemoglobinopathy, as provided in any one of Methods 1-42, wherein the method further comprises introducing into the cell one or more gRNAs.

In another method, Method 44, the present disclosure provides a method for treating a patient with a hemoglobinopathy, as provided in Method 43, wherein the one or more gRNAs are sgRNAs.

In another method, Method 45, the present disclosure provides a method for treating a patient with a hemoglobinopathy, as provided in any one of Methods 43 or 44, wherein the one or more gRNAs or one or more sgRNAs is one or more modified gRNAs or one or more modified sgRNAs.

In another method, Method 46, the present disclosure provides a method for treating a patient with a hemoglobinopathy, as provided in Method 45, wherein the one or more modified sgRNAs comprises three 2'-O-methyl-phosphorothioate residues at or near each of its 5' and 3' ends.

In another method, Method 47, the present disclosure provides a method for treating a patient with a hemoglobinopathy, as provided in Method 46, wherein the modified sgRNA is the nucleic acid sequence of SEQ ID NO: 11.

In another method, Method 48, the present disclosure provides a method for treating a patient with a hemoglobinopathy, as provided in Method 46, wherein the modified sgRNA is the nucleic acid sequence of SEQ ID NO: 12.

In another method, Method 49, the present disclosure provides a method for treating a patient with a hemoglobinopathy, as provided in any one of Methods 43-44, wherein the one or more gRNAs or one or more sgRNAs target a GATA1 site.

In another method, Method 50, the present disclosure provides a method for treating a patient with a hemoglobinopathy, as provided in any one of Methods 43-44, wherein the one or more gRNAs or one or more sgRNAs target an ELF1 site.

In another method, Method 51, the present disclosure provides a method for treating a patient with a hemoglobinopathy, as provided in any one of Methods 43-50, wherein the one or more DNA endonucleases is pre-complexed with one or more gRNAs or one or more sgRNAs to form one or more ribonucleoproteins (RNPs).

In another method, Method 52, the present disclosure provides a method for treating a patient with a hemoglobinopathy, as provided in Method 51, wherein the weight ratio of sgRNA to DNA endonuclease in the RNP is 1:1.

In another method, Method 53, the present disclosure provides a method for treating a patient with a hemoglobinopathy, as provided in Method 52, wherein the sgRNA comprises the nucleic acid sequence of SEQ ID NO: 11, the DNA endonuclease is a S. pyogenes Cas9 comprising a N-terminus SV40 NLS and a C-terminus SV40 NLS, wherein the weight ratio of sgRNA to DNA endonuclease is 1:1.

In another method, Method 54, the present disclosure provides a method for treating a patient with a hemoglobinopathy, as provided in Method 52, wherein the sgRNA comprises the nucleic acid sequence of SEQ ID NO: 12, the DNA endonuclease is a S. pyogenes Cas9 comprising a N-terminus SV40 NLS and a C-terminus SV40 NLS, wherein the weight ratio of sgRNA to DNA endonuclease is 1:1.

In another method, Method 55, the present disclosure provides a method for treating a patient with a hemoglobinopathy, as provided in any one of Methods 1, 8, 16, 26, or 31, wherein the method further comprises: introducing into the cell one gRNA; wherein the one or more DNA endonucleases is one or more Cas9 or Cpf1 endonucleases that effect one single-strand SSB or DSB at a locus within or near the BCL11A gene or other DNA sequence that encodes a regulatory element of the BCL11A gene, and wherein the gRNA comprises a spacer sequence that is complementary to a segment of the locus.

In another method, Method 56, the present disclosure provides a method for treating a patient with a hemoglobinopathy, as provided in any one of Methods 1, 8, 16, 26, or 31, wherein the method further comprises: introducing into the cell one or more gRNAs; wherein the one or more DNA endonucleases is one or more Cas9 or Cpf1 endonucleases that effect or create a pair of SSBs or DSBs, the first at a 5' locus and the second at a 3' locus, within or near the BCL11A gene or other DNA sequence that encodes a regulatory element of the BCL11A gene, and wherein the first guide RNA comprises a spacer sequence that is complementary to a segment of the 5' locus and the second guide RNA comprises a spacer sequence that is complementary to a segment of the 3' locus.

In another method, Method 57, the present disclosure provides a method for treating a patient with a hemoglobinopathy, as provided in any one of Methods 55 or 56, wherein the one or more gRNAs are one or more sgRNAs.

In another method, Method 58, the present disclosure provides a method for treating a patient with a hemoglobinopathy, as provided in any one of Methods 55-57, wherein the one or more gRNAs or one or more sgRNAs is one or more modified gRNAs or one or more modified sgRNAs.

In another method, Method 59, the present disclosure provides a method for treating a patient with a hemoglobinopathy, as provided in Method 58, wherein the one or more modified sgRNA comprises three 2'-O-methyl-phosphorothioate residues at or near each of its 5' and 3' ends.

In another method, Method 60, the present disclosure provides a method for treating a patient with a hemoglobinopathy, as provided in Method 59, wherein the one or more modified sgRNA is the nucleic acid sequence of SEQ ID NO: 11.

In another method, Method 61, the present disclosure provides a method for treating a patient with a hemoglobinopathy, as provided in Method 59, wherein the one or more modified sgRNA is the nucleic acid sequence of SEQ ID NO: 12.

In another method, Method 62, the present disclosure provides a method for treating a patient with a hemoglobinopathy, as provided in any one of Methods 55-57, wherein the one or more gRNAs or one or more sgRNAs target a GATA1 site.

In another method, Method 63, the present disclosure provides a method for treating a patient with a hemoglobinopathy, as provided in any one of Methods 55-57, wherein the one or more gRNAs or one or more sgRNAs target an ELF1 site.

In another method, Method 64, the present disclosure provides a method for treating a patient with a hemoglobinopathy, as provided in any one of Methods 55-63, wherein the one or more Cas9 endonucleases is pre-complexed with one or more gRNAs or one or more sgRNAs to form one or more RNPs.

In another method, Method 65, the present disclosure provides a method for treating a patient with a hemoglobinopathy, as provided in Method 64, wherein the one or more Cas9 endonucleases is flanked at the N-terminus, the C-terminus, or both the N-terminus and C-terminus by one or more NLSs.

In another method, Method 66, the present disclosure provides a method for treating a patient with a hemoglobinopathy, as provided in Method 65, wherein the one or more Cas9 endonucleases is flanked by two NLSs, one NLS located at the N-terminus and the second NLS located at the C-terminus.

In another method, Method 67, the present disclosure provides a method for treating a patient with a hemoglobinopathy, as provided in any one of Methods 65-66, wherein the one or more NLSs is a SV40 NLS.

In another method, Method 68, the present disclosure provides a method for treating a patient with a hemoglobinopathy, as provided in Method 64, wherein the weight ratio of sgRNA to Cas9 endonuclease in the RNP is 1:1.

In another method, Method 69, the present disclosure provides a method for treating a patient with a hemoglobinopathy, as provided in Method 64, wherein the one or more sgRNA comprises the nucleic acid sequence of SEQ ID NO: 11, the Cas9 endonuclease is a *S. pyogenes* Cas9 comprising a N-terminus SV40 NLS and a C-terminus SV40 NLS, wherein the weight ratio of sgRNA to Cas9 endonuclease is 1:1.

In another method, Method 70, the present disclosure provides a method for treating a patient with a hemoglobinopathy, as provided in Method 64, wherein the one or more sgRNA comprises the nucleic acid sequence of SEQ ID NO: 12, the Cas9 endonuclease is a *S. pyogenes* Cas9 comprising a N-terminus SV40 NLS and a C-terminus SV40 NLS, wherein the weight ratio of sgRNA to Cas9 endonuclease is 1:1.

In another method, Method 71, the present disclosure provides a method for treating a patient with a hemoglobinopathy, as provided in any one of Methods 1, 8, 16, 26, or 31, wherein the method further comprises: introducing into the cell two gRNAs; wherein the one or more DNA endonucleases is one or more Cas9 or Cpf1 endonucleases that effect a pair of DSBs, the first at a 5' DSB locus and the second at a 3' DSB locus, within or near the BCL11A gene or other DNA sequence that encodes a regulatory element of the BCL11A gene that causes a deletion of the chromosomal DNA between the 5' DSB locus and the 3' DSB locus that results in a permanent deletion of the chromosomal DNA between the 5'DSB locus and the 3' DSB locus; and wherein the first guide RNA comprises a spacer sequence that is complementary to a segment of the 5' DSB locus and the second guide RNA comprises a spacer sequence that is complementary to a segment of the 3' DSB locus.

In another method, Method 72, the present disclosure provides a method for treating a patient with a hemoglobinopathy, as provided in Method 71, wherein the two gRNAs are two sgRNAs.

In another method, Method 73, the present disclosure provides a method for treating a patient with a hemoglobinopathy, as provided in any one of Methods 71 or 72, wherein the two gRNAs or two sgRNAs are two modified gRNAs or two modified sgRNAs.

In another method, Method 74, the present disclosure provides a method for treating a patient with a hemoglobinopathy, as provided in Method 73, wherein the two modified sgRNAs comprise three 2'-O-methyl-phosphorothioate residues at or near each of its 5' and 3' ends.

In another method, Method 75, the present disclosure provides a method for treating a patient with a hemoglobinopathy, as provided in Method 74, wherein the one modified sgRNA is the nucleic acid sequence of SEQ ID NO: 11.

In another method, Method 76, the present disclosure provides a method for treating a patient with a hemoglobinopathy, as provided in Method 74, wherein the one modified sgRNA is the nucleic acid sequence of SEQ ID NO: 12.

In another method, Method 77, the present disclosure provides a method for treating a patient with a hemoglobinopathy, as provided in any one of Methods 71 or 72, wherein the two gRNAs or two sgRNAs target a GATA1 site.

In another method, Method 78, the present disclosure provides a method for treating a patient with a hemoglobinopathy, as provided in any one of Methods 71 or 72, wherein the two gRNAs or two sgRNAs target an ELF1 site.

In another method, Method 79, the present disclosure provides a method for treating a patient with a hemoglobinopathy, as provided in any one of Methods 71-78, wherein the one or more Cas9 endonucleases is pre-complexed with one or two gRNAs or one or two sgRNAs to form one or more RNPs.

In another method, Method 80, the present disclosure provides a method for treating a patient with a hemoglobinopathy, as provided in Method 79, wherein the one or more Cas9 endonuclease is flanked at the N-terminus, the C-terminus, or both the N-terminus and C-terminus by one or more NLSs.

In another method, Method 81, the present disclosure provides a method for treating a patient with a hemoglobinopathy, as provided in Method 80, wherein the one or more Cas9 endonucleases is flanked by two NLSs, one NLS located at the N-terminus and the second NLS located at the C-terminus.

In another method, Method 82, the present disclosure provides a method for treating a patient with a hemoglobinopathy, as provided in any one of Methods 80 or 81, wherein the one or more NLSs is a SV40 NLS.

In another method, Method 83, the present disclosure provides a method for treating a patient with a hemoglobinopathy, as provided in Method 79, wherein the weight ratio of sgRNA to Cas9 endonuclease in the RNP is 1:1.

In another method, Method 84, the present disclosure provides a method for treating a patient with a hemoglobinopathy, as provided in Method 79, wherein the one sgRNA comprises the nucleic acid sequence of SEQ ID NO: 11, the Cas9 endonuclease is a S. pyogenes Cas9 comprising a N-terminus SV40 NLS and a C-terminus SV40 NLS, wherein the weight ratio of sgRNA to Cas9 endonuclease is 1:1.

In another method, Method 85, the present disclosure provides a method for treating a patient with a hemoglobinopathy, as provided in Method 79, wherein the one sgRNA comprises the nucleic acid sequence of SEQ ID NO: 12, the Cas9 endonuclease is a S. pyogenes Cas9 comprising a N-terminus SV40 NLS and a C-terminus SV40 NLS, wherein the weight ratio of sgRNA to Cas9 endonuclease is 1:1.

In another method, Method 86, the present disclosure provides a method for treating a patient with a hemoglobinopathy, as provided in any one of Methods 1, 8, 16, 26, 31, 55, 56, and 71, wherein the one or more SSB, DSB, or locus is located within a second intron of the BCL11A gene.

In another method, Method 87, the present disclosure provides a method for treating a patient with a hemoglobinopathy, as provided in any one of Methods 1, 8, 16, 26, 31, 55, 56, and 71, wherein the one or more SSB, DSB, or locus is located within a +55 DHS of the BCL11A gene.

In another method, Method 88, the present disclosure provides a method for treating a patient with a hemoglobinopathy, as provided in any one of Methods 1, 8, 16, 26, 31, 55, 56, and 71, wherein the one or more SSB, DSB, or locus is located within a +58 DHS of the BCL11A gene.

In another method, Method 89, the present disclosure provides a method for treating a patient with a hemoglobinopathy, as provided in any one of Methods 1, 8, 16, 26, 31, 55, 56, and 71, wherein the one or more SSB, DSB, or locus is located within a +62 DHS of the BCL11A gene.

In another method, Method 90, the present disclosure provides a method for treating a patient with a hemoglobinopathy, as provided in any one of Methods 43-70, wherein the gRNA comprises a spacer sequence that is complementary to one or more of: a +55 DHS of the BCL11A gene, a +58 DHS of the BCL11A gene, and a +62 DHS of the BCL11A gene.

In another method, Method 91, the present disclosure provides a method for treating a patient with a hemoglobinopathy, as provided in any one of Methods 71-85, wherein the two gRNAs comprise a spacer sequence that is complementary to one or more of: a +55 DHS of the BCL11A gene, a +58 DHS of the BCL11A gene, and a +62 DHS of the BCL11A gene.

In another method, Method 92, the present disclosure provides a method for treating a patient with a hemoglobinopathy, as provided in any one of Methods 1, 8, 16, 26, 31, and 71, wherein the deletion comprises a +55 DHS of the BCL11A gene, or a fragment thereof.

In another method, Method 93, the present disclosure provides a method for treating a patient with a hemoglobinopathy, as provided in any one of Methods 1, 8, 16, 26, 31, and 71, wherein the deletion comprises a +58 DHS of the BCL11A gene, or a fragment thereof.

In another method, Method 94, the present disclosure provides a method for treating a patient with a hemoglobinopathy, as provided in any one of Methods 1, 8, 16, 26, 31, and 71, wherein the deletion comprises a +62 DHS of the BCL11A gene, or a fragment thereof.

In another method, Method 95, the present disclosure provides a method for treating a patient with a hemoglobinopathy, as provided in any one of Methods 1, 8, 16, 26, 31, and 71, wherein the deletion comprises a +55 DHS of the BCL11A gene and a +58 DHS of the BCL11A gene, or fragments thereof.

In another method, Method 96, the present disclosure provides a method for treating a patient with a hemoglobinopathy, as provided in any one of Methods 1, 8, 16, 26, 31, and 71, wherein the deletion comprises a +55 DHS of the BCL11A gene and a +62 DHS of the BCL11A gene, or fragments thereof.

In another method, Method 97, the present disclosure provides a method for treating a patient with a hemoglobinopathy, as provided in any one of Methods 1, 8, 16, 26, 31, and 71, wherein the deletion comprises a +58 DHS of the BCL11A gene and a +62 DHS of the BCL11A gene, or fragments thereof.

In another method, Method 98, the present disclosure provides a method for treating a patient with a hemoglobinopathy, as provided in any one of Methods 1, 8, 16, 26, 31, and 71, wherein the deletion comprises a +55 DHS of the BCL11A gene, a +58 DHS of the BCL11A gene, and a +62 DHS of the BCL11A gene, or fragments thereof.

In another method, Method 99, the present disclosure provides a method for treating a patient with a hemoglobinopathy, as provided in any one of Methods 1, 8, 16, 26, 31, and 71, wherein the deletion is 10 kb or less.

In another method, Method 100, the present disclosure provides a method for treating a patient with a hemoglobinopathy, as provided in any one of Methods 1, 8, 16, 26, 31, and 71, wherein the deletion is 3.1 kb.

In another method, Method 101, the present disclosure provides a method for treating a patient with a hemoglobinopathy, as provided in any one of Methods 1, 8, 16, 26, or 31-100, wherein the Cas9 or Cpf1 mRNA, and gRNA are either each formulated into separate lipid nanoparticles or all co-formulated into a lipid nanoparticle.

In another method, Method 102, the present disclosure provides a method for treating a patient with a hemoglobinopathy, as provided in any one of Methods 1, 8, 16, 26, or 31-100, wherein the Cas9 or Cpf1 mRNA is formulated into a lipid nanoparticle, and the gRNA is delivered to the cell by an adeno-associated virus (AAV) vector.

In another method, Method 103, the present disclosure provides a method for treating a patient with a hemoglobinopathy, as provided in any one of Methods 1, 8, 16, 26, or 31-100, wherein the Cas9 or Cpf1 mRNA is formulated into a lipid nanoparticle, and the gRNA is delivered to the cell by electroporation.

In another method, Method 104, the present disclosure provides a method for treating a patient with a hemoglobinopathy, as provided in any one of Methods 1, 8, 16, 26, or 31-100, wherein the one or more RNP is delivered to the cell by electroporation.

In another method, Method 105, the present disclosure provides a method for treating a patient with a hemoglobinopathy, as provided in any one of Methods 1-104, wherein the BCL11A gene is located on Chromosome 2: 60, 451, 167-60,553,567 (Genome Reference Consortium—GRCh38).

In another method, Method 106, the present disclosure provides a method for treating a patient with a hemoglobinopathy, as provided in any one of Methods 1-105, wherein the hemoglobinopathy is selected from a group consisting of sickle cell anemia and thalassemia (α, β, δ, γ, and combinations thereof).

In another method, Method 107, the present disclosure provides a method for treating a patient with a hemoglobinopathy, as provided in any one of Methods 1-106, wherein the editing the BCL11A gene reduces BCL11A gene expression.

In another method, Method 108, the present disclosure provides a method for treating a patient with a hemoglobinopathy wherein the patient is administered a population of genetically engineered cells, which comprise a genetic mutation, which is one of a permanent insertion, deletion, modulation, and an inactivation of a transcriptional control sequence of a BCL11A gene, wherein the genetic mutation occurs at one or more sites targeted by a sgRNA comprising the nucleic acid sequence of SEQ ID NO: 11.

In another method, Method 109, the present disclosure provides a method for treating a patient with a hemoglobinopathy wherein the patient is administered a population of genetically engineered cells, which comprise a genetic mutation, which is one of a permanent insertion, deletion, modulation, and an inactivation of a transcriptional control sequence of a BCL11A gene, wherein the genetic mutation occurs at one or more sites targeted by a sgRNA comprising the nucleic acid sequence of SEQ ID NO: 12.

In another method, Method 110, the present disclosure provides a method for treating a patient with a hemoglobinopathy wherein the patient is administered a population of genetically engineered cells, which comprise a genetic mutation, which is one of a permanent insertion, deletion, modulation, and an inactivation of a transcriptional control sequence of a BCL11A gene, wherein the genetic mutation occurs at one or more sites targeted by a first sgRNA comprising the nucleic acid sequence of SEQ ID NO: 11 and a second sgRNA comprising the nucleic acid sequence of SEQ ID NO: 12.

In another method, Method 111, the present disclosure provides a method for treating a patient with a hemoglobinopathy wherein the patient is administered a population of genetically engineered cells, which comprise a genetic mutation, which is one of a permanent insertion, deletion, modulation, and an inactivation of a transcriptional control sequence of a BCL11A gene, wherein the genetic mutation occurs at one or more sites targeted by a first sgRNA comprising the nucleic acid sequence of SEQ ID NO: 11 and a second sgRNA comprising the nucleic acid sequence of SEQ ID NO: 13.

In another method, Method 112, the present disclosure provides a method for treating a patient with a hemoglobinopathy wherein the patient is administered a population of genetically engineered cells, which comprise a genetic mutation, which is one of a permanent insertion, deletion, modulation, and an inactivation of a transcriptional control sequence of a BCL11A gene, wherein the genetic mutation occurs at one or more sites targeted by a first sgRNA comprising the nucleic acid sequence of SEQ ID NO: 12 and a second sgRNA comprising the nucleic acid sequence of SEQ ID NO: 13.

In another method, Method 113, the present disclosure provides a method as provided in Method 107, wherein the one or more sgRNAs is a first and a second sgRNA, wherein
(a) the first sgRNA comprises the nucleic acid sequence of SEQ ID NO: 11 and the second sgRNA comprises the nucleic acid sequence of SEQ ID NO: 12;
(b) the first sgRNA comprises the nucleic acid sequence of SEQ ID NO: 11 and the second sgRNA comprises the nucleic acid sequence of SEQ ID NO: 13; or
(c) the first sgRNA comprises the nucleic acid sequence of SEQ ID NO: 12 and the second sgRNA comprises the nucleic acid sequence of SEQ ID NO: 13.

In another method, Method 113, the present disclosure provides an exemplary ex vivo method for treating a patient with a hemoglobinopathy. To perform this method, a population of suitable cells (e.g., CD34+ cells such as HSCs) may be obtained from a patient having a hemoglobinopathy (e.g., those disclosed herein such as sickle cell anemia or thalassemia, e.g., α, β, δ, γ, and combinations thereof) via a conventional procedure and/or a procedure described herein. Prior to isolation of the population of cells, the patient may be treated with granulocyte colony stimulating factor (GCSF), optionally in combination with.1,1'-(1,4-phenylenebismethylene)bis(1,4,8,11-tetraazacyclotetradecane). The population of cells can then be genetically edited by a suitable gene editing method to introduce one or more mutations into the BCL11a gene locus so as to inhibit BCL11A gene expression and enhance expression of g-globin and HbF in the edited cells. For example, one or more suitable DNA endonucleases (e.g., Cas9 endonucleases) and one or more suitable sgRNAs can be introduced into the population of cells to induce SSB and/or DSB in the BCL11A gene locus, thereby genetically editing the target BCL11A gene. In some instances, the Cas9 endonuclease comprises a *S. pyogenes* Cas9 and optionally a N-terminus SV40 NLS and/or a C-terminus SV40 NLS. The one or more sgRNAs may comprises at least one sgRNA that comprises the nucleic acid sequence of SEQ ID NO: 11 or 12. In some instances, the one or more sgRNA may comprise a nucleic acid sequence of SEQ ID NO:11 and a second nucleic acid sequence of SEQ ID NO:12. In other instances, the one or more sgRNA may comprise a first nucleic acid sequence of SEQ ID NO:11 and a second nucleic acid sequence of SEQ ID NO:13. Any of the sgRNAs of SEQ ID Nos:11-13 may comprise modified nucleotides, for example, comprising three 2'-O-methyl-phosphorothioate residues at or near each of its 5' and 3' ends. The Cas9 endonuclease and the one or more sgRNAs may form one or more RNPs, which can be delivered into the cells via electroporation. When multiple sgRNAs are used, the sgRNAs may complexed with the Cas9 endonuclease in one RNP and delivered into the cells concurrently via, e.g., electroporation. Alternatively, the multiple sgRNAs may form multiple RNPs with the Cas9 endonuclease and be delivered into the cells sequentially, for example, via successive electroporation as disclosed herein. The genetically edited cells thus obtained may then be administered to the patient in need of the treatment via a suitable route, e.g., infusion. Any features of Methods 108-113 disclosed herein can also be used in this embodiment.

The present disclosure also provides a composition, Composition 1, comprising one or more gRNAs for editing a BCL11A gene in a cell from a patient with a hemoglobinopathy, the one or more gRNAs comprising a spacer sequence selected from the group consisting of nucleic acid sequences in any one of SEQ ID NOs: 6-7 of the Sequence Listing.

In another composition, Composition 2, the present disclosure provides the one or more gRNAs of Composition 1, wherein the one or more gRNAs are one or more single-molecule guide RNAs (sgRNAs).

In another composition, Composition 3, the present disclosure provides the one or more gRNAs of any one of Compositions 1 or 2, wherein the one or more gRNAs or one or more sgRNAs is one or more modified gRNAs or one or more modified sgRNAs.

In another composition, Composition 4, the present disclosure provides the one or more modified sgRNAs of Composition 3, wherein the one or more modified sgRNAs comprises three 2'-O-methyl-phosphorothioate residues at or near each of its 5' and 3' ends.

In another composition, Composition 5, the present disclosure provides the one or more modified sgRNAs of Composition 4, wherein the one or more modified sgRNAs comprises the nucleic acid sequence of SEQ ID NO: 11.

In another composition, Composition 6, the present disclosure provides the one or more modified sgRNAs of Composition 4, wherein the one or more modified sgRNAs comprises the nucleic acid sequence of SEQ ID NO: 12.

In another composition, Composition 7, the present disclosure provides the one or more gRNAs or sgRNAs of any one of Compositions 1 or 2, wherein the one or more gRNAs or sgRNAs target a GATA1 site.

In another composition, Composition 8, the present disclosure provides the one or more gRNAs or sgRNAs of any one of Compositions 1 or 2, wherein the one or more gRNAs or sgRNAs target an ELF1 site.

In another composition, Composition 9, the present disclosure provides a sgRNA comprising the nucleic acid sequence of SEQ ID NO: 11.

In another composition, Composition 10, the present disclosure provides a sgRNA comprising the nucleic acid sequence of SEQ ID NO: 12.

In a first therapeutic, Therapeutic 1, the present disclosure provides a therapeutic comprising at least one or more gRNAs for editing a BCL11A gene in a cell from a patient with a hemoglobinopathy, the one or more gRNAs comprising a spacer sequence selected from the group consisting of nucleic acid sequences in any one of SEQ ID NOs: 6-7 of the sequence listing.

In another therapeutic, Therapeutic 2, the present disclosure provides the therapeutic of Therapeutic 1, wherein the one or more gRNAs are one or more sgRNAs.

In another therapeutic, Therapeutic 3, the present disclosure provides the therapeutic of Therapeutics 1 or 2, wherein the one or more gRNAs or one or more sgRNAs is one or more modified gRNAs or one or more modified sgRNAs.

In another therapeutic, Therapeutic 4, the present disclosure provides the therapeutic of Therapeutics 1-3, wherein the one or more gRNAs comprises a nucleic acid sequence selected from the group consisting of SEQ ID NOs: 11-12 in the Sequence Listing.

In another therapeutic, Therapeutic 5, the present disclosure provides a therapeutic for treating a patient with a hemoglobinopathy formed by the method comprising: introducing one or more DNA endonucleases; introducing one or more gRNA or one or more sgRNA for editing a BCL11A gene; wherein the one or more gRNAs or sgRNAs comprise a spacer sequence selected from the group consisting of nucleic acid sequences in SEQ ID NOs: 6-7 of the Sequence Listing.

In another therapeutic, Therapeutic 6, the present disclosure provides the therapeutic of Therapeutic 5, wherein the one or more gRNAs or sgRNAs comprises a nucleic acid sequence selected from the group consisting of SEQ ID NOs: 11-12 in the sequence listing.

Definitions

The term "comprising" or "comprises" is used in reference to compositions, methods, therapeutics and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, therapeutics and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

EXAMPLES

The present disclosure will be more fully understood by reference to the following examples, which provide illustrative non-limiting aspects of the invention.

The examples describe the use of the CRISPR system as an illustrative genome editing technique to create defined genomic deletions or insertions, termed "genomic modifications" herein, within or near the BCL11A gene or other DNA sequence that encodes a regulatory element of the BCL11A gene that lead to a permanent insertion, deletion, modulation, or inactivation of a transcriptional control sequence of the BCL11A gene. Introduction of the defined therapeutic modifications represents a novel therapeutic strategy for the potential amelioration of a hemoglobinopathy, as described and illustrated herein.

Example 1—CRISPR/S. Pyogenes (Sp)Cas9 Target Sites for the Transcriptional Control Sequence of the BCL11A Gene Regions of the 12.4 kb transcriptional control sequence of the BCL11A gene were scanned for target sites. Each area was scanned for a protospacer adjacent motif (PAM) having the sequence NRG. gRNA 20 bp spacer sequences corresponding to the PAM were identified, as shown in SEQ ID NOs: 6-7 of the Sequence Listing.

Example 2—Bioinformatics Analysis of the Guide Strands

Candidate guides were screened and selected in a single process or multi-step process that involves both theoretical binding and experimentally assessed activity at both on-target and off-target sites. By way of illustration, candidate guides having sequences that match a particular on-target site, such as a site within the transcriptional control sequence of the BCL11A gene, with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended. Candidates predicted to have relatively lower potential for off-target activity can then be assessed experimentally to measure their on-target activity, and then off-target activities at various sites. Guides having sufficiently high on-target activity to achieve desired levels of gene editing at the selected locus, and relatively lower off-target activity to reduce the likelihood of alterations at other chromosomal loci are preferred. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the CRISPR/Cas9/Cpf1 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.bme.gatech.edu) compiles such similarities. Other bioinformatics tools include, but are not limited to autoCOSMID and CCtop.

Bioinformatics are used to minimize off-target cleavage in order to reduce the detrimental effects of mutations and chromosomal rearrangements. Studies on CRISPR/Cas9 systems suggested the possibility of off-target activity due to non-specific hybridization of the guide strand to DNA sequences with base pair mismatches and/or bulges, particularly at positions distal from the PAM region. Therefore, it is important to have a bioinformatics tool that can identify potential off-target sites that have insertions and/or deletions between the RNA guide strand and genomic sequences, in addition to base-pair mismatches. Bioinformatics tools based upon the off-target prediction algorithm CCTop were used to search genomes for potential CRISPR off-target sites (CCTop is available on the web at crispr.cos.uni-heidelberg.de/). The output ranked lists of the potential off-target sites based on the number and location of mismatches, allowing more informed choice of target sites, and avoiding the use of sites with more likely off-target cleavage.

An additional factor includes avoiding common single nucleotide polymorphisms (SNP) regions when designing gRNAs.

Example 3—Testing of Guides in Cells for On-Target Activity

The gRNAs predicted to have the lowest off-target activity were then tested for on-target activity in CD34+ cells, and evaluated for InDel frequency using TIDE or next generation sequencing. TIDE is a web tool to rapidly assess genome editing by CRISPR-Cas9 of a target locus determined by a guide RNA (gRNA or sgRNA). Based on quantitative sequence trace data from two standard capillary sequencing reactions, the TIDE software quantifies the editing efficacy and identifies the predominant types of insertions and deletions (InDels) in the DNA of a targeted cell pool. See Brinkman et al, Nucl. Acids Res. (2014) for a detailed explanation and examples. Next-generation sequencing (NGS), also known as high-throughput sequencing, is the catch-all term used to describe a number of different modem sequencing technologies including: Illumina (Solexa) sequencing, Roche 454 sequencing, Ion torrent: Proton/PGM sequencing, and SOLiD sequencing. These recent technologies allow one to sequence DNA and RNA much more quickly and cheaply than the previously used Sanger sequencing, and as such have revolutionized the study of genomics and molecular biology.

Example 4—Testing of Guides in Cells for Off-Target Activity

The gRNAs having the best on-target activity from the TIDE and next generation sequencing studies in the above example were then tested for off-target activity using whole genome sequencing. Candidate gRNAs were more completely evaluated in CD34+ cells or iPSCs.

Example 5—Testing of Preferred gRNA Combinations in Cells

The gRNAs having the best on-target activity from the TIDE and next generation sequencing studies and lowest off-target activity were tested in combinations to evaluate the size of the deletion resulting from the use of each gRNA combination. Potential gRNA combinations were evaluated in primary human CD34+ cells.

For example, gRNA combinations were tested for efficiency of deleting all or a portion of the transcriptional control sequence of the BCL11A gene. The gRNA combinations were also tested for efficiency of deleting all or a portion of the +55 DNA hypersensitive site (DHS) of the BCL11A gene, the +58 DNA hypersensitive site (DHS) of the BCL11A gene, the +62 DNA hypersensitive site (DHS) of the BCL11A gene, or combinations thereof.

Example 6—In Vitro Transcribed (IVT) gRNA Screen

To identify a large spectrum of pairs of gRNAs able to edit the cognate DNA target region, an in vitro transcribed (IVT) gRNA screen was conducted. Regions of the 12.4 kb transcriptional control sequence of the BCL11A gene was submitted for analysis using a gRNA design software and scanned for target sites. The resulting list of gRNAs was narrowed to a list of hundreds of gRNAs based on uniqueness of sequence (only gRNAs without a perfect match somewhere else in the genome were screened) and minimal predicted off targets. This set of gRNAs was in vitro transcribed, and transfected using messenger Max into HEK293T cells that stably express Cas9. Cells were harvested 48 hours post transfection, the genomic DNA was isolated, and editing efficiency was evaluated using TIDE analysis. Candidate guides were further evaluated based on γ:α mRNA ratios of erythroid cells differentiated from edited CD34+ cells. For example, cells edited with candidate guides that resulted in γ:α mRNA ratios greater than or equal to the γ:α mRNA ratio of cells edited with SPY101 were further evaluated. The following Table (Table 4) provides information related to gRNAs, including candidate gRNAs (CG-001, CG-002, and SPY101).

TABLE 4

| Name | Sequence | SEQ ID NO. |
|---|---|---|
| CG-001 | 5'usgscsUUGGUCGGCACUGAUAGGUUUUAGAGCUAG AAAUAGCAAGUUAAAAUAAGGCUAGUCCGUUAUCA ACUUGAAAAAGUGGCACCGAGUCGGUGCusususU3' | 11 |
| CG-002 | 5'asuscsAGAGGCCAAACCCUUCCGUUUUAGAGCUAGA AAUAGCAAGUUAAAAUAAGGCUAGUCCGUUAUCAA CUUGAAAAAGUGGCACCGAGUCGGUGCusususU3' | 12 |
| SPY101 | 5'csusasACAGUUGCUUUUAUCACGUUUUAGAGCUAGA AAUAGCAAGUUAAAAUAAGGCUAGUCCGUUAUCAA CUUGAAAAAGUGGCACCGAGUCGGUGCusususU3' | 13 |
| 1619 | 5'usususUAUCACAGGCUCCAGGAGUUUUAGAGCUAG AAAUAGCAAGUUAAAAUAAGGCUAGUCCGUUAUCA ACUUGAAAAAGUGGCACCGAGUCGGUGCusususU3' | 15 |
| 1621 | 5'csascsAGGCUCCAGGAAGGGUUGUUUUAGAGCUAGA AAUAGCAAGUUAAAAUAAGGCUAGUCCGUUAUCAA CUUGAAAAAGUGGCACCGAGUCGGUGCusususU3' | 16 |

N RNA residues
n 2'-O-methyl residues
s phosphorothioate

Example 7—Editing Cells with Various gRNAs

Mobilized human peripheral blood (mPB) CD34+ cells from four independent human donors were cultured in serum free CellGro® media including 100 ng/ml recombinant human stem cell factor (SCF), 100 ng/ml recombinant human Flt 3-Ligand (FLT3L), and 100 ng/ml Thrombopoietin (TPO). 100,000 cells per donor were electroporated using Lonza Amaxa 4D electroporator without any CRISPR/Cas9 editing components (mock electroporation sample), with EGFP sgRNA and Cas9 protein as a negative control (EGFP), with SPY101 sgRNA and Cas9 protein (SPY), with SD2 sgRNA and Cas9 protein (SD2), with CG-001 sgRNA and Cas9 protein (CG-001), with CG-002 sgRNA and Cas9 protein (CG-002), with CG-001+CG-002 sgRNAs and Cas9 protein (CG-001+CG-002), with Hereditary Persistence of Fetal Hemoglobin 5-1 (HPFH5-1)+HPFH5-D sgRNAs and Cas9 protein (HPFH5 1D), with HPFH5-5+HPFH5-D sgRNAs and Cas9 protein (HPFH5 5D), with Kenya K5/17 sgRNAs and Cas9 protein (Kenya K5/17) or with dual BCL11A Exon 2 sgRNAs and Cas9 protein (Exon2). The recombinant Cas9 protein encodes for S. pyogenes Cas9 flanked by two SV40 nuclear localization sequences (NLSs). These experiments were performed using a ribonucleoprotein (RNP) 1:1 weight ratio of sgRNA to Cas9. The Exon 2 sgRNAs create a 196 bp deletion on Exon 2 of the BCL11A locus and served as a positive control.

Figure 3:
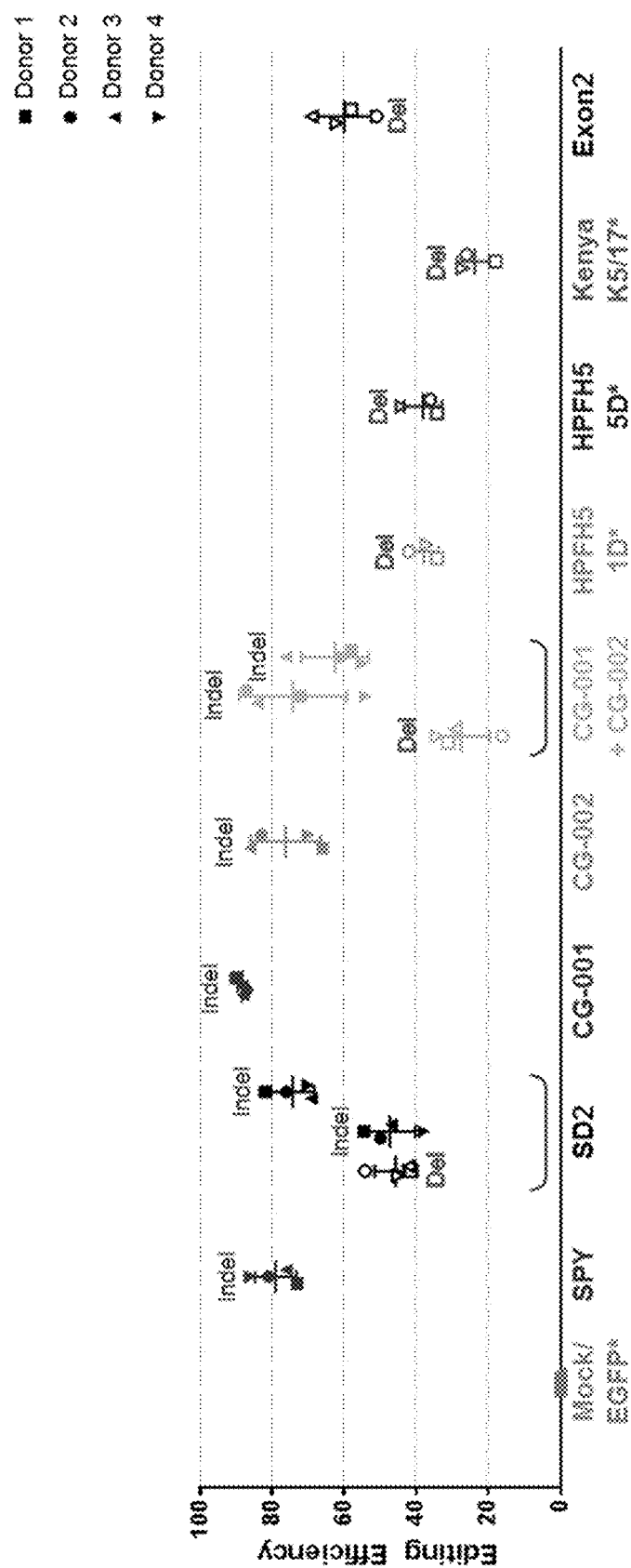
FIG. 3 shows editing efficiency for human mobilized peripheral blood (mPB) CD34+ hematopoietic stem and progenitor cells (HSPCs) isolated from Donors 1-4 and edited with different gRNAs and Cas9 protein.

The editing efficiency was determined two days after electroporation for each of the cells electroporated with SPY101 sgRNA and Cas9 protein (SPY), cells electroporated with SD2 sgRNA and Cas9 protein, cells electroporated with CG-001 sgRNA and Cas9 protein, cells electroporated with CG-002 sgRNA and Cas9 protein, cells electroporated with CG-001+CG-002 sgRNAs and Cas9 protein, cells electroporated with HPFH5-1+HPFH5-D sgRNAs and Cas9 protein, cells electroporated with HPFH5-5+HPFH5-D sgRNAs and Cas9 protein, cells electroporated with Kenya K5/17 sgRNAs and Cas9 protein, or cells electroporated with Exon 2 sgRNAs and Cas9 protein (FIGS. 3 and 6), as described in the "On- and off-target mutation detection by sequence" and "Mutation detection assays" sections described herein. In addition, cells electroporated with two sgRNAs and Cas9 protein were assessed for deletion frequency by droplet digital PCR (ddPCR). Each CD34+ cell donor is represented by a unique symbol (■, ●, ▲, ▼).

Cells were allowed to recover for two days after electroporation before being switched to a three phase erythroid differentiation medium: on days 0-6, cells are cultured in Phase I media, composed of 20 ng/ml SCF, 31U/ml EPO, 5% human serum, 10 g/ml insulin, 330 g/ml of human holo transferrin, 21U/ml of heparin, 5 ng/ml of IL-3, 1% L-glutamine in IMDM basal media; on days 7-9, cells are cultured in Phase II media, composed of Phase I media minus IL-3; and on days 10-21, cells are cultured in Phase III media, composed of Phase II media minus SCF.

Figures 4A, 4B:
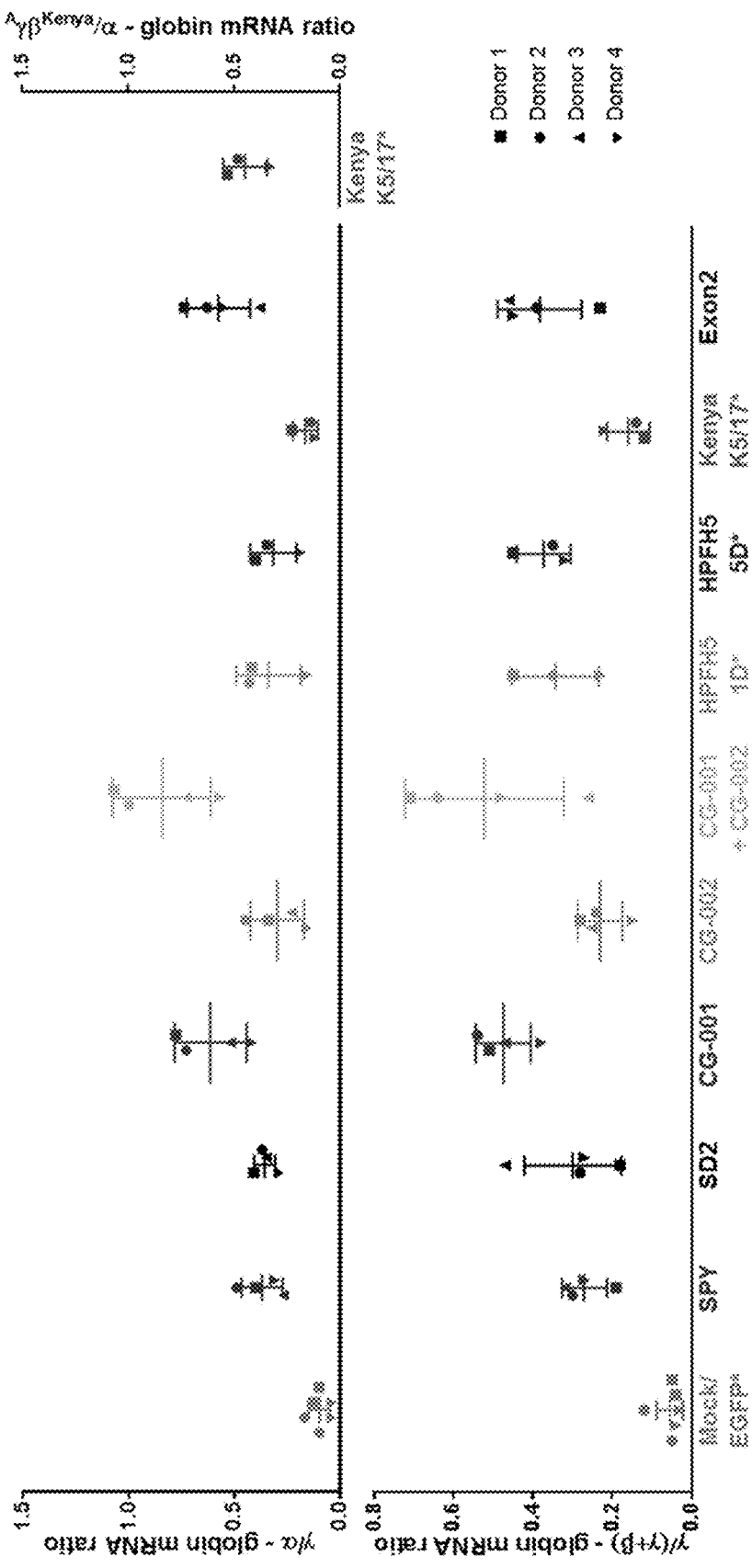
FIGS. 4A-4B show ratios of $\gamma$-globin mRNA ($\gamma/\alpha$ or $\gamma/(\gamma+\beta)$) measured in erythrocytes differentiated in vitro from human mPB CD34+HSPCs isolated from Donors 1-4 and edited with different gRNAs and Cas9 protein.

The gene-edited mPB CD34+ cells that were differentiated into erythrocytes were further tested via quantitative reverse transcription-PCR analysis (qRT-PCR), FACS, and ion-exchange HPLC (IEX-HPLC). For example, after differentiating these cells for 12 days in erythroid differentiation medium, globin mRNA expression (ratio of γ/α (FIG. 4A) or ratio of γ/(γ+β) (FIG. 4B)) was determined by qRT-PCR.

The γ-globin measurements (normalized against α-globin or total β-like globins (γ+β)) in all BCL11A target edited cells (SPY, CG-001 and/or CG-002, or Exon2) were higher than the control edited cells (Mock or EGFP) (FIGS. 4A-4B), indicating that disruption to the BCL11A gene can result in upregulation of γ-globin transcript expression. This is in line with the hypothesis that BCL11A is a transcriptional repressor of γ-globin.

HbF tetrameric protein expression was measured for each of the electroporated mPBs CD34+ cells described herein that differentiated into erythrocytes on Day 14 (FIG. 5A) and Day 18 (FIG. 5B) using IEX-HPLC. mPBs CD34+ cells were electroporated with SPY101 sgRNA and Cas9 protein, SD2 sgRNA and Cas9 protein, CG-001 sgRNA and Cas9 protein, CG-002 sgRNA and Cas9 protein, CG-001+CG-002 sgRNAs and Cas9 protein, HPFH5-1+HPFH5-D sgRNAs and Cas9 protein, HPFH5-5+HPFH5-D sgRNAs and Cas9 protein, Kenya K5/17 sgRNAs and Cas9 protein, or Exon 2 sgRNAs and Cas9 protein.

The HbF measurements (normalized against total hemoglobin (HbF+HbA) in all BCL11A target edited cells (SPY, CG-001 and/or CG-002, or Exon2) were higher than the control edited cells (Mock or EGFP) (FIGS. 5A-5B), indicating that disruption to the BCL11A gene can result in upregulation of HbF protein expression. This is in line with the observed increase in γ-globin mRNA expression from FIGS. 4A-4B.

Figure 11:
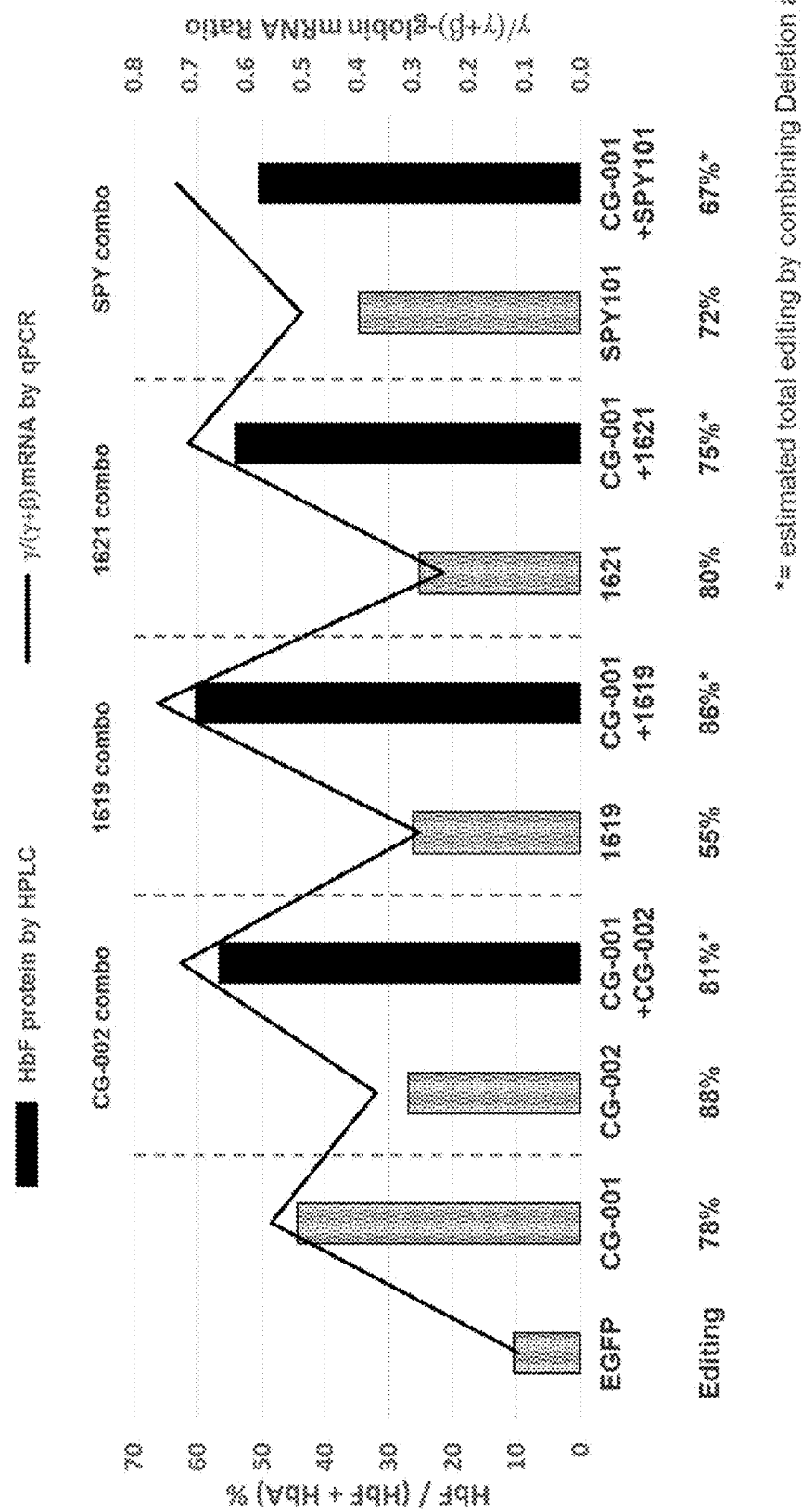
FIG. 11 shows the ratios of γ-globin to β-like globin mRNA (γ/(γ+β), solid line) or percentage of HbF in total hemoglobins (HbF/(HbF+HbA), bars) measured in erythrocytes differentiated in vitro from human mPB CD34+HSPCs edited with Cas9 and EGFP (non-editing control), CG-001, CG-002, 1619, 1621 or SPY101 gRNA, and combinations of CG-001 with these individual guides. CG-002, 1619, 1621 and SPY101 gRNAs all target within the +58 DHS of the BCL11A gene whereas CG-001 gRNA target within the +55 DHS of BCL11A. Editing efficiency for single gRNA edited conditions represent % of Indels detected whereas editing efficiency for double gRNA edited combo conditions represent the minimal amount of total editing (by adding Indels at either gRNA targeted site and deletion generated from cutting by both gRNAs, exemplified by FIGS. 2A and 2C-2E. In each instance, combination with CG-001 increased γ-globin mRNA or HbF production.

To illustrate that combination of different guides from +58 DHS with CG-001 can increase the overall in vitro efficacy of γ-globin transcript expression and HbF tetrameric protein, single sgRNA and dual sgRNA (CG-001 combined with either four of the +58 DHS sgRNAs) were complexed with Cas9 protein prior electroporating the resultant RNP into CD34+HSPCs similar to described above. All conditions resulted in high editing efficiency and after in vitro erythroid differentiation, all four combinations of dual sgRNAs increased both γ-globin mRNA and HbF protein levels above their respective single sgRNA conditions (FIG. 11).

Example 8—Testing of Guide RNAs in Cells for Off-Targeting Activity

While on-target editing of the genome is fundamental to a successful therapy, the detection of any off-target editing events is an important component of ensuring product safety. One method for detecting modifications at off-target sites involves enriching for regions of the genome that are most similar to the on-target site via hybrid capture sequencing and quantifying any indels that are detected.

Hybrid capture sequencing is a method that quantifies off-target edits in CRISPR-Cas9 edited cells and DNA. Details related to the hybrid capture sequencing method are as follows:
Materials and Methods
Materials and Sources
1.1.1. Genomic DNA
As the purpose of this method is to determine if editing by CRISPR-Cas9 has occurred at off-target sites in the genome at least two input samples are typically used—treated and control (untreated, EGFP sgRNA and Cas9 protein electroporated, etc.) samples. Each sample has genomic DNA (gDNA) extracted by an appropriated method and that gDNA is hybridized with the hybrid capture libraries (1.1.2) followed by the remainder of the protocol as described below.
1.1.2. Hybrid Capture Libraries
Hybrid capture libraries as described in (1.2.2) are generated by providing a list of up to 57,000 120-mer oligonucleotide bait sequences which are then synthesized as a custom SureSelect XT hybrid capture kit.

1.2 Methods
1.2.1. Off-Target Site Detection Algorithms
To determine the sites that are most likely to have off-target editing we use several algorithms with different features to ensure a wide-range of off-target sites were covered.
1.1.1.1. CCTop and CCTop-Indel
For a given guide sequence CCTop uses the Bowtie 1 sequence mapping algorithm to search the genome for off-target sites with up to 5 mismatch between the site and the guide. We refer to these site as "homologous off-target sites" (rather than "predicted off-target sites") since only sequence homology is used to determine the potential off-target sites in the genome. These 5 mismatches are limited to no more than 2 mismatches in the 5 base alignment seed region closest to the PAM end of the sequences. The CRISPOR algorithm (1.2.1.2) does not have the limitation in the seed region and thus complements CCTop. For a given guide sequence, CCTop-Indel uses the BWA sequence mapping algorithm to search the genome for potential off-target sites in a way that identifies sites with mismatches to the guide sequence, as well as sites with DNA/RNA bulges resulting in sequence alignment gaps. This algorithm can generate potential off-target sites within 5 mismatches and 0 gaps, as well as up to 3 mismatches and 1 gap from the guide sequence. The CCTop-Indel algorithm can be used in place of or in addition to a combination of CCTop and COSMID, as it generates comprehensive mismatch as well as gapped homology sites.
1.2.1.1. COSMID
Since some off-target Cas9 cleavage sites may have a short indels (also referred to as bulges) between themselves and the guide, we also search with the COSMID algorithm that can detect off-target sites with indels (typically limited to up to 2 indels) and thus complements the search done with CCTop.
1.2.1.2. CRISPOR
CRISPOR is a tool that implements many different published CRISPR on- and off-target scoring functions for the purpose of comparing various methods. It uses the BWA algorithm for searching guide sequences against the genome to find their off-target sites. This differs from Bowtie 1 algorithm used in CCTop and allows for a search that is slightly more permissive in that mismatches near the PAM region are not limited to 2 out of 5 bases as in CCTop.
1.2.1.3. PAMs
By default, screens are done with a search for guides with an NGG or NAG PAMs as they have some of the greatest activity. Later stage screens may include more PAMs to ensure that no off-target sites, even those with very low activity, are missed.
1.2.1.4. Combination of Algorithms
The guides output by each algorithm are joined together to eliminate identical off-target sites and fed into the hybrid capture bait design component.
1.2.2. Hybrid Capture Baits and GUIDE-Seq
1.2.2.0 GUIDE-Seq
Genome-wide Unbiased Identification of DSBs by sequencing (GUIDE-seq) is an approach in which a double-stranded oligodeoxynucleotide (dsODN), 34 nucleotides in length, is co-administered with sgRNAs and Cas9 nuclease into cells (see, e.g., Tsai et al., 2015). During the process of CRISPR-Cas9 gene editing, DNA is cleaved by the Cas9 enzyme, causing a double-strand break (DSB) in the DNA. The short GUIDE-seq dsODN may then be incorporated into the site of the DSB. The GUIDE-seq dsODN contains a region that is distinct from all known endogenous sequences of the human genome, and that can be amplified with a PCR primer. This permits specific amplification of sites of dsODN incorporation from human genomic DNA by PCR. With subsequent sequencing of these PCR products and computational analysis, amplified sites of dsODN integration can be identified, and considered as potential off-target editing sites.

1.2.2.1 Design

Figure 9:
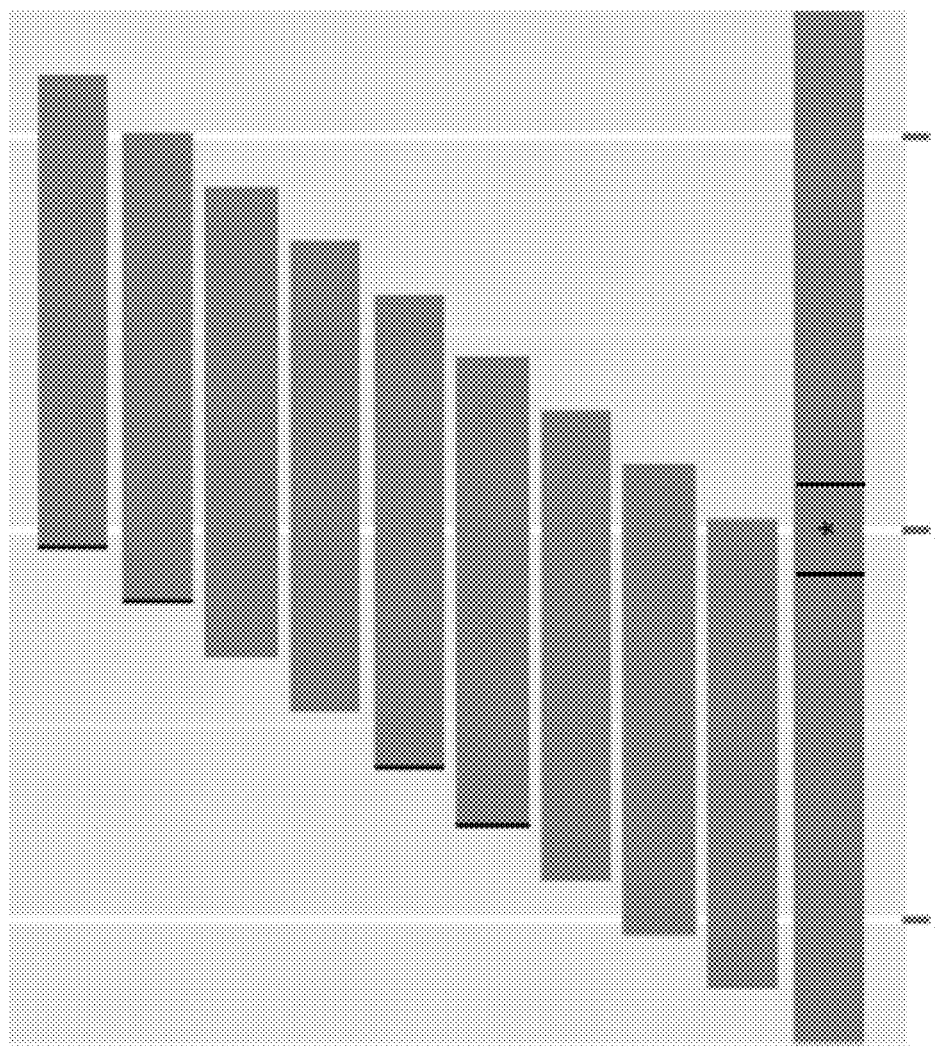
FIG. 9 depicts the hybrid capture bait design.

The list of sites produced by the off-target site detection algorithms (1.2.1.), as well as any generated GUIDE-seq sites (1.2.2.0), are then used to generate hybrid capture probes that will enrich for each of the off-target sites in the input gDNA samples. Although one bait may be sufficient to successfully enrich for a target DNA sequence, several baits are generally designed and tiled across the target site (FIG. 9) in order to make it more likely that a bait specifically pulls down a target region even if it is flanked on a side by repetitive sequence that may be difficult to bind specifically. Hybrid capture baits (120-mers, dark colored portions) tiled across a bait (20-mer, light portion denoted by the *) (FIG. 9).

1.2.3. Sequencing

After hybrid capture enrichment, sequencing is done on an Illumina HiSeq sequencer with paired-end 125 bp reads and a 175 bp insert size. Sequencing is typically done to target a depth of coverage that targets having 5 reads detected from a minimal frequency event. To detect for example 0.5% indel events, sequencing to 1000× coverage is performed so that an 0.5% event might have 5 reads.

1.2.4. Bait Effectiveness

Figure 10:
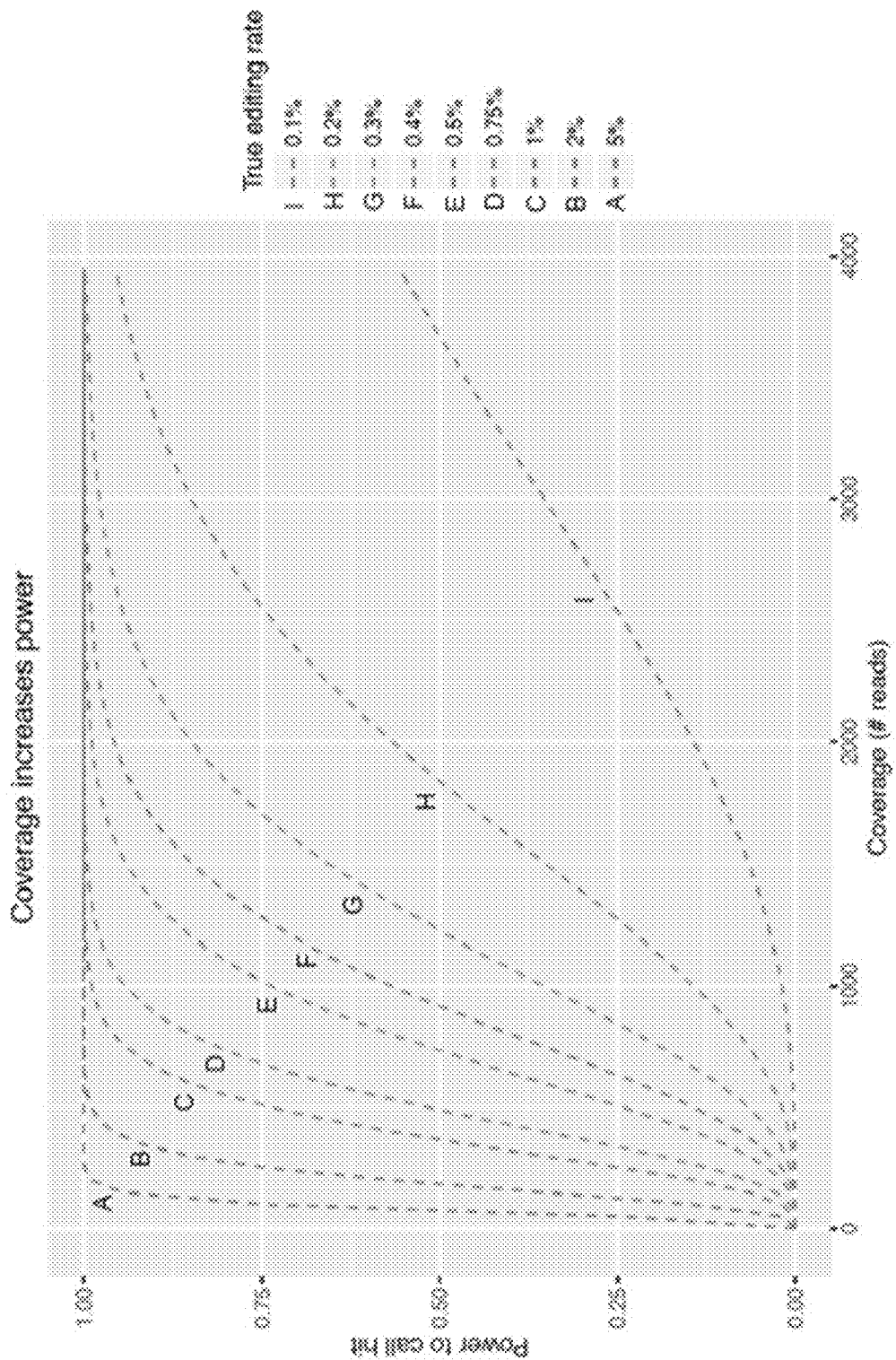
FIG. 10 shows a graph depicting the hybrid capture method's power to detect indels.

In a typical experiment we find that baits cover the large majority of the target sites with high levels of sequencing coverage. There are some limitations to the sequencing coverage that may be achieved by next-generation sequencing (NGS) methods due to: high or low % GC, low-complexity sequences, low bait affinity, bait non-specificity, and other reasons. The actual power to detect indels in an experiment is estimated by calculating the sampling power of different sequencing coverage for sites with different true indel frequencies. Generally, increased sequence coverage provides increased power to detect sites with low-frequency indels. For example, if a site has 2500× sequencing coverage, hybrid capture will have 99% power to see sites with 0.4% indel frequency, and 94% power to see sites with 0.3% indel frequency (FIG. 10).

1.2.5. Quantification

Sequencing data is aligned with the BWA algorithm using default parameters to the human genome build hg38. For each potential off-target site, all indels within 3 bp of the potential Cas9 cleavage site are counted and divided by the coverage at the cut site and thus provides a quantity of indels at a particular cut site.

1.2.6. Statistical Assessment of Significant Cut Sites

Various events can lead to indels that are not a result of CRISPR-Cas9 being detected at sites throughout the genome: germline indel variants or polymorphisms, regions susceptible to genomic breaks, regions with homopolymer runs, and regions that are otherwise difficult to sequence 1.2.6.1. Sites Excluded from Analysis We exclude from analysis: any sites with a "germline" indel on a donor-by-donor basis (donor has >30% indel frequency in every sample), any chromosome Y sites in female samples, and any sites with 0 coverage.

1.2.6.2. Statistical Test

To assess whether an indel seen at a potential off-target site is truly a CRISPR-Cas9 induced event, we test whether the samples treated with Cas9 and guide have a significantly higher frequency of indels than the untreated samples using both Mann-Whitney Wilcoxon test and Student's t-test. If either of these tests is significant (p<0.05) we consider the site flagged for follow-up with PCR to determine if there is significant editing. To ensure that we flag sites for follow-up as aggressively as possible, we do not perform multiple hypothesis testing correction, which would decrease the number of sites that we find significant.

Candidate off-target sites were identified using two orthogonal and complementary approaches-computational prediction and experimental nomination. Computational prediction was done by identifying sites with homology to the on-target site allowing for mismatches and DNA-RNA bulges (2141 candidate sites identified for CG-001). Experimental site nomination was done via GUIDE-seq modified for sequencing on an Illumina NextSeq instrument (Tsai et al., Nat Biotech 2015) (51 candidate sites identified for CG-001). All sites identified by both methods were followed up by enrichment by hybrid capture probes and targeted next generation sequencing in CD34+ cells.

The results from this comprehensive off-target assessment included a determination that CG-001 gRNA does not have off-target editing. Specifically, the success of the GUIDE-seq experiment was confirmed by a high on-target read count of nearly 100,000 reads for the CG-001. Further, it has been previously observed that sites from the GUIDE-seq experiment with the fewest mismatches to the on-target site and highest read count typically have a higher chance of being a true off-target site. For the cells treated with CG-001, no sites with high homology (<10 mismatches) and high read count (>1,000 reads) were observed, indicating that CG-001 likely has no off-target editing. In contrast to CG-001, samples treated by other guides in the same experiment (1619 gRNA (SEQ ID NO: 15) and 1621 gRNA (SEQ ID NO: 16)) that passed quality control (with high on-target read count) nominated many candidate sites with high read count and few mismatches to the on-target site. In other words, a gRNA can pass the quality control check and still have many candidate off-target sites.

In the conclusive targeted next-generation sequencing assessment of all nominated sites for the CG-001 gRNA, no evidence of editing was observed at any of the candidate off-target sites for CG-001, based on comparison of CG-001 and RNP-treated cells with matched untreated cells.

The same off-target assessment for the CG-002 guide also indicated that it does not have off-target editing activity. Notably, there was a high on-target read count for the CG-002 on-target site in the GUIDE-seq experiment, with only 3 nominated sites having high homology and high read count. The conclusive targeted next-generation sequencing of all nominated sites resulted in no evidence of off-target editing at any of the candidate off-target sites for the CG-002 gRNA.

Example 9—Cell Viability and Cell Proliferation

Figure 7A:
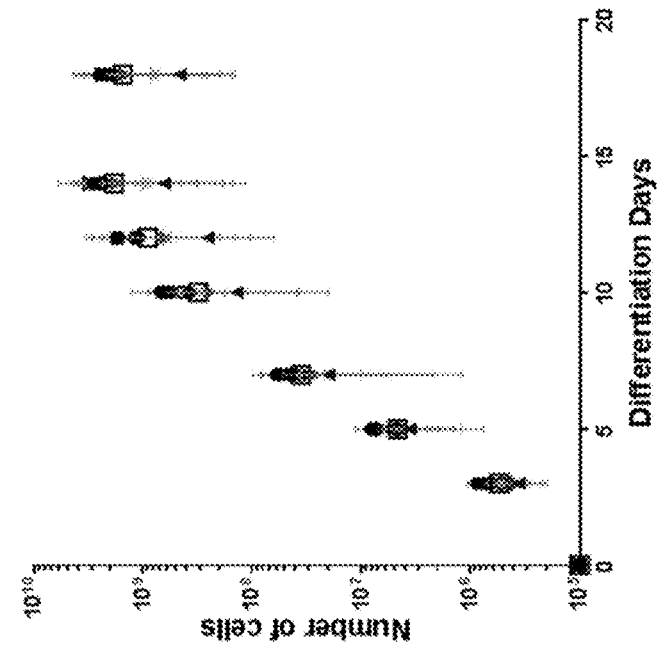
FIGS. 7A-7B show cell viability and cell proliferation at various time-points throughout erythroid differentiation for human mPB CD34+HSPCs electroporated with Cas9 protein and different gRNAs.
Figure 7B:
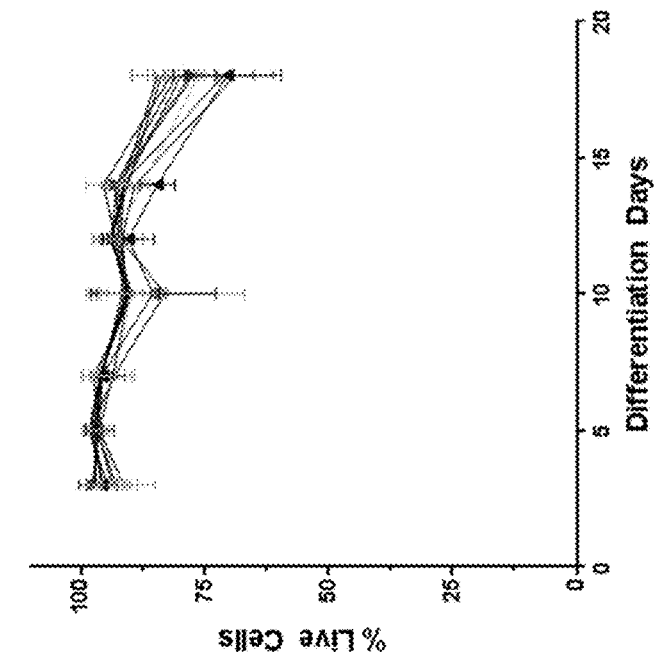

Cell health of each of the electroporated mPBs CD34+ cells during erythroid differentiation described herein was accessed by measuring the viability and growth kinetics of the electroporated mPBs CD34+ cells during erythroid differentiation at various time points (Day 3, Day 5, Day 7, Day 10, Day 12, Day 14, and Day 18 of differentiation). Each time point after D0 refers to a stage of mPB CD34+ cell differentiation to erythrocytes, such D3, D5, D7, D10, D12, and D14. As demonstrated in FIGS. 7A-B, cell viability and cell growth kinetics are similar between mPB CD34+ cells electroporated with SPY101 sgRNA and Cas9 protein, cells electroporated with SD2 sgRNA and Cas9 protein, cells electroporated with CG-001 sgRNA and Cas9 protein, cells electroporated with CG-002 sgRNA and Cas9 protein, cells electroporated with CG-001+CG-002 sgRNAs and Cas9 protein, cells electroporated with HPFH5-1+HPFH5-D sgRNAs and Cas9 protein, cells electroporated with HPFH5-5+HPFH5-D sgRNAs and Cas9 protein, cells electroporated with Kenya K5/17 sgRNAs and Cas9 protein, cells electroporated with Exon 2 sgRNAs and Cas9 protein (positive control), cells electroporated with EGFP and Cas9 protein (negative control), and mock electroporated cells.

Example 10—Erythroid Differentiation and Enucleation

Differentation of mPBs CD34+ cells into erythrocytes for each of the electroporated mPBs CD34+ cells described herein was accessed by measuring the expression of CD71, Band3, GlyA, and Alpha4 Integrin for each of the electroporated mPBs CD34+ cells at various time points (Days 10, 12, 14, 18) via FACs analysis. As demonstrated in FIGS. 8B-E, there were minimal differences in differentiation between mPB CD34+ cells electroporated with SPY101 sgRNA and Cas9 protein, cells electroporated with SD2 sgRNA and Cas9 protein, cells electroporated with CG-001 sgRNA and Cas9 protein, cells electroporated with CG-002 sgRNA and Cas9 protein, cells electroporated with CG-001+CG-002 sgRNAs and Cas9 protein, cells electroporated with HPFH5-1+HPFH5-D sgRNAs and Cas9 protein, cells electroporated with HPFH5-5+HPFH5-D sgRNAs and Cas9 protein, cells electroporated with Kenya K5/17 sgRNAs and Cas9 protein, cells electroporated with Exon 2 sgRNAs and Cas9 protein (positive control), cells electroporated with EGFP and Cas9 protein (negative control), and mock electroporated cells.

Differentation of mPBs CD34+ cells to erythrocytes for each of the electroporated mPBs described herein was also accessed by measuring the percentage of enucleation for each of the electroporated mPBs at various time points (Day 12, Day 14, and Day 18). As demonstrated in FIG. 8A, there were minimal differences in enucleation between mPB CD34+ cells electroporated with SPY101 sgRNA and Cas9 protein, cells electroporated with SD2 sgRNA and Cas9 protein, cells electroporated with CG-001 sgRNA and Cas9 protein, cells electroporated with CG-002 sgRNA and Cas9 protein, cells electroporated with CG-001+CG-002 sgRNAs and Cas9 protein, cells electroporated with HPFH5-1+HPFH5-D sgRNAs and Cas9 protein, cells electroporated with HPFH5-5+HPFH5-D sgRNAs and Cas9 protein, cells electroporated with Kenya K5/17 sgRNAs and Cas9 protein, cells electroporated with Exon 2 sgRNAs and Cas9 protein (positive control), cells electroporated with EGFP and Cas9 protein (negative control), and mock electroporated cells.

Example 11—In Vivo Testing in Relevant Animal Model

After the CRISPR-Cas9/DNA donor combinations have been re-assessed, the lead formulations will be tested in vivo in an animal model.

Culture in human cells allows direct testing on the human target and the background human genome, as described above.

Preclinical efficacy and safety evaluations can be observed through engraftment of modified mouse or human CD34+ cells in NSG or similar mice. The modified cells can be observed in the months after engraftment.

In vivo engraftment studies were performed in immunocompromised mice to confirm that the gene-edited HSPCs retain the potential for long-term repopulation of the hematopoietic system. Human CD34+HSPCs from healthy donors were either edited using CG-001 RNP or EGFP RNP (control) using the Maxcyte® device and injected via tail vein into NSG or NSG$^{cKit}$ mice to demonstrate homing and engraftment capabilities. NSG mice were irradiated with 200 cGy; NSG$^{cKit}$ mice, which carry cKit mutation to allow higher human cell engraftment, were irradiated with 100 cGy prior to xenotransplantation of edited cells. NSG is a strain of inbred laboratory mice and among the most immunodeficient described to date; see, e.g., Shultz et al., Nat. Rev. Immunol. 7(2): 118-130 (2007). NSG$^{cKit}$ is a new strain of NSG mice harboring mutation in the mouse Kit receptor which not only results in higher engraftment capacity for human cells than NSG, but also enhanced multi-lineage reconstitution of engrafted human cells thus allowing human erythropoiesis that is typically undetectable in the NSG strain; see McIntosh et al., Stem Cell Reports 4(2): 171-180 (2015) and Yurino et al., Stem Cell Reports 7(3): 425-438 (2016).

Figure 12:
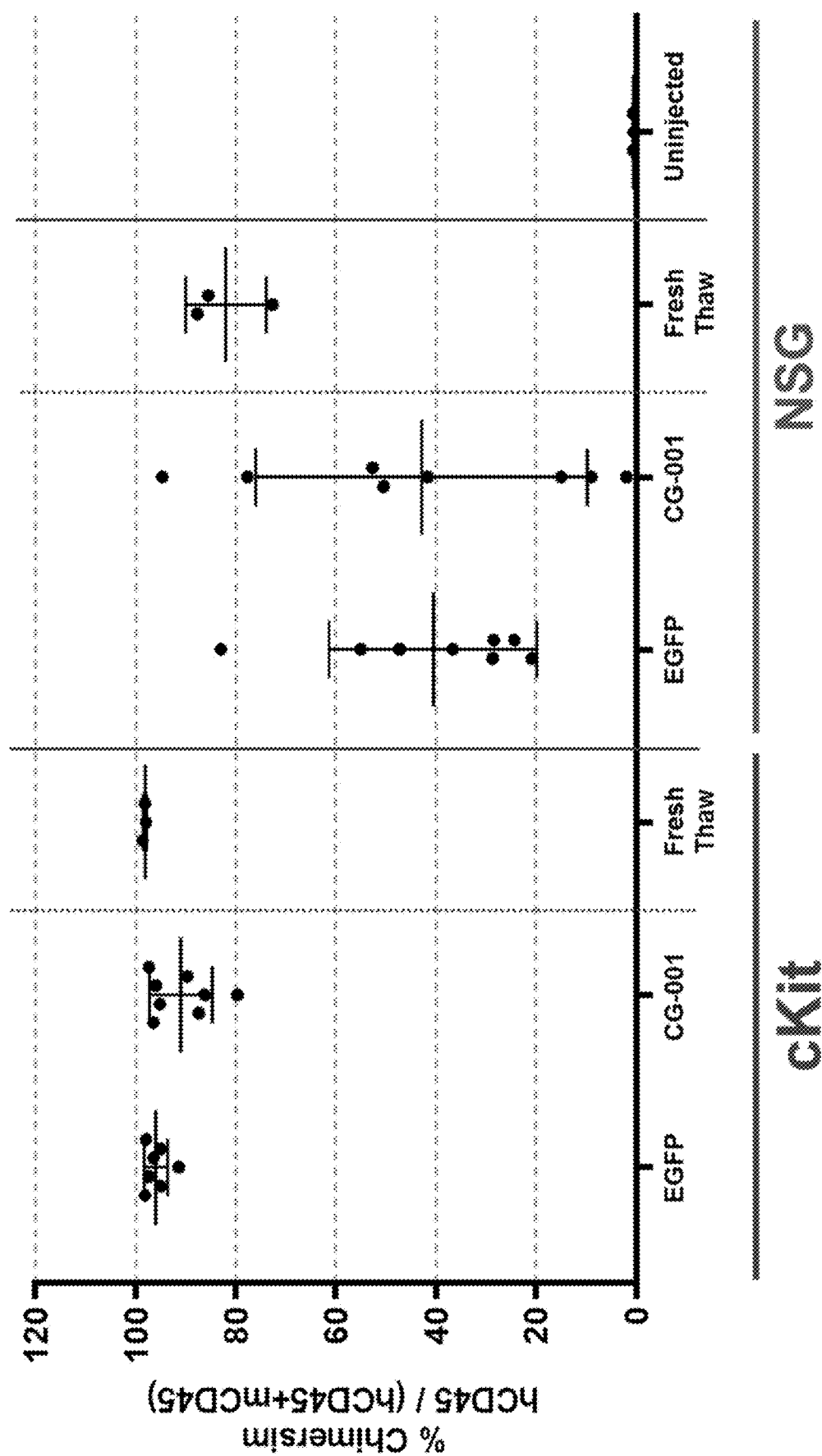
FIG. 12 shows analysis of human CD45+ cell populations in bone marrow of NSG or NSG$^{cKit}$ mice 16 weeks post-engraftment with either EGFP or CG-001 edited human mPB CD34+HSPCs. NSG mice were irradiated with 200 cGy; NSG$^{cKit}$ mice, which carry cKit mutation to allow higher human cell engraftment, were irradiated with 100 cGy prior to xenotransplantation of edited cells. "Fresh thaw" condition refers to mice injected with uncultured and unedited mPB CD34+HSPCs. "Uninjected" condition refers to mice injected with saline only. Data points represent individual animals and depict the percentage of human leukocyte chimerism, which is the percentage of live human CD45+ cells out of all live human CD45+ plus live mouse CD45+ leukocytes. The bars represent Mean±SD.

At 16-weeks post-injection, the mice were sacrificed and the bone marrow were analyzed via FACS for human CD45+ leukocytes shown in FIG. 12. Data points represent individual animals and depict the percentage of live cells that were human CD45+ normalized to total live leukocytes, which were comprised of human CD34+ and mouse CD45+ cells (bars represent Mean±SD). Engraftment of human cells were observed in all groups except in control mice that were not injected with human cells ("Uninjected"). Overall NSG$^{cKit}$ mice showed higher human chimerism than NSG, as expected. There was also no difference in human chimerism between mice injected with control EGFP RNP or CG-001 RNP-edited cells. As expected, mice injected with "Fresh Thaw" human mPB CD34+HSPCs (uncultured and unedited) showed the maximal human chimerism.

Figure 13:
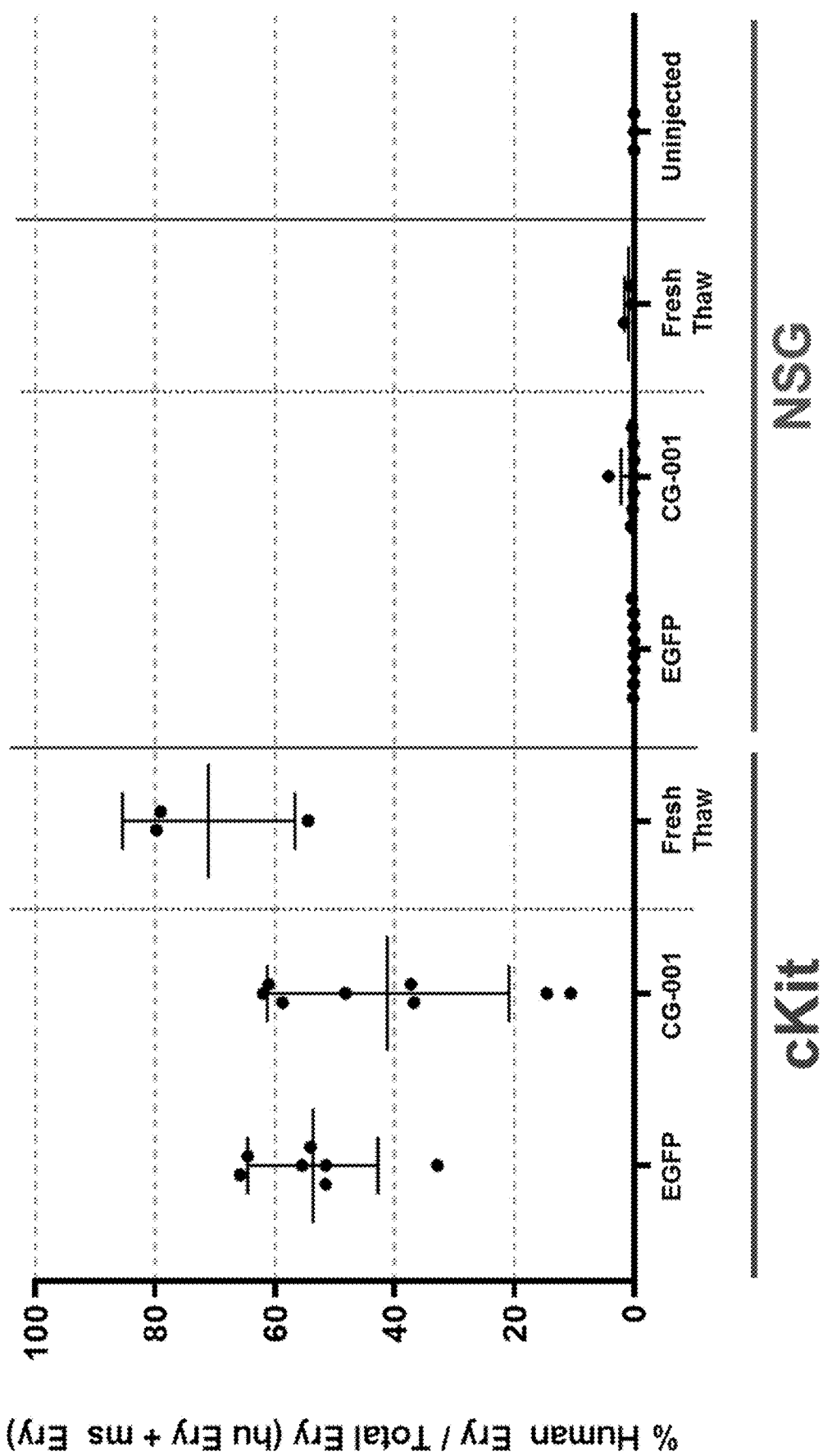
FIG. 13 shows analysis of human GlyA+ cell populations in bone marrow of NSG or NSG$^{cKit}$ mice 16 weeks post-engraftment with either EGFP or CG-001 edited human mPB CD34+HSPCs from FIG. 12. "Fresh thaw" condition refers to mice injected with uncultured and unedited mPB CD34+HSPCs. "Uninjected" condition refers to mice injected with saline only. Data points represent individual animals and depict the percentage of human erythrocyte chimerism, which is the percentage of live human GlyA+ cells out of all live human GlyA+ plus live mouse mTER119+ erythrocytes. The bars represent Mean±SD.

The percentage of human erythroid chimerism was determined via FACS for human GlyA+ erythrocytes shown in FIG. 13. Data points represent individual animals and depict the percentage of live cells that were human GlyA+ normalized to total live erythrocytes, which were comprised of human GlyA+ and mouse mTER119+ cells (bars represent Mean±SD). NSG$^{cKit}$ mice showed high human erythrocyte chimerism where as NSG mice did not, as expected. There was also no difference in human erythrocyte chimerism between mice injected with control EGFP RNP or CG-001 RNP-edited cells.

Furthermore, myeloid and lymphoid chimerism were similar between the two groups (data not shown). These results demonstrate that CG-001 did not affect mPB CD34+ HSPC function in engrafting long-term or in multi-lineage differentiation.

To demonstrate the CG-001 editing persists in whole bone marrow after long-term engraftment, genomic DNA were extracted from bone marrow of mice injected with CG-001 RNP edited mPB CD34+HSPCs after 16 weeks post-engraftment and analyzed for Indel frequency by amplicon NGS. Shown in FIG. 14, the input mPB CD34+ cells had an editing frequency of 97% and that this editing persisted in the bone marrow of all eight mice after 16 weeks. Further analysis on the Indel species distribution from each of the bone marrow samples all showed similar editing frequency distributions as input mPB CD34+ cells (data not shown).

Figure 15:
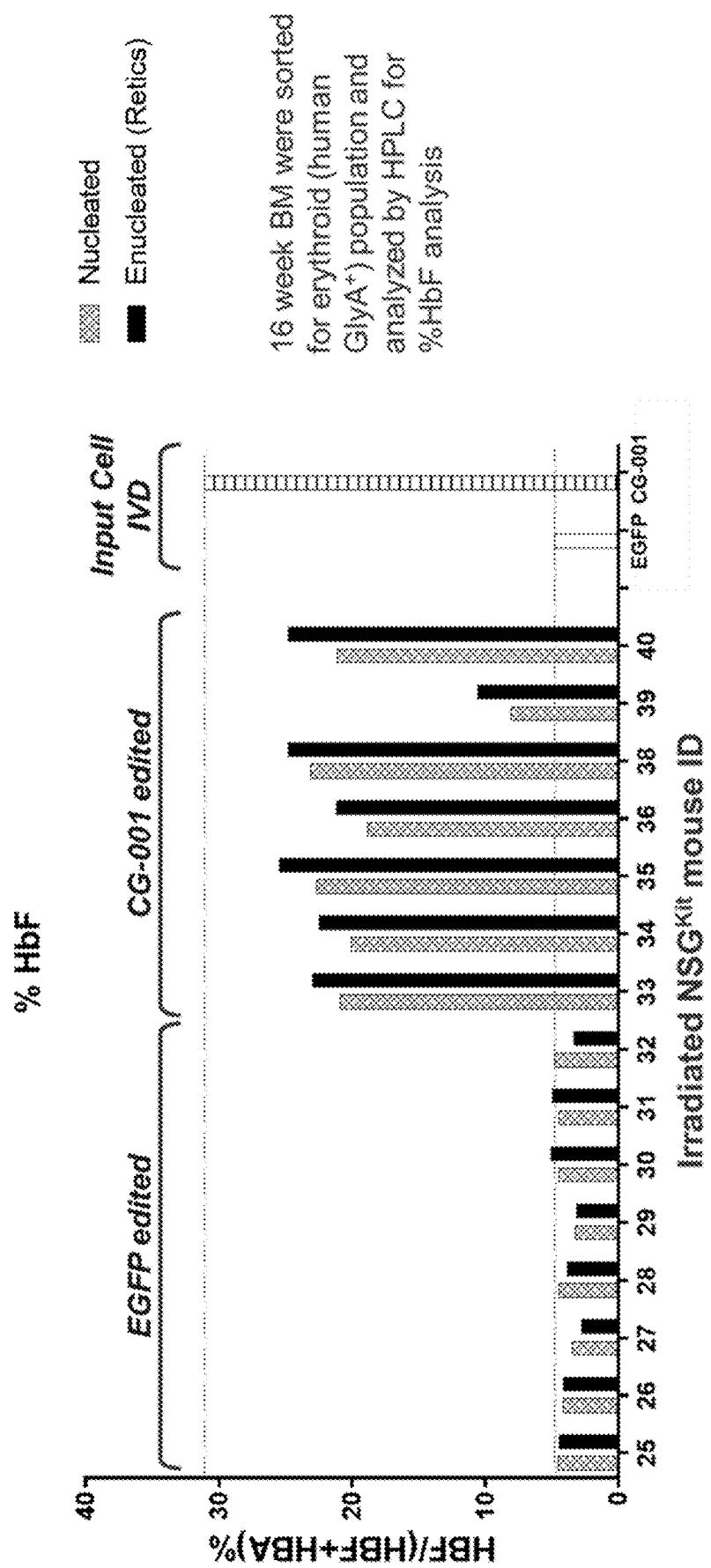
FIG. 15 shows percentage of HbF in total hemoglobins (HbF/(HbF+HbA)) measured from human GlyA+ erythrocytes isolated from the bone marrow of NSG$^{cKit}$ mice 16 weeks post-engraftment with either EGFP or CG-001 edited human mPB CD34+HSPCs from FIG. 12. Human GlyA+ cells were further sorted as either nucleated (less mature) or enucleated (mature reticulocytes) erythrocytes to examine % HbF level differences. The right side of the graph depict erythrocytes from in vitro erythroid differentiation ("Input Cell IVD") of the same input human mPB CD34+HSPCs edited with EGFP or CG-001 prior to engraftment into mice.

To demonstrate that CG-001 editing persists in human erythrocytes after long-term engraftment and that editing results in functional upregulation of HbF production, GlyA+ human erythrocytes were FACS sorted from the bone marrow after 16 weeks post-engraftment. Shown in FIG. 15, human erythrocytes from mice injected with CG-001 RNP edited mPB CD34+ cells produced as much HbF protein as those same input edited mPB CD34+ cells after in vitro erythroid differentiation. Similar HbF upregulation were observed in slightly immature erythrocytes (Nucleated) and mature reticulocytes (Enucleated).

Example 12—Genotype to Phenotype Correlation

Three possible gene editing outcomes may occur within intron 2 of the BCL11A gene when using CG-001 sgRNA. The first gene editing outcome that may occur when using CG-001 sgRNA results in Indel in both alleles (bi-allelically edited); the second gene editing outcome that may occur results in Indel in only one allele while the other allele remains wild-type (mono-allelic edited); the third gene editing outcome that may occur results in wild-type sequences in both alleles (non-edited).

To better understand the genotype-to-phenotype relationship in CG-001 edited erythroid cells, single BFU-E cell derived colony analysis was performed. BFU-E cells are the most primitive CD34+ progenitor cells that are committed to the erythroid lineage. CG-001 edited mPB CD34+HSPCs were sorted as single BFU-E cells into 96-well plates and in vitro erythroid differentiated for 18 days to form colonies large enough so that genomic DNA can be extracted for genotyping and that HbF protein can be extracted for IEX-HPLC analysis.

Figure 16A:
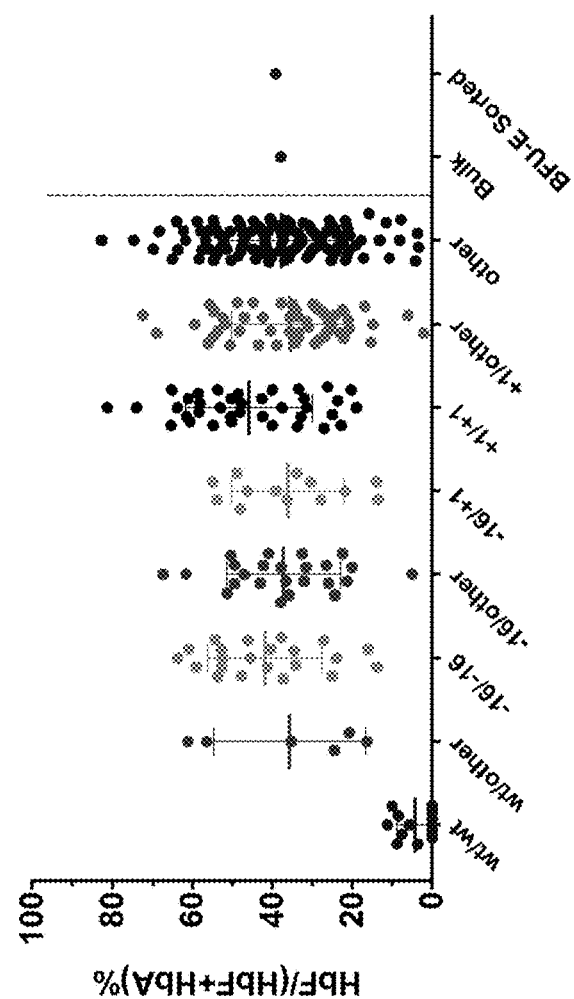
FIG. 16A shows the percentage of HbF in total hemoglobins (HbF/(HbF+HbA)) measured from single BFU-E-derived erythroid colonies of CG-001 edited mPB CD34+HSPCs. A total of 294 colonies were analyzed for Indels detected from each allele and binned into bi-allelically edited, mono-allelically edited or non-edited colonies with their distribution indicated. Bars indicate Mean±SD.
Figure 16B:
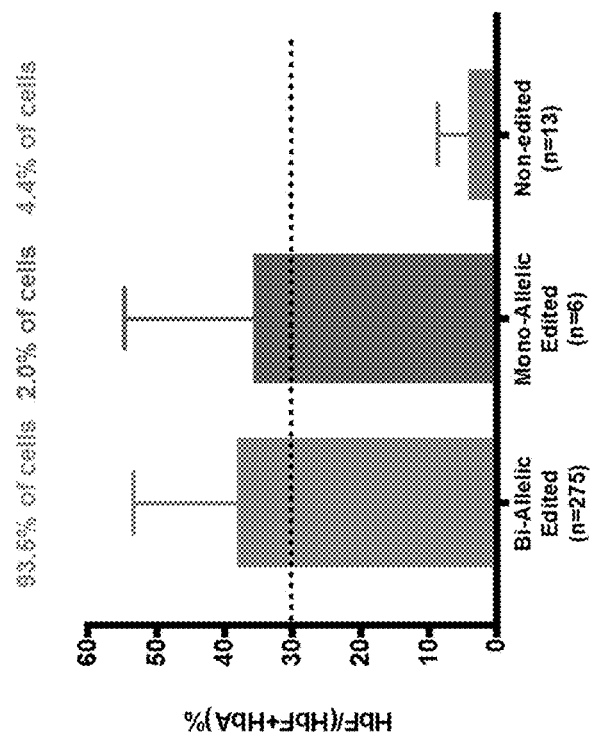
FIG. 16B shows the percentage of HbF in total hemoglobins (HbF/(HbF+HbA)) measured from single BFU-E-derived erythroid colonies of CG-001 edited mPB CD34+HSPCs from FIG. 16A, further binned into the types of Indel detected on each allele. CG-001 gave rise to predominantly 16 bp deletion (−16) or 1 bp insertion (+1) types of Indels. The colonies were binned into either non-edited (wt/wt), mono-allelically edited (wt/other), homozygous −16 edited (−16/−16), heterozygous −16 and +1 (−16/+1), heterozygous −16 not paired with +1 (−16/other) homozygous+1 edited (+1/+1), heterozygous+1 not paired with −16 (+1/other) and all other bi-allelically edited (other) colonies. In vitro erythroid differentiation of bulk mPB CD34+HSPCs or bulk BFU-E cells were also measured for percentage of HbF and plotted on the right side of the graph. Bars indicate Mean±SD.

Shown in FIG. 16A, over 93% of the colonies analyzed were bi-allelically edited and that these colonies produced high levels of HbF. CG-001 RNP editing produces two types of Indels predominantly: a 16 bp deletion (−16) and a 1 bp insertion (+1). When the colonies were further analyzed for the type of Indels, they were binned according to whether they contained −16 and or +1 or any other Indels ("other"). Shown in FIG. 16B, all colonies that contain any of the combinations showed increase in HbF production, demonstrating that most of the Indels produced by CG-001 are productive. These colonies also produce similar levels of HbF compared to bulk differentiated CD34+HSPCs or BFU-E cells.

Further analysis of the NSG$^{ckit}$ engrafted mice, demonstrated that after 16 weeks the indel distribution profile in bone marrow remained similar to the distribution profile of the engraftment input cells (data not shown).

Example 13—Human Mobilized Peripheral Blood (mPB) CD34+HSPC Transplantation into NSG Mice Methods Electroporation of human mPB CD34+HSPCs and Cell Prep for transplantation mPB CD34+HSPCs were thawed, washed and re-suspended in complete stem cell medium at a density of 2-5×10$^5$/ml and incubated at 37 degrees C. in an incubator for 48 hours. Cells were electroporated with RNP using a Maxcyte electroporator as described in Example 11. Cells were re-suspended in complete stem cell medium at a density of 2-5×10$^5$/ml and incubated at 37 degrees C. for 24 hours. Cells were then incubated at 37 degrees C. for another 24 hours. Cells were then washed with PBS+0.5% Human Serum albumin (HSA) and resuspended in sterile saline at 2.5×10$^6$/ml. This was used to transplant into NSG mice.

Transplantation of Human mPB CD34+HSPCs into NSG Mice 6-8 week old female NSG mice were purchased from Jackson laboratory (Bar Harbour, see also Development of functional human blood and immune systems in NOD/SCID/IL2 receptor {gamma} chain(null) mice. Blood. 2005; 106(5):1565-73 and Human lymphoid and myeloid cell development in NOD/LtSz-scid IL2R gamma null mice engrafted with mobilized human hemopoietic stem cells. J Immunol. 2005; 174(10):6477-89). 24 hours prior to transplantation recipient mice were given a sub-lethal dose of gamma irradiation (2 Gy) to destroy some of the resident bone marrow. 200 μl of cells at a density of 2.5×10$^6$/ml were transplanted via tail vein injections into NSG mice. Mice were randomly assigned into experimental groups. Each experimental group has 10 mice per group.

Assessment of Human Engraftment

At 16 weeks post transplant mice were euthanized and mouse bones (2 femur, 2 tibia/fibula and sternum), spleen and whole blood were collected. Bone marrow was harvested from bones by crushing the bones with PBS+0.5% FBS+2 mM EDTA with a mortar and pestle. The cell supernatant was filtered through a 70 μm cell strainer and washed with PBS+0.5% FBS+2 mM EDTA. Splenocytes were isolated by mashing spleens with frosted glass slides and filtering through a 70 μm cell strainer. Human lineage cells were analyzed in bone marrow, splenocytes and whole blood (WB) at week 16. Cells were blocked for nonspecific antibody binding (human and mouse Fc block, Miltenyi Biotec) and stained with hCD45, mCD45, hCD19, hCD3, hCD33 for 30 minutes, 4 degrees C., in the dark. Cells were analyzed for surface marker expression using a BD FACSCanto Analyzer. Data analysis was done using FloJo cytometry data analysis software.

Results

Figure 17:
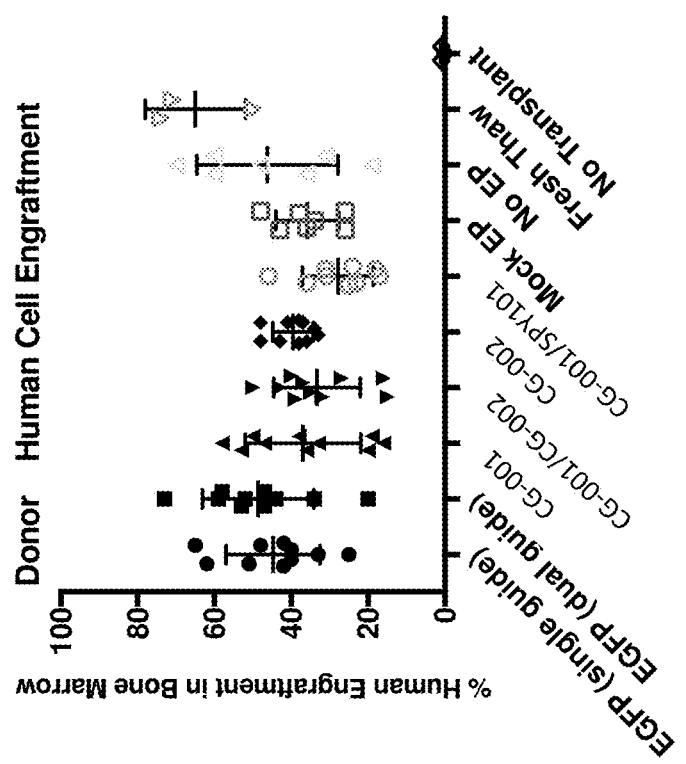
FIG. 17 shows the percent engraftment of human cells from an example donor in the bone marrow of NSG mice after transplantation. EP=electroporation.
Figure 18:
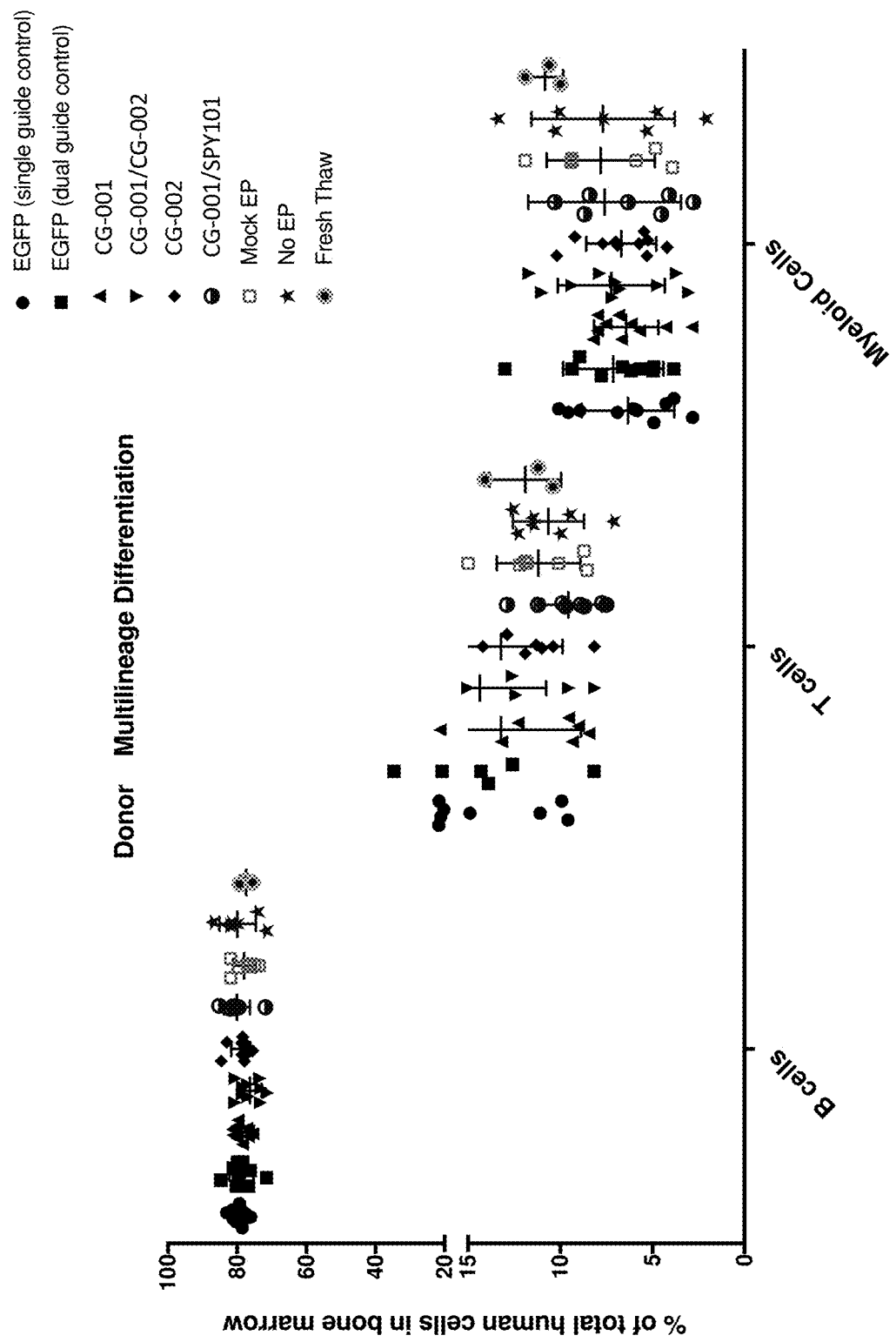
FIG. 18 shows multilineage differentiation of human cells from an example donor transplanted into NSG mice. EP=electroporation.

In vivo studies demonstrated equivalent engraftment (human chimerism) and differentiation of B-, T-, myeloid in bone marrow of NSG-ckit mice at 16 weeks post transplant. In particular, human chimerism (% hCD45+ cells) in bone marrow of NSG mice transplanted with cells was not significantly different in any test group from from controls. Furthermore, B-, T-, and myeloid cell differentiation in NSG mice transplanted with cells was not significantly different in any test group from control. FIGS. 17 and 18 provide a representative example of engraftment/chimerism (FIG. 17) and differentiation (FIG. 18) for cells from a single human donor.

NOTE REGARDING ILLUSTRATIVE EXAMPLES

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

What is claimed is:

1. A method for editing a B-cell lymphoma 11A (BCL11A) gene in a human cell by genome editing, the method comprising:
introducing into the human cell one or more deoxyribonucleic acid (DNA) endonucleases, a first single-molecule guide RNA (sgRNA) and a second sgRNA to effect two or more single-strand breaks (SSBs) or double-strand breaks (DSBs), within or near the BCL11A gene or other DNA sequence that encodes a regulatory element of the BCL11A gene, that results in at least one of a permanent insertion, deletion, modulation, and an inactivation of a transcriptional control sequence of the BCL11A gene, wherein the one or more DNA endonucleases are Cas9 endonucleases, and wherein:
(i) the first sgRNA comprises the nucleic acid sequence of SEQ ID NO: 11 and the second sgRNA comprises the nucleic acid sequence of SEQ ID NO: 12, or
(ii) the first sgRNA comprises the nucleic acid sequence of SEQ ID NO: 11 and the second sgRNA comprises the nucleic acid sequence of SEQ ID NO: 13, or
(iii) the first sgRNA comprises the nucleic acid sequence of SEQ ID NO: 12 and the second sgRNA comprises the nucleic acid sequence of SEQ ID NO: 13.

2. The method of claim 1, wherein the method comprises introducing into the human cell one or more polynucleotides encoding the one or more DNA endonucleases or wherein the method comprises introducing into the human cell one or more ribonucleic acids (RNAs) encoding the one or more DNA endonucleases, optionally wherein the one or more polynucleotides or the one or more RNAs is one or more modified polynucleotides or one or more modified RNAs.

3. The method of claim 1, wherein the one or more DNA endonucleases each comprise, at the N-terminus, the C-terminus, or both the N-terminus and C-terminus, one or more nuclear localization signals (NLSs), optionally wherein the one or more DNA endonucleases each comprise two NLSs, one NLS located at the N-terminus and the second NLS located at the C-terminus and/or wherein the one or more NLSs is a SV40 NLS.

4. The method of claim 1, wherein the one or more DNA endonucleases is pre-complexed with the first and/or second sgRNAs to form one or more ribonucleoproteins (RNPs), optionally wherein the weight ratio of sgRNAs to DNA endonuclease in the one or more RNPs is 1:1, further optionally wherein the DNA endonuclease is a *S. pyogenes* Cas9 comprising a N-terminus SV40 NLS and a C-terminus SV40 NLS, further optionally wherein the one or more RNPs is delivered to the cell by electroporation.

5. The method of claim 1, wherein the first sgRNA comprises the nucleic acid sequence of SEQ ID NO: 11, the Cas9 endonuclease is a *S. pyogenes* Cas9 comprising a N-terminus SV40 NLS and a C-terminus SV40 NLS, wherein the weight ratio of the first and/or the second sgRNA to Cas9 endonuclease is 1:1 or wherein the first sgRNA comprises the nucleic acid sequence of SEQ ID NO: 12, the Cas9 endonuclease is a *S. pyogenes* Cas9 comprising a N-terminus SV40 NLS and a C-terminus SV40 NLS, wherein the weight ratio of sgRNA to Cas9 endonuclease is 1:1.

6. The method of claim 1, wherein:
(a) an mRNA encoding the one or more Cas9 endonucleases and the first and/or second sgRNA are either each formulated into separate lipid nanoparticles or all co-formulated into a lipid nanoparticle, or
(b) an mRNA encoding the one or more Cas9 endonucleases is formulated into a lipid nanoparticle, and the first and/or second sgRNA are delivered to the cell by an adeno-associated virus (AAV) vector, or
(c) an mRNA encoding the one or more Cas9 endonucleases is formulated into a lipid nanoparticle, and the first and/or second sgRNA are delivered to the cell by electroporation.

7. An ex vivo method for treating a patient with a hemoglobinopathy, the method comprising:
(a) editing within or near a B-cell lymphoma 11A (BCL11A) gene or other DNA sequence that encodes a regulatory element of the BCL11A gene of an induced pluripotent stem cell (iPSC) or a mesenchymal stem cell, optionally wherein the mesenchymal stem cell is isolated from the patient's bone marrow or peripheral blood by aspiration of bone marrow and isolation of mesenchymal cells using density gradient centrifugation media;
(b) differentiating the genome-edited iPSC or mesenchymal stem cell into a hematopoietic progenitor cell, optionally wherein the differentiating step comprises one or more of the following to differentiate the genome-edited iPSC or mesenchymal stem cell into a hematopoietic progenitor cell: treatment with a combination of small molecules, delivery of master transcription factors, delivery of mRNA encoding master transcription factors, or delivery of mRNA encoding transcription factors; and
(c) implanting the hematopoietic progenitor cell into the patient, optionally wherein the implanting step comprises implanting the hematopoietic progenitor cell into the patient by transplantation, local injection, systemic infusion, or combinations thereof; and
wherein step (a) is performed by the method of claim 1.

8. An ex vivo method for treating a patient with a hemoglobinopathy, the method comprising:
(a) editing within or near a B-cell lymphoma 11A (BCL11A) gene or other DNA sequence A that encodes a regulatory element of the BCL11A gene of a cell, optionally wherein the cell is a bone marrow cell, a hematopoietic progenitor cell, or a CD34+ cell; and
(b) implanting the genome-edited hematopoietic progenitor cell into the patient, optionally wherein the implanting step comprises implanting the genome-edited hematopoietic progenitor cell into the patient by transplantation, local injection, systemic infusion, or combinations thereof,
optionally further comprising: isolating the hematopoietic progenitor cell from the patient, optionally by treating the patient with granulocyte colony stimulating factor (GCSF) and/or 1,1'-(1,4-phenylenebismethylene)bis(1, 4,8,11-tetraazacyclotetradecane) prior to the isolating step
further optionally wherein the hemoglobinopathy is selected from a group consisting of sickle cell anemia and thalassemia ($\alpha$, $\beta$, $\delta$, $\gamma$, and combinations thereof), and
wherein step (a) is performed by the method of claim 1.

9. An in vivo method for treating a patient with a hemoglobinopathy, the method comprising: (a) editing a B-cell lymphoma 11A (BCL11A) gene in a cell of the patient, wherein step (a) is performed by the method of claim 1, optionally wherein the hemoglobinopathy is selected from a group consisting of sickle cell anemia and thalassemia ($\alpha$, $\beta$, $\delta$, $\gamma$, and combinations thereof).

10. A kit comprising:
(i) a first gRNA comprising the nucleic acid sequence of SEQ ID NO: 11;
(ii) a second gRNA comprising the nucleic acid sequence of SEQ ID NO: 12; and
(iii) a third gRNA comprising the nucleic acid sequence of SEQ ID NO: 13,
optionally wherein (i), (ii), and/or (iii) is a modified gRNA and/or a sgRNA,
further optionally wherein the gRNAs in the kit are formulated in one composition.

11. The method of claim 1, wherein the first sgRNA comprises the nucleic acid sequence of SEQ ID NO: 11 and the second sgRNA comprises the nucleic acid sequence of SEQ ID NO: 12.

12. The method of claim 1, wherein the first sgRNA comprises the nucleic acid sequence of SEQ ID NO: 11 and the second sgRNA comprises the nucleic acid sequence of SEQ ID NO: 13.

13. The method of claim 1, wherein the first sgRNA comprises the nucleic acid sequence of SEQ ID NO: 12 and the second sgRNA comprises the nucleic acid sequence of SEQ ID NO: 13.

14. A genetically engineered cell, which comprises genetic mutations, each of which is one of a permanent insertion, deletion, modulation, and an inactivation of a transcriptional control sequence of a BCL11A gene, wherein the genetic mutations occur at one or more sites targeted by a first sgRNA and a second sgRNA, wherein:
(i) the first sgRNA comprises the nucleic acid sequence of SEQ ID NO: 11 and the second sgRNA comprises the nucleic acid sequence of SEQ ID NO: 12, or
(ii) the first sgRNA comprises the nucleic acid sequence of SEQ ID NO: 11 and the second sgRNA comprises the nucleic acid sequence of SEQ ID NO: 13, or
(iii) the first sgRNA comprises the nucleic acid sequence of SEQ ID NO: 12 and the second sgRNA comprises the nucleic acid sequence of SEQ ID NO: 13,
optionally wherein the cell is a CD34+ human cell, further optionally a CD34+ human hematopoietic stem and progenitor cell.

15. The genetically engineered cell of claim 14, wherein the cell exhibits a HbF mean percentage of HbF/(HbF+HbA) protein levels of at least 10%, optionally at least 15%, further optionally at least 20%, further optionally at least 25%, further optionally at least 30%, further optionally at least 40%, further optionally at least 50%.

16. A cell population comprising the genetically engineered cell of claim 14, optionally wherein the population comprises cells having at least two different genetic mutations, further optionally wherein at least 70% of the population maintain multi-lineage potential for at least sixteen weeks after administration of the population to a subject; and/or wherein the population exhibits a mean allele editing frequency of 70% to 90%; and/or wherein the population exhibits a HbF mean percentage of HbF/(HbF+HbA) protein levels of at least 10%; and/or wherein the population exhibits an off-target indel rate of less than 1%.

17. A method for treating a patient with a hemoglobinopathy, comprising administering to a subject in need thereof an effective amount of the cell population of claim 16, optionally wherein the hemoglobinopathy is selected from a group consisting of sickle cell anemia and thalassemia ($\alpha$, $\beta$, $\delta$, $\gamma$, and combinations thereof).

* * * * *

UNITED STATES PATENT AND TRADEMARK OFFICE
CERTIFICATE OF CORRECTION

| | |
|---|---|
| PATENT NO. | : 11,566,236 B2 |
| APPLICATION NO. | : 16/267693 |
| DATED | : January 31, 2023 |
| INVENTOR(S) | : Tirtha Chakraborty et al. |

It is certified that error appears in the above-identified patent and that said Letters Patent is hereby corrected as shown below:

In the Claims

At Column 109, Line 55, Claim number 8:
"(BCL11A) gene or other DNA sequence A that encodes"
Should be:
-- (BCL11A) gene or other DNA sequence that encodes --

Signed and Sealed this
Fourth Day of July, 2023

Katherine Kelly Vidal
*Director of the United States Patent and Trademark Office*

```
                              SEQUENCE LISTING

<160> NUMBER OF SEQ ID NOS: 16

<210> SEQ ID NO 1
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(21)
<223> OTHER INFORMATION: n is a, c, g, or u

<400> SEQUENCE: 1
nnnnnnnnnn nnnnnnnnnn nrg                                           23

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

Leu Ala Gly Leu Ile Asp Ala Asp Gly
1               5

<210> SEQ ID NO 3
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: n is a, c, g, or u

<400> SEQUENCE: 3
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 4
<211> LENGTH: 96
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: n is a, c, g, or u

<400> SEQUENCE: 4
nnnnnnnnnn nnnnnnnnnn guuuuagagc uagaaauagc aaguuaaaau aaggcuaguc    60
cguuaucaac uugaaaaagu ggcaccgagu cggugc                             96

<210> SEQ ID NO 5
<211> LENGTH: 107
<212> TYPE: RNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<222> LOCATION: (1)..(13)
<223> OTHER INFORMATION: may be absent
<220> FEATURE:
<221> NAME/KEY: misc_feature
<222> LOCATION: (1)..(30)
<223> OTHER INFORMATION: n is a, c, g, or u

<400> SEQUENCE: 5
nnnnnnnnnn nnnnnnnnnn nnnnnnnnnn guuuuagagc uagaaauagc aaguuaaaau    60
aaggcuaguc cguuaucaac uugaaaaagu ggcaccgagu cggugcu                 107

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
tgcttggtcg gcactgatag                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
atcagaggcc aaacccttcc                                               20

<210> SEQ ID NO 8
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 8
tgcttggtcg gcactgatag ggg                                           23

<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 9
atcagaggcc aaacccttcc tgg                                           23

<210> SEQ ID NO 10
<211> LENGTH: 80
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (77)..(79)
<223> OTHER INFORMATION: may be modified by 2'-O-methyl phosphorothioate

<400> SEQUENCE: 10
```

```
guuuuagagc uagaaauagc aaguuaaaau aaggcuaguc cguuaucaac uugaaaaagu        60
ggcaccgagu cggugcuuuu                                                    80

<210> SEQ ID NO 11
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: may be modified by 2'-O-methyl phosphorothioate
<220> FEATURE:
<221> NAME/KEY: misc_feature
<222> LOCATION: (97)..(99)
<223> OTHER INFORMATION: may be modified by 2'-O-methyl phosphorothioate

<400> SEQUENCE: 11
ugcuuggucg gcacugauag guuuuagagc uagaaauagc aaguuaaaau aaggcuaguc        60
cguuaucaac uugaaaaagu ggcaccgagu cggugcuuuu                             100

<210> SEQ ID NO 12
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: may be modified by 2'-O-methyl phosphorothioate
<220> FEATURE:
<221> NAME/KEY: misc_feature
<222> LOCATION: (97)..(99)
<223> OTHER INFORMATION: may be modified by 2'-O-methyl phosphorothioate

<400> SEQUENCE: 12
aucagaggcc aaaccuucc guuuuagagc uagaaauagc aaguuaaaau aaggcuaguc         60
cguuaucaac uugaaaaagu ggcaccgagu cggugcuuuu                             100

<210> SEQ ID NO 13
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: may be modified by 2'-O-methyl phosphorothioate
<220> FEATURE:
<221> NAME/KEY: misc_feature
<222> LOCATION: (97)..(99)
<223> OTHER INFORMATION: may be modified by 2'-O-methyl phosphorothioate

<400> SEQUENCE: 13
cuaacaguug cuuuuaucac guuuuagagc uagaaauagc aaguuaaaau aaggcuaguc        60
cguuaucaac uugaaaaagu ggcaccgagu cggugcuuuu                             100

<210> SEQ ID NO 14
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 14
```

```
cuaacaguug cuuuuaucac                                               20

<210> SEQ ID NO 15
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: may be modified by 2'-O-methyl phosphorothioate
<220> FEATURE:
<221> NAME/KEY: misc_feature
<222> LOCATION: (97)..(99)
<223> OTHER INFORMATION: may be modified by 2'-O-methyl phosphorothioate

<400> SEQUENCE: 15
uuuuaucaca ggcuccagga guuuuagagc uagaaauagc aaguuaaaau aaggcuaguc    60
cguuaucaac uugaaaaagu ggcaccgagu cggugcuuuu                        100

<210> SEQ ID NO 16
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: may be modified by 2'-O-methyl phosphorothioate
<220> FEATURE:
<221> NAME/KEY: misc_feature
<222> LOCATION: (97)..(99)
<223> OTHER INFORMATION: may be modified by 2'-O-methyl phosphorothioate

<400> SEQUENCE: 16
cacaggcucc aggaagggu guuuuagagc uagaaauagc aaguuaaaau aaggcuaguc    60
cguuaucaac uugaaaaagu ggcaccgagu cggugcuuuu                        100
```